United States Patent
Dousson et al.

(10) Patent No.: US 10,766,917 B2
(45) Date of Patent: Sep. 8, 2020

(54) NUCLEOTIDES FOR THE TREATMENT OF CANCER

(71) Applicant: IDENIX PHARMACEUTICALS LLC, Cambridge, MA (US)

(72) Inventors: Cyril B. Dousson, Canet (FR); David Dukhan, Saint Gely du Fesc (FR); Christophe Claude Parsy, Jacou (FR)

(73) Assignee: IDENIX PHARMACEUTICALS LLC, Cambridge, MA (US)

( * ) Notice: Subject to any disclaimer, the term of this patent is extended or adjusted under 35 U.S.C. 154(b) by 16 days.

(21) Appl. No.: 15/576,948

(22) PCT Filed: May 23, 2016

(86) PCT No.: PCT/EP2016/061549
§ 371 (c)(1),
(2) Date: Nov. 27, 2017

(87) PCT Pub. No.: WO2016/188943
PCT Pub. Date: Dec. 1, 2016

(65) Prior Publication Data
US 2018/0155385 A1    Jun. 7, 2018

(30) Foreign Application Priority Data

May 27, 2015 (EP) .................... 15305802

(51) Int. Cl.
*C07H 19/11* (2006.01)
*C07H 19/10* (2006.01)
*A61P 35/00* (2006.01)

(52) U.S. Cl.
CPC ............. *C07H 19/11* (2013.01); *A61P 35/00* (2018.01); *C07H 19/10* (2013.01)

(58) Field of Classification Search
CPC ................ C07H 19/10; C07H 19/11
See application file for complete search history.

(56) References Cited

U.S. PATENT DOCUMENTS

| 3,804,827 | A | 4/1974 | Robins et al. |
| 2008/0221061 | A1 | 9/2008 | Hostetler et al. |
| 2010/0081628 | A1* | 4/2010 | Du ............... C07D 473/18 514/48 |
| 2013/0131008 | A1 | 5/2013 | Cui et al. |
| 2013/0210757 | A1 | 8/2013 | Huang et al. |

FOREIGN PATENT DOCUMENTS

| KR | 20120043870 | | 5/2012 |
| WO | 2009032180 | A1 | 3/2009 |
| WO | 2010101967 | A2 | 9/2010 |
| WO | 2012040126 | A1 | 3/2012 |
| WO | 2012045999 | A1 | 4/2012 |
| WO | 2012088155 | A1 | 6/2012 |
| WO | 2015081297 | | 6/2015 |
| WO | 2015134334 | A1 | 9/2015 |
| WO | 2015081133 | A3 | 12/2015 |
| WO | 2015181624 | A2 | 12/2015 |

OTHER PUBLICATIONS

Slusarczyl, M.; et al., Application of ProTide Technology to Gemcitabine: A Successful Approach to Overcome the Key Cancer Resistance Mechanisms Leads to a New Agent (NUC-1031) in Clinical Development, Journal of Medicinal Chemistry, 2014, pp. 1531-1542, 57.
Wu et al., Synthesis and biological activity of a gemcitabine phosphoramidate prodrug, Journal of Medicinal Chemistry, 2007, 3743-3746, 50(15).
Bender, David M., Synthesis, Crystallization, and Biological Evaluation of an Orally Active Prodrug of Gemcitabine, Journal of Medicinal Chemistry Letters, 2009, 6958-6961, 52.

* cited by examiner

*Primary Examiner* — Jonathan S Lau
(74) *Attorney, Agent, or Firm* — Jeffrey P. Bergman; Catherine D. Fitch

(57) ABSTRACT

The present invention relates to novel nucleoside derivatives, pharmaceutical compositions comprising the compounds, processes of preparation thereof, and methods of use thereof for treating cancer.

7 Claims, No Drawings

NUCLEOTIDES FOR THE TREATMENT OF CANCER

FIELD

Provided herein are nucleoside derivatives, pharmaceutical compositions comprising the compounds, processes of preparation thereof, and methods of use thereof for treating cancer.

In certain embodiments, nucleoside and nucleotide compounds and prodrugs are provided which can display remarkable efficacy and bioavailability for the treatment of, for example, liver cancers in a human. Liver cancers which can be treated include primary and secondary liver cancers. In particular embodiments, the liver cancer is hepatocellular carcinoma, cholangiocarcinoma, or biliary tract cancer. In particular embodiments, the liver cancer is a metastasis in the liver originated from other cancers (such as colon cancer, pancreatic cancer, etc.). In certain embodiments, the compounds described herein can be used to treat cancers such as breast cancer, ovarian cancer, lung cancer, pancreatic cancer and leukemic cancer.

BACKGROUND

Cancer is a disease characterized primarily by an uncontrolled division of abnormal cells derived from a given normal tissue and the invasion of adjacent tissues by these malignant cells. Blood or lymphatic transportation can spread cancer cells to other parts of the body leading to regional lymph nodes and to distant sites (metastasis). Cancer is a complex, multistep process that begins with minor preneoplastic changes, which may under certain conditions progress to neoplasia. There are more than 100 different types of cancer, which can be grouped into broader categories. The main categories include: carcinoma, sarcoma, leukemia, lymphoma and myeloma, and central nervous system cancers. The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer.

Hematologic or hematopoietic malignancies are cancers of the blood or bone marrow, including leukemia and lymphoma. Leukemia is a type of cancer of the blood characterized by abnormal accumulation of immature white blood cells. There are four types of leukemia: acute lymphocytic leukemia (ALL), acute myelogenous leukemia (AML), chronic lymphocytic leukemia (CLL), and chronic myelogenous leukemia (CML). Acute leukemia is a rapidly progressing disease that results in the accumulation of immature, functionless cells in the marrow and blood. The marrow often stops producing enough normal red cells, white cells and platelets. On the other hand, chronic leukemia progresses more slowly and allows greater numbers of more mature, functional cells to be made.

Leukemia can affect people at any age. The cause of most cases of leukemia is not known. Extraordinary doses of radiation and certain cancer therapies are possible causes. About 90% of leukemia are diagnosed in adults. ICases of Chronic leukemia account for 4.5 percent more cases than acute leukemia. The most common types of leukemia in adults are acute myelogenous leukemia (AML), with estimated 14,590 new cases in 2013, and chronic lymphocytic leukemia (CLL), with about 15,680 new cases in 2013. Chronic myelogenous leukemia (CML) was estimated to affect about 5,920 persons in 2013 (data from the Leukemia and Lymphoma Society, *Facts* 2013, August 2013).

The dramatic improvement in blood cancer treatment in the latter part of the $20^{th}$ century is largely the result of chemotherapy. In addition, there are more than 50 drugs individually used to treat these disorders and a number of potential new therapies are under investigation in clinical trials. While current chemotherapy can result in complete remissions, the long term disease-free survival rate for leukemia, in particular AML, is low. For example, the overall relative survival rate for AML was estimated to be about 59% from 2003 to 2009. Therefore, there is a clear and unmet need for effective therapeutics for treatment of blood cancers, including leukemia.

Primary liver cancer is one of the most common forms of cancer in the world. Hepatocellular carcinoma, also known as malignant hepatoma, is the most common form of primary liver cancer, and develops within the hepatocyte. Hepatocellular carcinoma occurs mostly in men and patients that suffer from cirrhosis. It has been the third leading cause of cancer deaths worldwide (Block T M et al., 2003, *Oncogene* 22:5093-5107). Many patients with hepatocellular carcinoma remain asymptomatic until the disease is in its advanced stages, resulting in ineffective treatment and poor prognosis; the majority of unresectable hepatocellular carcinoma patients die within one year.

Treatment options for hepatocellular carcinoma have been limited, especially in the case of advanced or recurrent hepatocellular carcinoma. Surgery and radiation therapy are options for early stage liver cancer, but not very effective for advanced or recurrent hepatocellular carcinoma. Systematic chemotherapies have not been particularly effective, and there are a very limited number of drugs available for use. The recently approved kinase inhibitor sorafenib has been shown to be effective in treating hepatocellular carcinoma. However, it can slow or stop advanced liver cancer from progressing for only a few months longer than without treatment.

Phosphoramidate derivative of nucleosides are described in WO2013/177219, WO2006/063149, and WO2005/012327.

New therapies for the treatment or prevention of cancer are needed.

SUMMARY

Provided herein are compounds useful, for example, for the treatment of cancer, for example liver cancer. The compounds are nucleoside and nucleotide analogs linked to a prodrug moiety. In certain embodiments the nucleoside and nucleotide analogs linked to a prodrug moiety can display remarkable efficacy or bioavailability, or both, for the treatment of cancer, for example, liver cancer in a human. Liver cancers which can be treated include primary and secondary liver cancers. In particular embodiments, the liver cancer is hepatocellular carcinoma, cholangiocarcinoma, or biliary tract cancer. In particular embodiments, the liver cancer is a metastasis in the liver originated from other cancers (such as colon cancer, pancreatic cancer, etc.). In certain embodiments, the compounds described herein can be used to treat cancers such as breast cancer, ovarian cancer, lung cancer, pancreatic cancer and leukemic cancer.

In certain embodiments, the compounds provided herein are useful in the prevention and treatment of cancer, for example liver cancer such as hepatocellular carcinoma, cholangiocarcinoma, or biliary tract cancer. These compounds or formulations can also be used prophylactically to prevent or retard the progression of clinical illness in individuals who have symptoms of cancer, for example liver cancer such as hepatocellular carcinoma, cholangiocarcinoma, or biliary tract cancer. In certain embodiments, the compounds or formulations described herein can be used to treat cancers such as breast cancer, ovarian cancer, lung cancer, pancreatic cancer and leukemic cancer.

A method for the treatment of a cancer, for example liver cancer such as hepatocellular carcinoma, cholangiocarcinoma, or biliary tract cancer, or metastasis in the liver originated from other cancers (such as colon cancer, pancreatic cancer, etc.), in a subject, such as a human, is also provided that includes administering an effective amount of a compound provided herein, administered either alone or in combination or alternation with another anti-cancer agent, optionally in a pharmaceutically acceptable carrier. In certain embodiments, the cancer is selected from breast cancer, ovarian cancer, lung cancer, pancreatic cancer and leukemic cancer.

Provided herein are compounds according to Formula I:

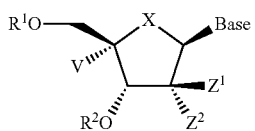

(I)

or a pharmaceutically acceptable salt thereof, wherein:
Base is a nucleobase;
X is O or S;
V is hydrogen, halogen or amino;
$Z^1$ is halogen;
$Z^2$ is halogen;
either one of $R^1$ and $R^2$ is hydrogen and the other is:

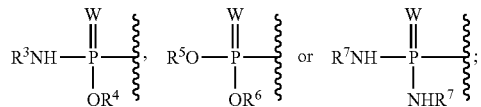

or $R^1$ and $R^2$ together with the two oxygen atoms to which they are attached form the ring:

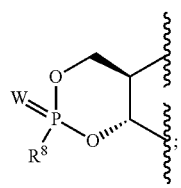

$R^3$ is arylC$_{1-10}$alkyl or

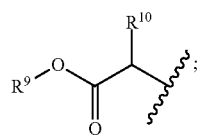

$R^4$ is hydrogen, C$_{1-10}$alkyl, C$_{2-11}$alkenyl, C$_{2-11}$alkynyl, C$_{1-10}$alkoxycarbonylC$_{1-10}$alkyl, C$_{1-10}$ alkyldisulfide C$_{1-10}$alkyl, C$_{1-10}$alkylcarbonylthioC$_{1-10}$alkyl, or heteroarylC$_{1-10}$alkyl, wherein alkyl is optionally substituted by one, two or three substituents independently selected from halogen, and hydroxy, and heteroaryl is optionally substituted by one, two or three substituents independently selected from C$_{1-10}$alkyl and nitro;

$R^5$ is C$_{1-10}$alkyl, C$_{2-11}$alkenyl, C$_{2-11}$alkynyl, C$_{1-10}$alkoxycarbonylC$_{1-10}$alkyl, C$_{1-10}$ alkyldisulfideC$_{1-10}$alkyl, C$_{1-10}$alkylcarbonylthioC$_{1-10}$alkyl or aryl, heteroarylC$_{1-10}$alkyl, wherein alkyl is optionally substituted by one, two or three substituents independently selected from halogen and hydroxy, and the heteroaryl is optionally substituted by one, two or three substituents independently selected from C$_{1-10}$alkyl and nitro;

$R^6$ is hydrogen, C$_{1-10}$alkyl or heteroarylC$_{1-10}$alkyl, wherein the heteroaryl is optionally substituted by one, two or three substituents independently selected from C$_{1-10}$alkyl and nitro;

each $R^7$ is independently

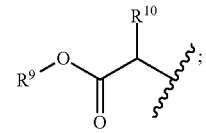

$R^8$ is hydroxy, C$_{1-10}$alkoxy, C$_{1-10}$alkylcarbonylthioC$_{1-10}$alkoxy,

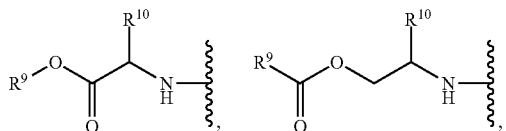

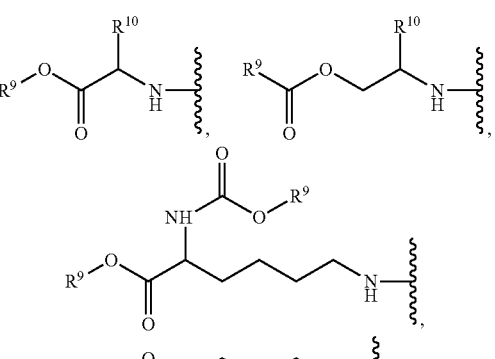

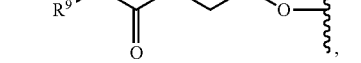

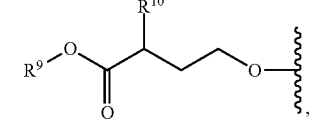

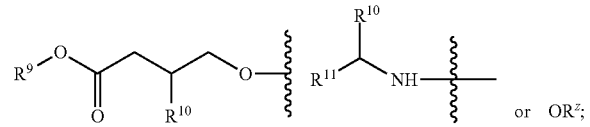

or OR$^z$;

$R^9$ is C$_{1-10}$alkyl, C$_{3-10}$cycloalkyl, aryl or arylC$_{1-6}$alkyl;
$R^{10}$ is C$_{1-10}$alkyl or COOR$^9$;
$R^{11}$ is C$_{1-10}$alkylcarbonyloxyC$_{1-10}$alkyl, C$_{3-10}$cycloalkylcarbonyoxy, aryl, aryloxy, C$_{1-10}$-alkylaryl, arylC$_{1-10}$alkyl, heteroaryl, heteroarylC$_{1-10}$alkyl or C$_{1-10}$alkylheteroaryl;
$R^z$ is C$_{2-11}$alkenyl, C$_{2-11}$ alkynyl, C$_{1-10}$alkoxycarbonyl C$_{1-10}$alkyl, C$_{1-10}$alkylcarbonylthioC$_{1-10}$ alkyl, C$_{1-10}$alkyldisulfideC$_{1-6}$alkyl, aryl or heteroarylC$_{1-10}$alkyl, wherein alkyl is optionally substituted by one, two or three substituents independently selected from halogen and hydroxy, and heteroaryl is substituted by one or two substituents selected from C$_{1-10}$alkyl and nitro; and W is O or S.

In one aspect, the compounds provided herein are provided or administered in combination with a second therapeutic agent, such as one useful for the treatment or prevention of cancer. Exemplary second therapeutic agents are provided in detail elsewhere herein.

In another aspect, provided herein are pharmaceutical compositions, single unit dosage forms, and kits suitable for use in treating or preventing disorders such as cancer, for example liver cancer which comprise a therapeutically or prophylactically effective amount of a compound provided herein, e.g., of Formulas I-VI, and a therapeutically or prophylactically effective amount of a second therapeutic agent such as one useful for the treatment or prevention of cancer, for example liver cancer. In certain embodiments, the cancer is selected from breast cancer, ovarian cancer, lung cancer, pancreatic cancer and leukemic cancer.

In certain embodiments, a method of treatment of a liver disorder is provided comprising administering to an individual in need thereof a treatment effective amount of a compound described herein.

Liver cancers which can be treated include primary and secondary liver cancers. In particular embodiments, the liver cancer is hepatocellular carcinoma, cholangiocarcinoma, or biliary tract cancer.

DESCRIPTION OF EXEMPLARY EMBODIMENTS

Provided herein are compounds, compositions, and methods useful for treating cancer in a subject. Further provided are dosage forms useful for such methods. In certain embodiments, the cancer is selected from liver cancer, breast cancer, ovarian cancer, lung cancer, pancreatic cancer and leukemic cancer.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "alkyl," as used herein, unless otherwise specified, refers to a saturated straight or branched hydrocarbon. In certain embodiments, the alkyl group is a primary, secondary, or tertiary hydrocarbon. The alkyl group includes one to ten carbon atoms, i.e., C$_1$ to C$_{10}$ alkyl. In an embodiment, alkyl group includes one to six carbon atoms, i.e., C$_1$ to C$_6$ alkyl. In certain embodiments, the alkyl group is methyl, ethyl, propyl, isopropyl, butyl, isobutyl, secbutyl, t-butyl, pentyl, isopentyl, neopentyl, hexyl, isohexyl, 3-methylpentyl, 2,2-dimethylbutyl, or 2,3-dimethylbutyl.

The term "cycloalkyl," as used herein, unless otherwise specified, refers to a saturated cyclic hydrocarbon. In certain embodiments, the cycloalkyl group may be a saturated, and/or bridged, and/or non-bridged, and/or a fused bicyclic group. The cycloalkyl group includes three to ten carbon atoms, i.e., C$_3$ to C$_{10}$ cycloalkyl. In some embodiments, the cycloalkyl has from 3 to 15 (C$_{3-15}$), from 3 to 10 (C$_{3-10}$), or from 3 to 7 (C$_{3-7}$) carbon atoms. In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl or adamantyl.

The term "alkenyl" refers to monovalent olefinically unsaturated hydrocarbon groups, having two to 11 carbon atoms, including from 2 to 8 carbon atoms, or from 2 to 6 carbon atoms, which can be straight-chained or branched and having at least 1, including from 1 to 2, site of olefinic unsaturation. Exemplary alkenyl groups include ethenyl (i.e., vinyl, or —CH=CH$_2$), n-propenyl (—CH$_2$CH=CH$_2$), isopropenyl (—C(CH$_3$)=CH$_2$), and the like.

The term "alkynyl" refers to acetylenically unsaturated hydrocarbon groups, having two to 11 carbon atoms or from 2 to 6 carbon atoms which can be straight-chained or branched and having at least 1 or from 1 to 2 sites of alkynyl unsaturation. Non-limiting examples of alkynyl groups include acetylenic, ethynyl (—C≡CH), propargyl (—CH$_2$C≡CH), and the like.

The term "aryl," as used herein, and unless otherwise specified, refers to a substituent derived from an aromatic ring. In an embodiment, an aryl group is a C$_6$-C$_{12}$ aryl group. In an embodiment, an aryl group is phenyl, biphenyl or naphthyl. In an embodiment, aryl is phenyl.

The term "aralkyl" or "arylalkyl" refers to an alkyl group with an aryl substituent, wherein aryl and alkyl are as defined herein.

"Alkylaryl" refers to an aryl group with an alkyl substituent where alkyl and aryl are as defined herein.

"C$_{1-10}$alkoxy" and "C$_{1-10}$alkoxyl" refer to the group —OR' where R' is alkyl as defined herein. The alkoxyl or alkoxy group is —OR', wherein R' is alkyl, and wherein alkyl is C$_1$ to C$_{10}$ alkyl. Alkoxy and alkoxyl groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"C$_{3-10}$cycloalkoxy" and "C$_{3-10}$cycloalkoxyl" refer to the group —OR' where R' is cycloalkyl as defined herein. The alkoxyl or alkoxy group is —OR', wherein R' is cycloalkyl, and wherein cycloalkyl is C$_3$ to C$_{10}$ cycloalkyl.

"Alkylcarbonyloxy" refers to a radical —O—C(O)-alkyl, wherein alkyl is as defined herein.

"Cycloalkylcarbonyloxy" refers to a radical —O—C(O)-cycloalkyl, wherein cycloalkyl is as defined herein.

"Aryloxy" refers to a radical —O-aryl, wherein aryl is as defined herein.

"Alkylcarbonyl" refers to a radical —C(O)-alkyl where alkyl is as defined herein.

"Alkoxycarbonyl" refers to a radical —C(O)-alkoxy where alkoxy is as defined herein.

"Alkoxycarbonylalkyl" refers to a radical -alkyl-C(O)-alkoxy where alkoxy and alkyl are as defined herein.

"Cycloalkoxycarbony" refers to a radical —C(O)-cycloalkoxy where cycloalkoxy is as defined herein.

"Aryloxycarbonyl" refers to a radical —C(O)—O— aryl where aryl is as defined herein.

"Alkoxycarbonylalkoxy" refers to a radical -alkoxy-C(O)-alkoxy where alkoxy and alkyl are as defined herein.

As used herein, "alkylcarbonyloxyalkyl" refers to a radical -alkyl-O—C(O)-alkyl, where alkyl is as defined herein.

As used herein, "alkyldisulfidealkyl" refers to a radical -alkyl-S—S-alkyl, where alkyl is as defined herein.

As used herein, "alkylcarbonylthioalkyl" refers to a radical -alkyl-S—C(O)-alkyl, where alkyl is as defined herein.

"Oxo" refers to the group=O.

"Carboxyl" or "carboxy" refers to the radical —C(O)OH.

"Carbonyl" refers to the radical —C(O).

"Halogen" or "halo" refers to chloro, bromo, fluoro, or iodo.

"Amino" refers to the group —NR$^{1'}$R$^{2'}$ or —NR$^{1'}$—, wherein R' and R$^{2'}$ are independently hydrogen, alkyl, alkenyl, alkynyl, cycloalkyl, heterocycle, aryl, or heteroaryl, each of which is as defined herein. In an embodiment each of R$^{1'}$ and R$^{2'}$ is independently hydrogen or alkyl. In an embodiment each of R$^{1'}$ and R$^{2'}$ is hydrogen.

The term "heterocycle" or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocycle or heterocyclic group has from 3 to 20, from 3 to 15, from 3 to 10, from 3 to 8, from 4 to 7, or from 5 to 6 ring atoms. Heterocycle groups are bonded to the rest of the molecule through the non-aromatic ring. In certain embodiments, the heterocycle is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocycle may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, O-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl.

The term "heteroaryl" refers to a monovalent monocyclic aromatic group and/or multicyclic aromatic group that contain at least one aromatic ring, wherein at least one aromatic ring contains one or more heteroatoms independently selected from O, S and N in the ring. Heteroaryl groups are bonded to the rest of the molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In one embodiment, heteroaryl has 5 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl and xanthenyl. In an embodiment, heteroaryl is selected from imidazoly, thiazolyl, thienyl and furyl. In an embodiment, heteroaryl is N-methylimidazolyl. In certain embodiments, heteroaryl may also be optionally substituted as described herein. In an embodiment heteroaryl is substituted with one nitro group and one methyl group. In an embodiment heteroaryl is substituted with one nitro group.

The term "heteroarylalkyl" refers to an alkyl group with a heteroaryl substituent.

The term "alkylheteroaryl" refers to a heteroaryl group with an alkyl substituent.

The term "protecting group" as used herein and unless otherwise defined refers to a group that is added to an oxygen, nitrogen or phosphorus atom to prevent its further reaction or for other purposes. A wide variety of oxygen and nitrogen protecting groups are known to those skilled in the art of organic synthesis.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, nicotine, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

Unless expressly stated to the contrary, substitution by a named substituent is permitted on any atom in a chain or ring provided such substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

To the extent substituents and substituent patterns provide for the existence of tautomers (e.g., keto-enol tautomers) in the compounds described herein, all tautomeric forms of these compounds, whether present individually or in mixtures, are within the scope of the present disclosure. Compounds of the present disclosure having a hydroxy substituent on a carbon atom of a heteroaromatic ring are understood to include compounds in which only the hydroxy is present, compounds in which only the tautomeric keto form (i.e., an oxo substituent) is present, and compounds in which the keto and enol forms are both present.

As used herein when referring to a substituent on a sugar ring of a nucleoside, the term "beta" refers to a substituent on the same side of the plane of the sugar ring as the 5' carbon and the term "alpha" refers to a substituent on the opposite side of the plane of the sugar ring from the 5' carbon. As shown below, substituent "A" is in the "alpha" position, and substituent "B" is in the "beta" position with respect to the 5' carbon:

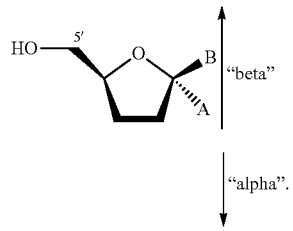

The term "substantially free of" or "substantially in the absence of," when used in connection with an article (including, but not limited to, a compound, a salt thereof, a solvate thereof, a solid form thereof, and the like), refers to the article that includes at least 85% or 90% by weight, in certain embodiments, 95%, 98%, 99%, or 100% by weight, of the designated article. For example, the term "substantially free of" or "substantially in the absence of" with respect to a nucleoside composition can refer to a nucleoside composition that includes at least 85% or 90% by weight, in certain embodiments, 95%, 98%, 99%, or 100% by weight, of the designated stereoisomer of that nucleoside. In certain embodiments, in the methods and compounds provided herein, the compounds are substantially free of undesignated stereoisomers or other compounds. For another example, the term "substantially free of" or "substantially in the absence of" with respect to a solid form can refer to a solid form that includes at least 85% or 90% by weight, in certain embodiments, 95%, 98%, 99%, or 100% by weight, of the designated solid form. In certain embodiments, in the methods and compounds provided herein, the solid form is substantially free of other solid forms.

Similarly, the term "isolated" with respect to a nucleoside composition refers to a nucleoside composition that includes at least 85%, 90%, 95%, 98%, or 99% to 100% by weight, of the nucleoside, the remainder comprising other chemical species or stereoisomers. Similarly, the term "isolated" with respect to a solid form of a compound refers to a solid that includes at least 85%, 90%, 95%, 98%, or 99% to 100% by weight, of such solid form of the compound, the remainder comprising other solid forms of the compound, other compounds, solvents, and/or other impurities.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, terms including "alkyl," "cycloalkyl," "alkenyl," "alkynyl," "aryl," "arylalkyl," "alkoxy," "aryloxy," "alkylcarbonyloxy," "alkoxycarbonyl," "alkoxyalkylcarbonyl," "alkoxycarbonylalkyl," "alkoxycarbonylalkoxy," "alkylcarbonyloxyalkyl" "alkyldisulfidealkyl" "alkylcarbonylthioalkyl," "carboxyl," "carbonyl," "heteroaryl," "heteroarylalkyl," and "amino acid" groups optionally comprise deuterium at one or more positions where hydrogen atoms are present, and wherein the deuterium composition of the atom or atoms is other than the natural isotopic composition.

As used herein, terms including "alkyl," "cycloalkyl," "alkenyl," "alkynyl," "aryl," "arylalkyl," "alkoxy," "aryloxy," "alkylcarbonyloxy," "alkoxycarbonyl," "alkoxyalkylcarbonyl," "alkoxycarbonylalkyl," "alkoxycarbonylalkoxy," "alkylcarbonyloxyalkyl" "alkyldisulfidealkyl" "alkylcarbonylthioalkyl" "carboxyl," "carbonyl," "heteroaryl," "heteroarylalkyl," and "amino acid" groups optionally comprise carbon-13 at an amount other than the natural isotopic composition.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the $IC_{50}$ refers to an amount, concentration or dosage of a particular test compound that achieves a 50% inhibition of a maximal response in an assay that measures such response.

The term "host," as used herein, refers to any unicellular or multicellular organism, including cell lines and animals, and in certain embodiments, a human. Alternatively, the host can be carrying a part of the Flaviviridae viral genome, whose replication or function can be altered by the compounds of the present invention. The term host specifically includes infected cells, cells transfected with all or part of the Flaviviridae genome and animals, in particular, primates (including chimpanzees) and humans. In most animal applications of the present invention, the host is a human patient. Veterinary applications, in certain indications, however, are clearly anticipated by the present invention (such as chimpanzees).

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In another embodiment, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent or impede the onset, development, progression and/or severity of a disorder.

As used herein, the phrase "prophylactically effective amount" refers to the amount of a therapy (e.g., prophylactic agent) which is sufficient to result in the prevention or reduction of the development, recurrence or onset of one or more symptoms associated with a disorder, or to enhance or improve the prophylactic effect(s) of another therapy (e.g., another prophylactic agent).

Compounds

Provided herein are nucleoside compounds useful for the treatment of cancers, for example liver cancers such as hepatocellular carcinoma, cholangiocarcinoma, or biliary tract cancer. The nucleoside compounds can be formed as described herein and used for the treatment of cancers, for example liver cancers such as hepatocellular carcinoma, cholangiocarcinoma, or biliary tract cancer. In certain embodiments, the cancer is selected from breast cancer, ovarian cancer, lung cancer, pancreatic cancer and leukemic cancer.

The compounds described herein may optionally be used in the form of a pharmaceutically acceptable salt. It is understood that references to compounds or pharmaceutically salts thereof would include compounds in present form as well as in different forms, such as polymorphs and solvates (including hydrates), as applicable.

Formula I includes a chiral amino acid residue linked to a 5'-phosphoramidate group. Those of skill in the art will recognize that the amino acid residue has R stereochemistry at the carbon bonded to $R^{10}$; i.e., that it is a D-amino acid residue.

Some compounds provided herein are based, at least in part, on the discovery that D-amino acid phosphoramidate prodrugs can provide superior human pharmacokinetics including superior accumulation of active nucleoside and nucleotide analogs in target cells, such as liver cells. In certain embodiments, the compounds provided herein are D-amino acid, $R_P$ phosphoramidate compounds. In certain embodiments, the compounds provided herein are D-amino acid, $S_P$ phosphoramidate compounds. Any compound provided herein is preferably in the form of a composition that is substantially free of other stereoisomers of the compound, as described herein.

In an embodiment, the compounds described herein are prodrugs of the compound Gemcitabine.

In one embodiment is a compound of formula II:

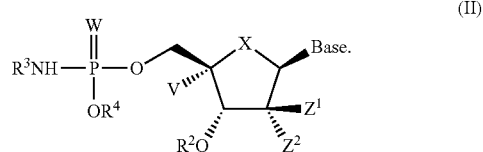

(II)

In one embodiment is a compound of formula III:

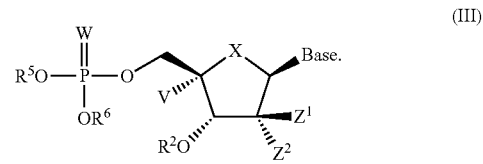

(III)

In one embodiment is a compound of formula IV:

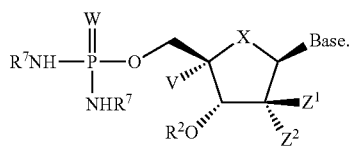
(IV)

In one embodiment is a compound of formula V:

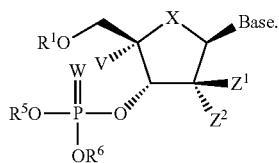
(V)

In one embodiment is a compound of formula VI:

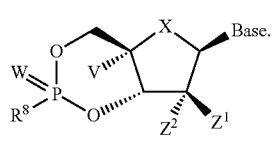
(VI)

The variables for each of formulae I, II, III, IV, V and VI are as defined for formula I.

The following embodiments apply to each one of formulae I, II, III, IV, V and VI.

In an embodiment, V is hydrogen and each of $Z^1$ and $Z^2$ is fluoro.

In an embodiment, X is O, V is hydrogen and each of $Z^1$ and $Z^2$ is fluoro.

In an embodiment $R^2$ is hydrogen.

In an embodiment $R^3$ is aryl$C_{1-6}$alkyl or

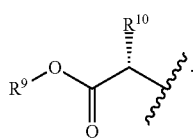

In an embodiment $R^3$ is

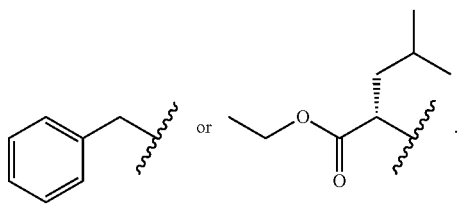 [SMILES: *Cc1ccccc1 ; *[C@@H](CC(C)C)C(=O)OCC]

In embodiment, $R^4$ is hydrogen, $C_{1-10}$alkoxycarbonyl $C_{1-10}$alkyl, $C_{1-10}$alkyldisulfide$C_{1-10}$alkyl, $C_{1-10}$alkylcarbonylthio$C_{1-10}$alkyl or heteroaryl$C_{1-10}$alkyl, wherein heteroaryl is optionally substituted by one, two or three substituents independently selected from $C_{1-6}$alkyl and nitro.

In an embodiment $R^4$ is hydrogen, $C_{1-6}$alkoxycarbonyl $C_{1-6}$alkyl, $C_{1-6}$alkyldisulfide$C_{1-6}$alkyl, $C_{1-6}$alkylcarbonylthio$C_{1-6}$alkyl or heteroaryl$C_{1-6}$alkyl, wherein the heteroaryl is optionally substituted by one, two or three substituents independently selected from $C_{1-10}$alkyl and nitro.

In an embodiment the heteroaryl of $R^4$ is a 5-membered ring.

In an embodiment the heteroaryl of $R^4$ is substituted by two substituents independently selected from $C_{1-10}$alkyl and nitro.

In an embodiment $R^4$ is hydrogen, ethoxycarbonylmethyl, 2-(tert-butyldisulfanyl)ethyl, 3-methyl-2-nitro-imidazol-4-yl or 2-(2,2-dimethylpropanoylsulfanyl)ethyl.

In an embodiment $R^5$ is $C_{1-10}$alkyl, $C_{1-10}$alkylcarbonylthio$C_{1-10}$alkyl or heteroaryl$C_{1-10}$alkyl, wherein alkyl is optionally substituted by one, two or three substituents independently selected from halogen and hydroxy, and the heteroaryl is optionally substituted by one, two or three substituents independently selected from $C_{1-10}$alkyl and nitro.

In an embodiment $R^5$ is $C_{1-6}$alkyl, $C_{1-6}$alkylcarbonylthio$C_{1-6}$alkyl or heteroaryl$C_{1-6}$ alkyl, wherein $C_{1-6}$alkylcarbonylthio$C_{1-6}$alkyl is optionally substituted by hydroxyl and heteroaryl is optionally substituted by nitro.

In an embodiment the heteroaryl of $R^5$ is a 5-membered ring.

In an embodiment the heteroaryl of $R^5$ is substituted by one substituent.

In an embodiment $R^5$ is 2-(2,2-dimethyl-3-hydroxypropanoylsulfanyl)ethyl, isopropyl or (5-nitro-2-furyl)methyl).

In an embodiment $R^6$ is hydrogen, $C_{1-6}$alkyl or heteroaryl$C_{1-6}$alkyl, wherein the heteroaryl is optionally substituted by one, two or three substituents independently selected from $C_{1-10}$alkyl and nitro.

In an embodiment the heteroaryl of $R^6$ is a 5 membered ring selected from $C_{1-10}$alkyl and nitro.

In an embodiment heteroaryl of $R^6$ is substituted by one substituent.

In an embodiment of $R^6$ is hydrogen, isopropyl and (5-nitro-2-furyl)methyl.

In an embodiment $R^7$ is

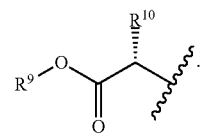

In an embodiment $R^7$ is

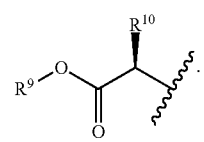

In an embodiment, $R^8$ is hydroxy, $C_{1-10}$alkoxy, $C_{1-10}$alkylcarbonylthio$C_{1-10}$alkoxy,

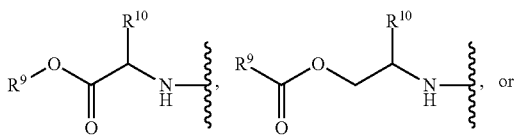

-continued

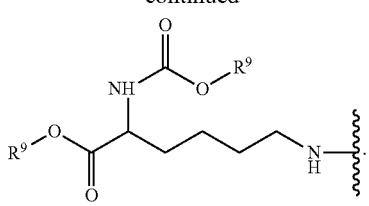

In an embodiment $R^9$ is $C_{1-10}$alkyl, preferably $C_{1-6}$alkyl.

In an embodiment $R^9$ is methyl, ethyl or propyl, for example isopropyl.

In an embodiment $R^{10}$ is $C_{1-6}$alkyl.

In an embodiment $R^{10}$ is methyl or propyl, for example isopropyl.

In an embodiment $R^{10}$ is methyl.

In an embodiment $R^{10}$ is (S)-isopropyl.

In an embodiment $R^{10}$ is (R)-isopropyl.

In an embodiment $R^{10}$ is (S)-methyl.

In an embodiment $R^{10}$ is (R)-methyl.

In an embodiment $R^8$ is hydroxyl, $C_{1-6}$alkoxy, $C_{1-6}$alkylcarbonylthio$C_{1-6}$alkoxy,

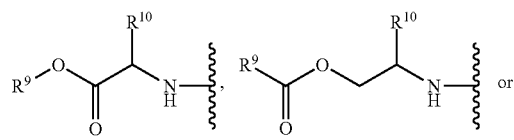

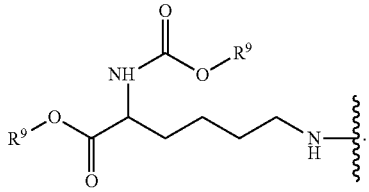

In an embodiment $R^8$ is hydroxy, isopropoxy,

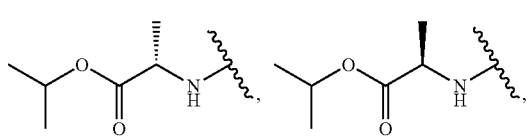

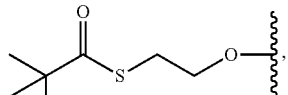

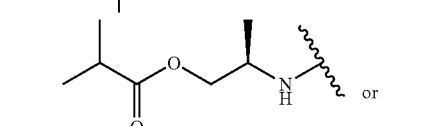

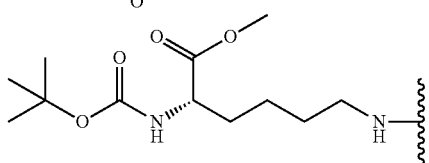

In an embodiment $R^8$ is isopropoxy.
In an embodiment $R^8$ is $C_{1-6}$alkoxy or

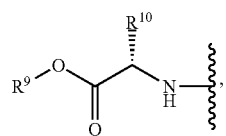

wherein each of $R^9$ and $R^{10}$ is independently $C_{1-6}$alkyl.

In an embodiment $R^8$ is

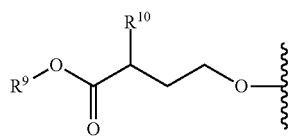

In an embodiment $R^9$ is $C_{1-10}$alkyl, preferably $C_{1-6}$alkyl.
In an embodiment $R^9$ is methyl, ethyl or propyl, for example isopropyl.
In an embodiment $R^9$ is ethyl.
In an embodiment $R^9$ is isopropyl.
In an embodiment $R^{10}$ is $C_{1-6}$alkyl.
In an embodiment $R^{10}$ is methyl or propyl, for example isopropyl.
In an embodiment $R^{10}$ is methyl.
In an embodiment $R^{10}$ is (S)-methyl.
In an embodiment $R^{10}$ is (R)-methyl.
In an embodiment $R^8$ is

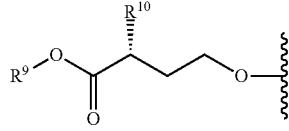

In an embodiment $R^8$ is

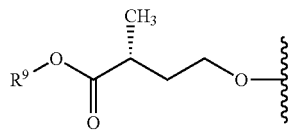

In an embodiment $R^8$ is

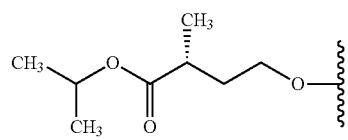

In an embodiment $R^8$ is

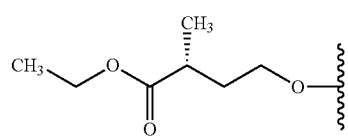 [SMILES: *OCC[C@@H](C)C(=O)OCC]

In an embodiment R$^8$ is

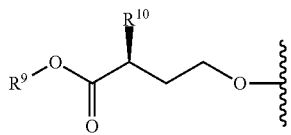

In an embodiment R$^8$ is

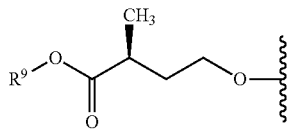

In an embodiment R$^8$ is

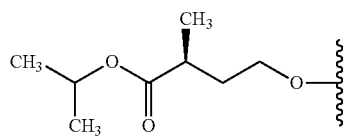 [SMILES: *OCC[C@H](C)C(=O)OC(C)C]

In an embodiment R$^8$ is

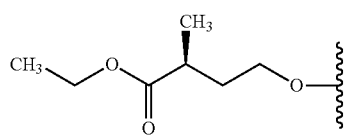 [SMILES: *OCC[C@H](C)C(=O)OCC]

In an embodiment Base is

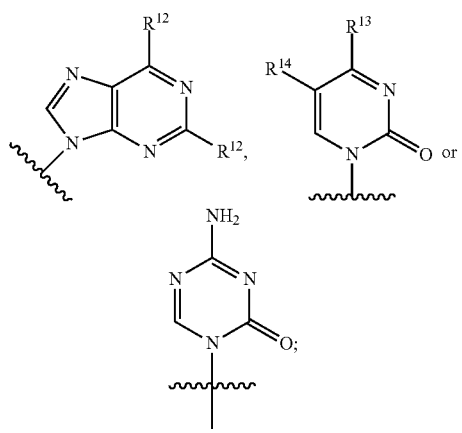

wherein
R$^{12}$ is independently hydrogen, hydroxy, OR$^a$, chloro, bromo, fluoro, iodo, sulfanyl, —NR$^b$R$^c$ or —C$_{1-10}$alkyl-NR$^b$R$^c$;
R$^{13}$ is hydrogen, hydroxy, —NR$^b$R$^c$, azido, oxo, or —OR$^a$;
R$^{14}$ is hydrogen, hydroxy, methyl, chloro, bromo, fluoro, iodo or —NR$^b$R$^c$;
R$^a$ is independently C$_{1-10}$alkyl or C$_{3-10}$Cycloalkyl; and
each of R$^b$ and R$^c$ is independently hydrogen, C$_{1-10}$alkyl, C$_{1-10}$alkylcarbonyl, C$_{2-10}$alkenyl, C$_{2-10}$alkynyl, C$_{3-10}$cy-cloalkyl, aryl, heterocycle, heteroaryl or C(O)Z where Z is a fatty acid chain selected from palmitoleic, oleic, linoleic, or arachidonic acid.

In an embodiment Base is

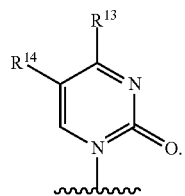

In one embodiment, Base is

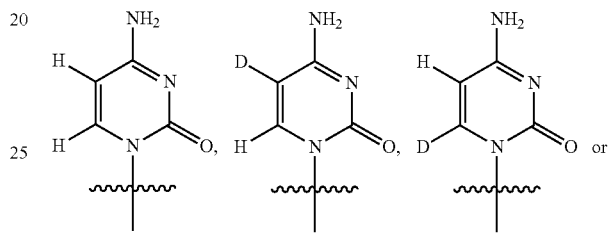

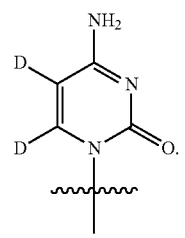

In an embodiment, Base is

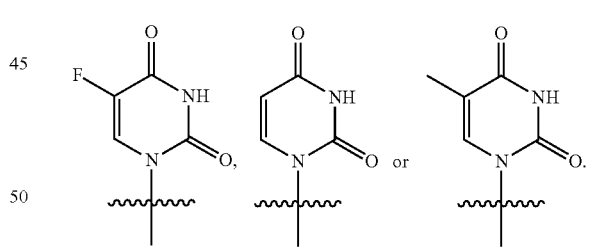

In an embodiment Base is

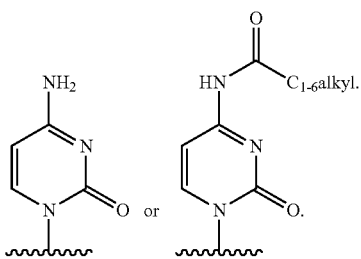

In an embodiment Base is

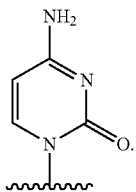 [SMILES: *n1ccc(N)nc1=O]

In one embodiment, Base is

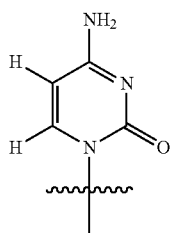

In an embodiment Base is

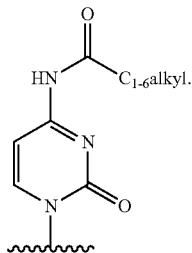

In an embodiment Base is

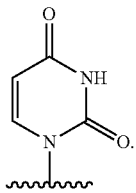 [SMILES: *n1ccc(=O)[nH]c1=O]

In an embodiment $R^{13}$ is —$NR^bR^c$.
In an embodiment $R^{13}$ is —$NR^bR^c$, and each of $R^b$ and $R^c$ is independently hydrogen, $C_{1-10}$alkyl or $C_{1-10}$alkylcarbonyl.
In an embodiment $R^{13}$ is —$NR^bR^c$, and each of $R^b$ and $R^c$ is hydrogen.
In an embodiment $R^{13}$ is —$NR^bR^c$, and one of $R^b$ and $R^c$ is hydrogen and the other $C_{1-10}$alkylcarbonyl.
In an embodiment $R^{14}$ is hydrogen.
In an embodiment each of $R^b$ and $R^c$ is hydrogen, $C_{1-10}$alkyl or $C_{1-10}$alkylcarbonyl.
In an embodiment each of $R^b$ and $R^c$ is hydrogen.
In an embodiment $Z^1$ is fluoro.
In an embodiment $Z^2$ is fluoro.
In an embodiment each of $Z^1$ and $Z^2$ is fluoro.
In an embodiment X is O.
In an embodiment V is hydrogen.

In an embodiment:
W is O;
$R^3$ is aryl$C_{1-6}$alkyl or

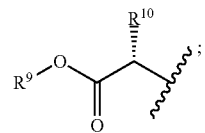

$R^4$ is hydrogen, $C_{1-6}$alkoxycarbonyl$C_{1-6}$alkyl, $C_{1-6}$alkyldisulfide$C_{1-6}$alkyl, $C_{1-6}$alkylcarbonylthio$C_{1-6}$alkyl or heteroaryl$C_{1-6}$alkyl, wherein the heteroaryl is optionally substituted by one, two or three substituents independently selected from $C_{1-10}$alkyl and nitro;
$R^9$ is $C_{1-10}$alkyl; and
$R^{10}$ is $C_{1-6}$alkyl.
In an embodiment
$R^1$ and $R^2$ together with the two oxygen atoms to which they are attached form the ring:

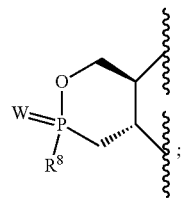

$R^8$ is $C_{1-6}$alkoxy or

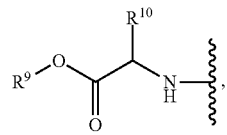

wherein each of $R^9$ and $R^{10}$ is independently $C_{1-6}$alkyl; and
W is O.
In an embodiment
$R^1$ and $R^2$ together with the two oxygen atoms to which they are attached form the ring:

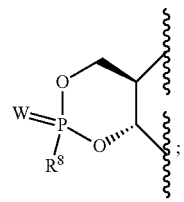

$R^8$ is $C_{1-6}$alkoxy or

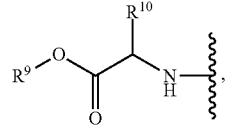

wherein each of $R^9$ and $R^{10}$ is independently $C_{1-6}$alkyl; and
W is O;
X is O;
V is hydrogen;
each of $Z^1$ and $Z^2$ is fluoro;
Base is

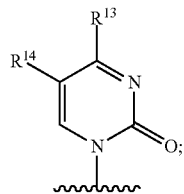

$R^{13}$ is —$NR^bR^c$, and each of $R^b$ and $R^c$ is independently hydrogen, $C_{1-10}$alkyl or $C_{1-10}$alkylcarbonyl; and
$R^{14}$ is hydrogen.

In an embodiment
$R^1$ and $R^2$ together with the two oxygen atoms to which they are attached form the ring:

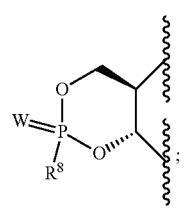

$R^8$ is isopropoxy;
W is O;
X is O;
V is hydrogen;
each of $Z^1$ and $Z^2$ is fluoro;
Base is

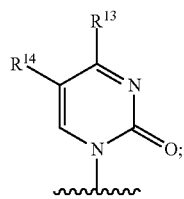

$R^{13}$ is —$NR^bR^c$, and each of $R^b$ and $R^c$ is independently hydrogen, $C_{1-10}$alkyl or $C_{1-10}$alkylcarbonyl; and
$R^{14}$ is hydrogen.

In an embodiment
$R^1$ and $R^2$ together with the two oxygen atoms to which they are attached form the ring:

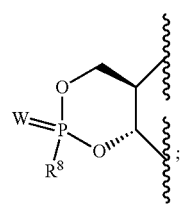

$R^8$ is

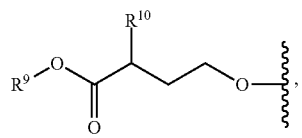

wherein each of $R^9$ and $R^{10}$ is independently $C_{1-6}$alkyl; and
W is O.

In an embodiment
$R^1$ and $R^2$ together with the two oxygen atoms to which they are attached form the ring:

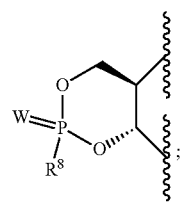

$R^8$ is

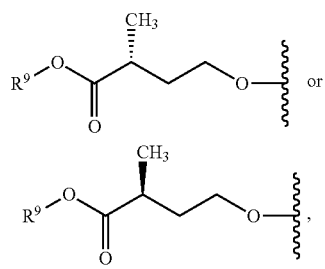

wherein $R^9$ is ethyl or isopropyl; and
W is O;
X is O;
V is hydrogen;
each of $Z^1$ and $Z^2$ is fluoro;
Base is

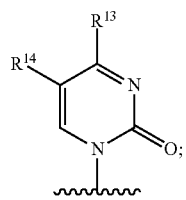

$R^{13}$ is —$NR^bR^c$, and each of $R^b$ and $R^c$ is independently hydrogen, $C_{1-10}$alkyl or $C_{1-10}$alkylcarbonyl; and
$R^{14}$ is hydrogen.

In certain embodiments, provided herein are any of the following compounds:

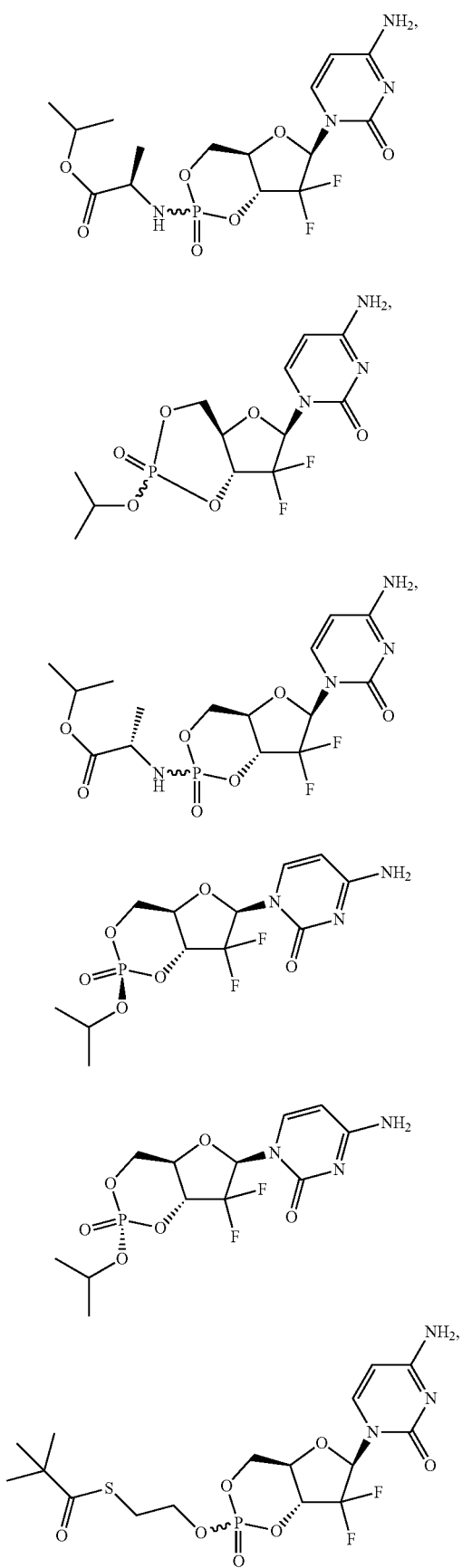
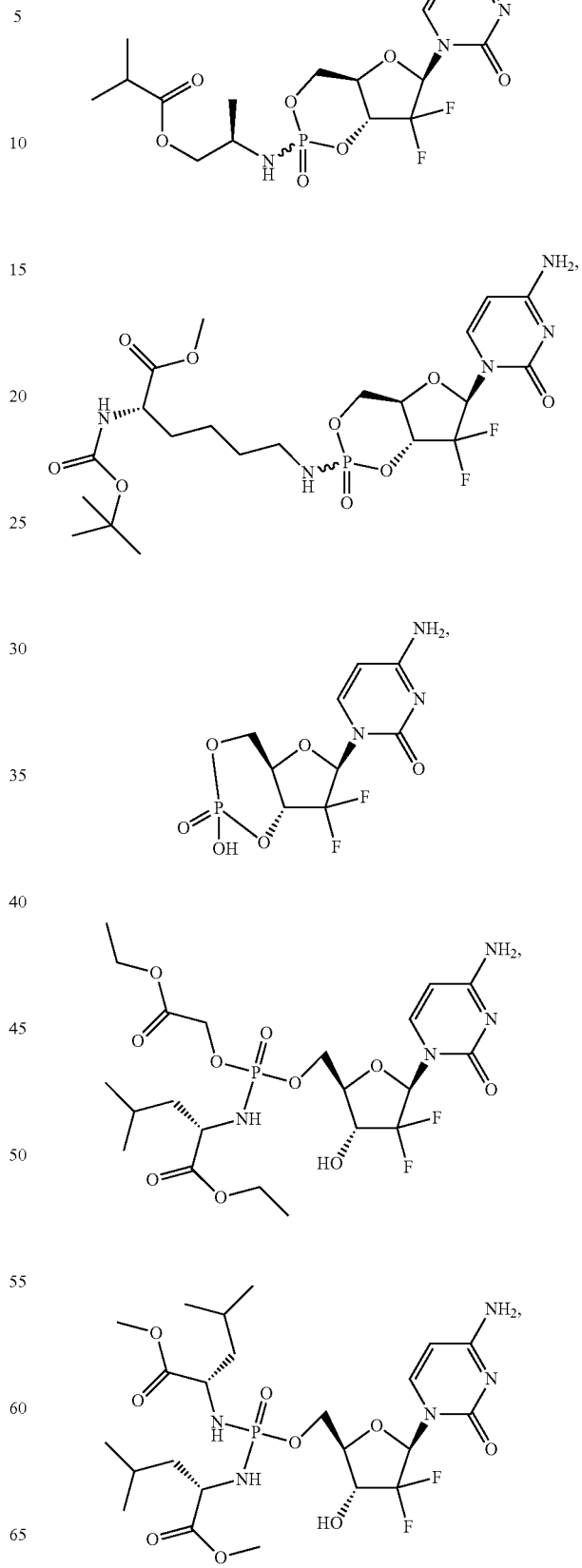

-continued
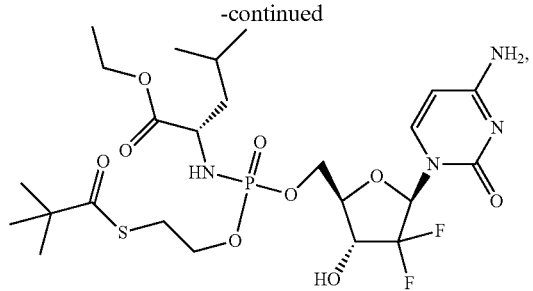
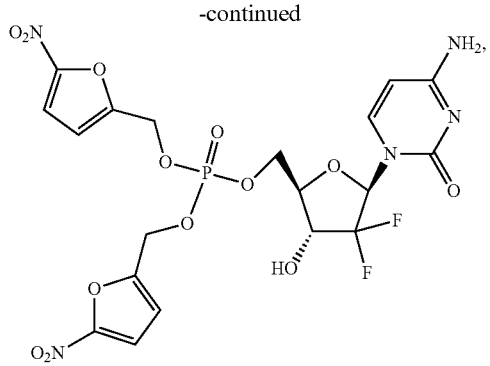
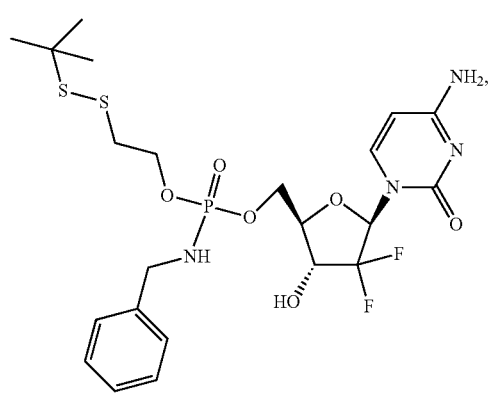
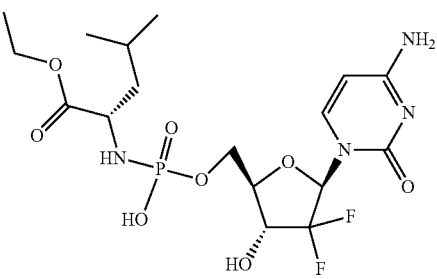
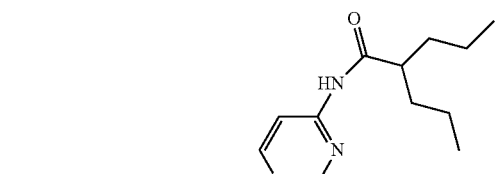
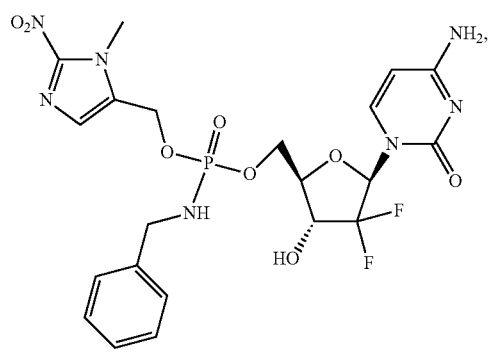
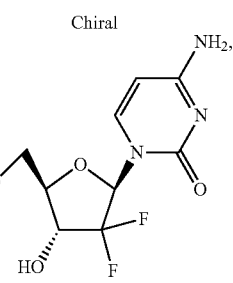
Chiral
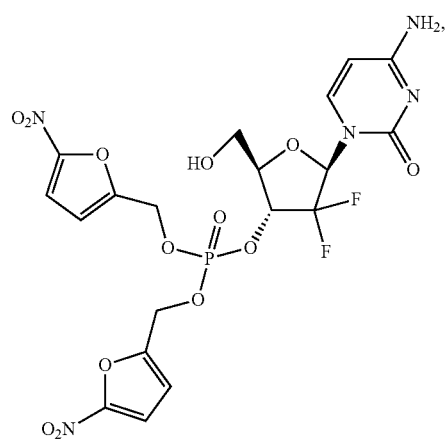
Chiral
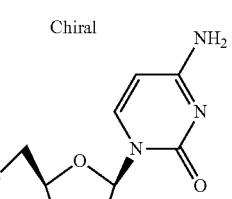
and

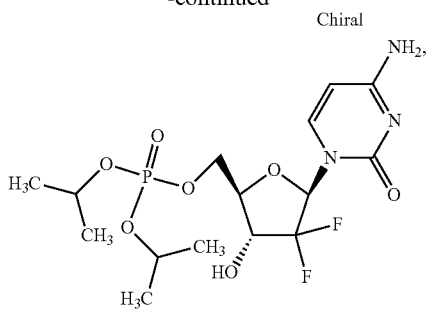
and pharmaceutically acceptable salts thereof.
In certain embodiments, provided herein are any of the following compounds:
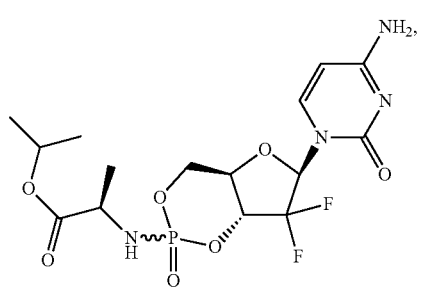
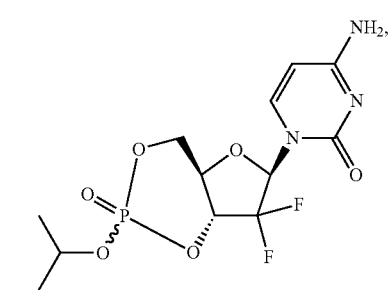
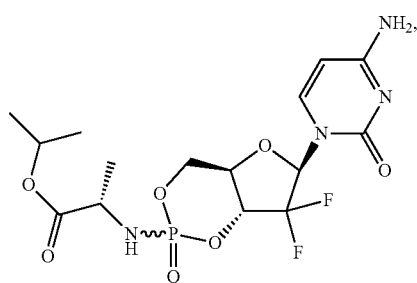
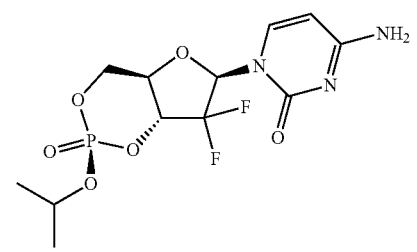
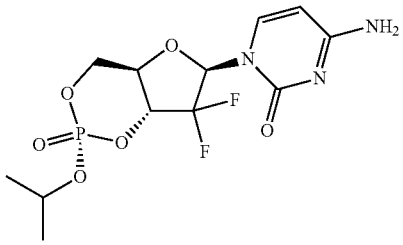
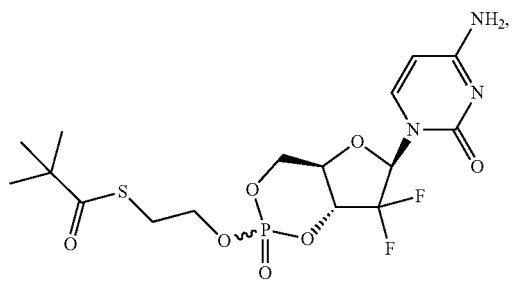
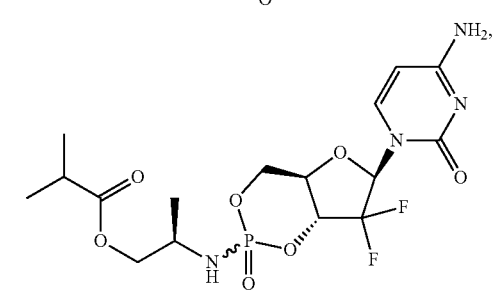
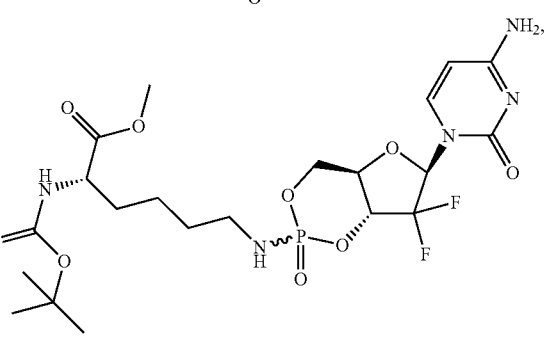
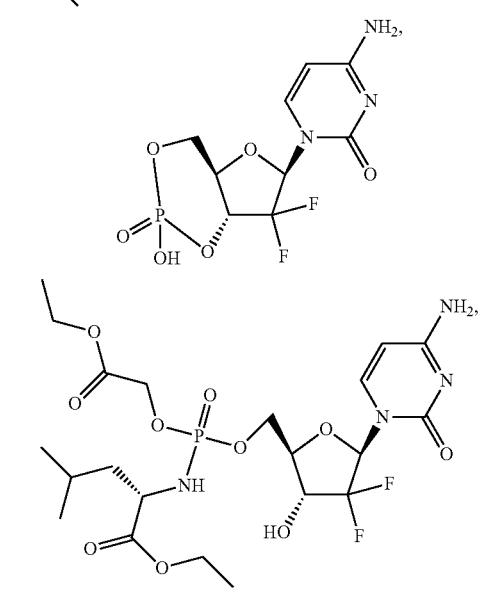

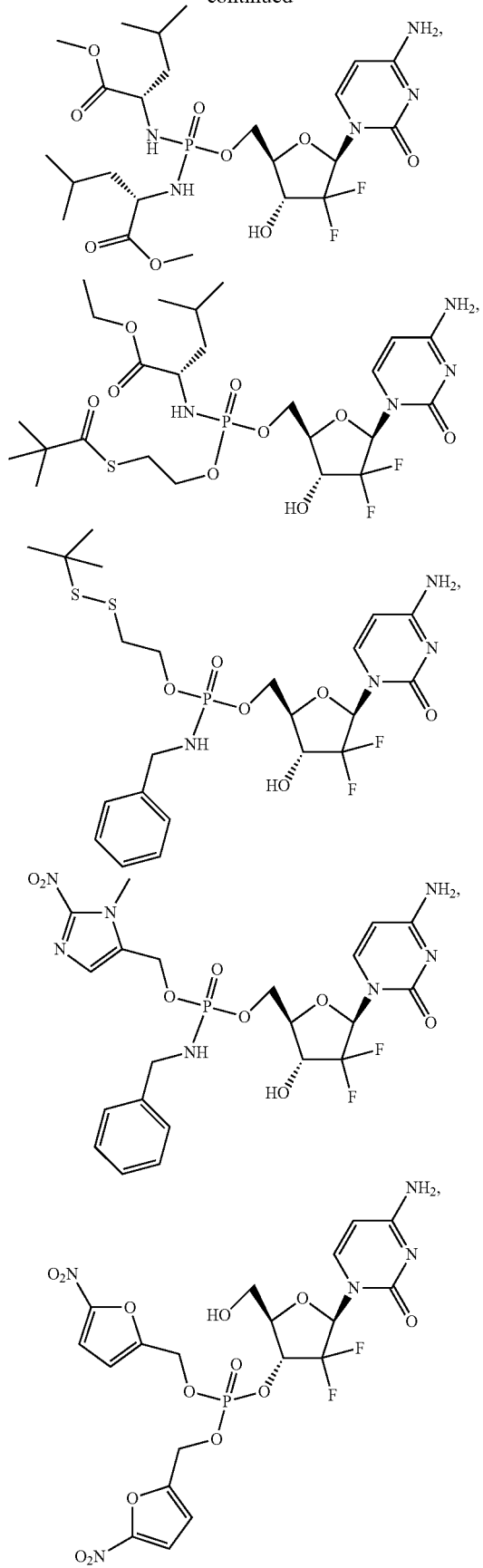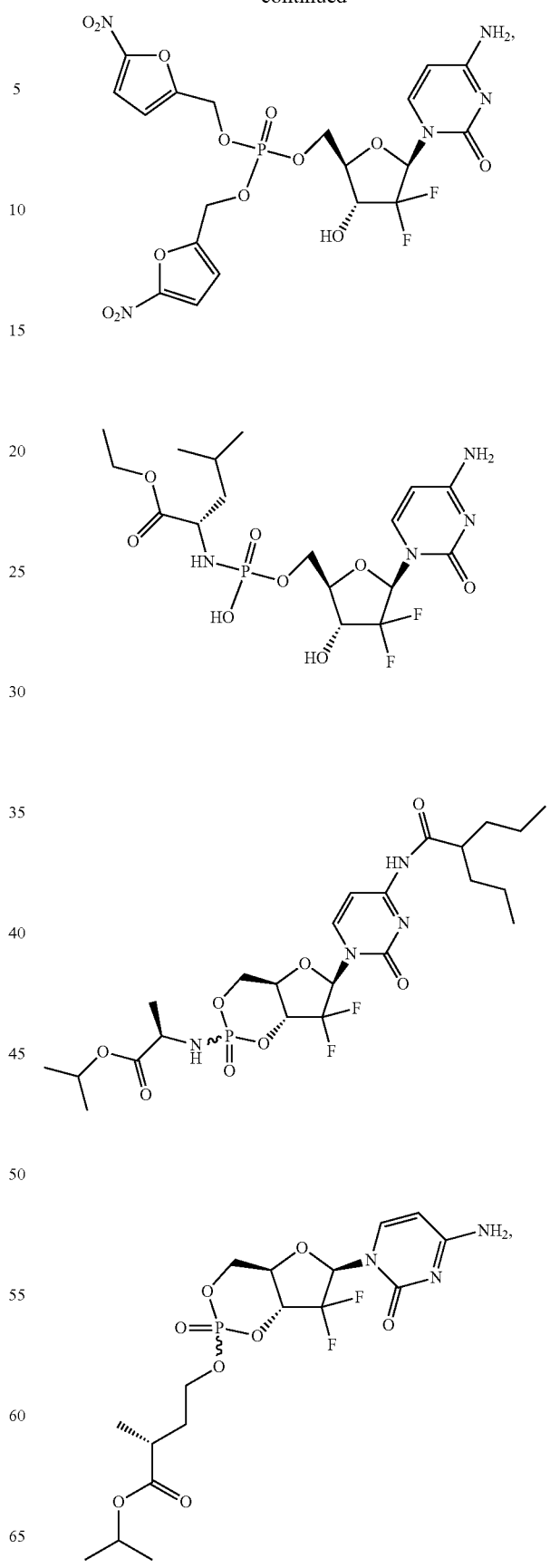

31
-continued
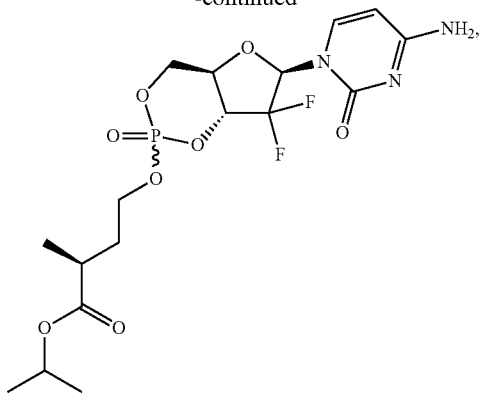
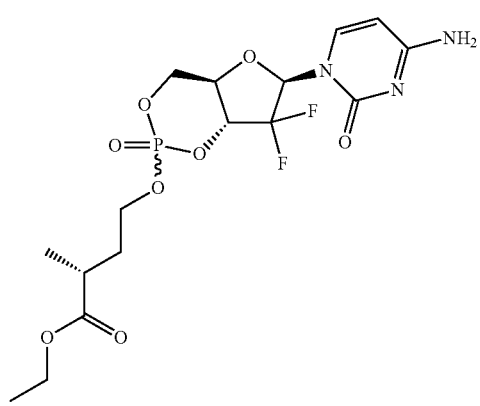
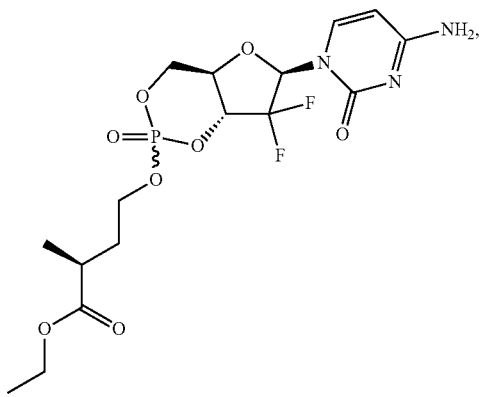
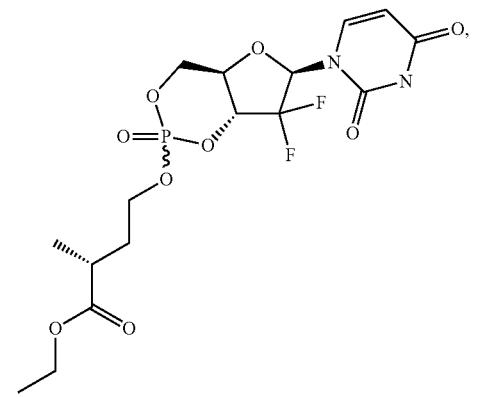
32
-continued
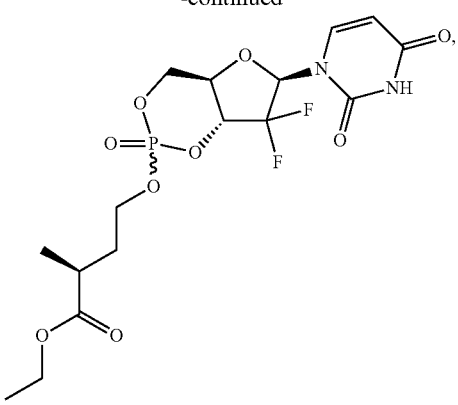
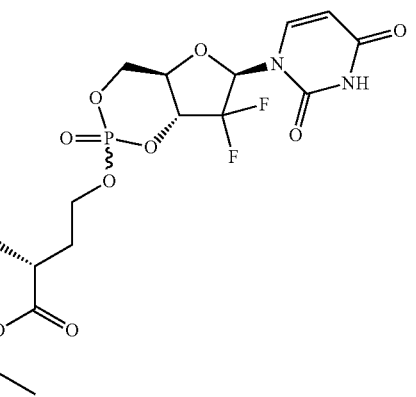
and
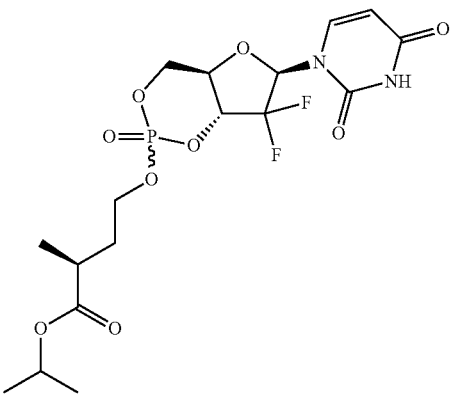
and pharmaceutically acceptable salts thereof.
In certain embodiments, provided herein are any of the following compounds:
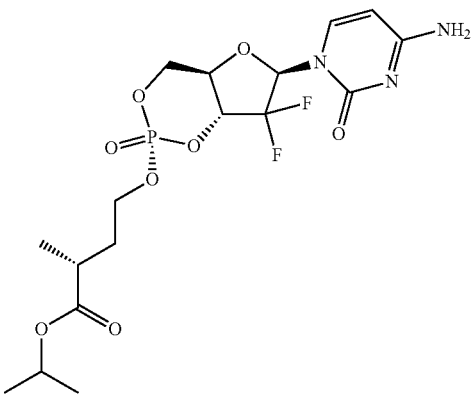

-continued

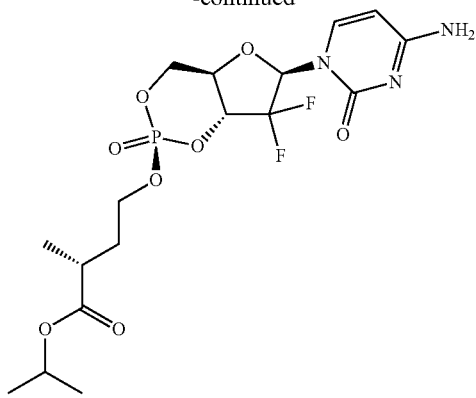

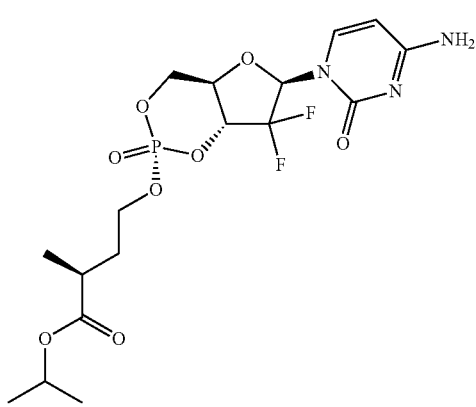

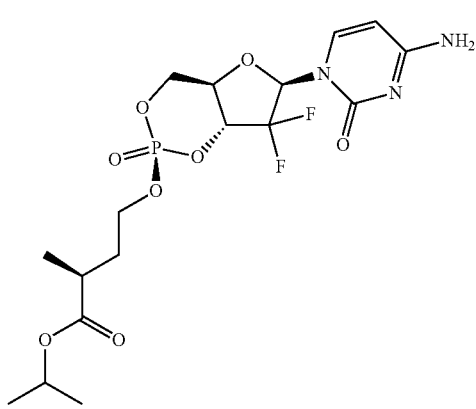

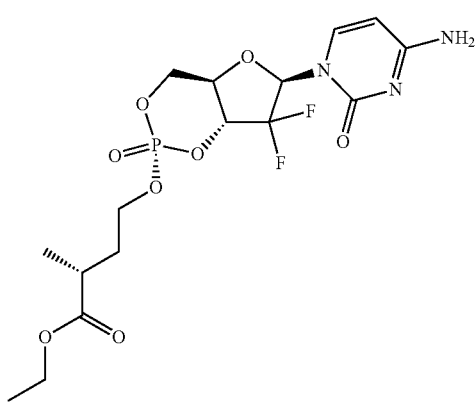

-continued

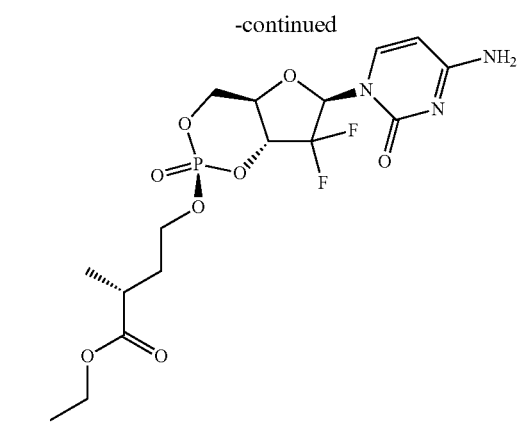

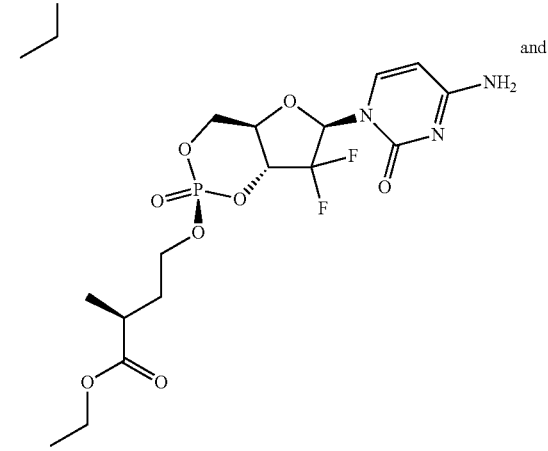

and and pharmaceutically acceptable salts thereof.

In some embodiments, provided herein are:

(a) compounds as described herein, e.g., of Formulas I-VI, or pharmaceutically acceptable salts and compositions thereof;

(b) compounds as described herein, e.g., of Formulas I-VI, or pharmaceutically acceptable salts and compositions thereof for use in therapy;

(c) compounds as described herein, e.g., of Formulas I-VI, or pharmaceutically acceptable salts and compositions thereof for use in the treatment and/or prophylaxis of a cancer, for example liver cancer, breast cancer, ovarian cancer, lung cancer, pancreatic cancer or leukemic cancer;

(d) processes for the preparation of compounds as described herein, e.g., of Formulas I-VI, as described in more detail elsewhere herein;

(e) pharmaceutical compositions comprising a compound as described herein, e.g., of Formulas I-VI, or a pharmaceutically acceptable salt thereof together with a pharmaceutically acceptable carrier or diluent;

(f) pharmaceutical formulations comprising a compound as described herein, e.g., of Formulas I-VI, or a pharmaceutically acceptable salt thereof together with one or more other effective therapeutic agents, e.g. anti-cancer agents, optionally in a pharmaceutically acceptable carrier or diluent;

(g) a method for the treatment and/or prophylaxis of a host with cancer, for example liver cancer, breast cancer, ovarian cancer, lung cancer, pancreatic cancer or leukemic cancer that includes the administration of an effective amount of a compound as described herein, e.g., of Formulas I-VI, its pharmaceutically acceptable salt or composition;

(h) a method for the treatment and/or prophylaxis of a host with cancer, for example liver cancer, breast cancer, ovarian cancer, lung cancer, pancreatic cancer or leukemic cancer that includes the administration of an effective amount of a compounds as described herein, e.g., of Formulas I-VI, its pharmaceutically acceptable salt or composition in combination and/or alternation with one or more other effective therapeutic agent, e.g. anti-cancer agent; or (i) combinations comprising compounds as described herein, e.g., of Formulas I-VI, or pharmaceutically acceptable salts, and one, two, three or more other therapeutic agents, e.g. anti-cancer agents.

Optically Active Compounds

It is appreciated that compounds provided herein have several chiral centers and may exist in and be isolated in optically active and racemic forms. Some compounds may exhibit polymorphism. It is to be understood that any racemic, optically-active, diastereomeric, polymorphic, or stereoisomeric form, or mixtures thereof, of a compound provided herein, which possess the useful properties described herein is within the scope of the invention. It being well known in the art how to prepare optically active forms (for example, by resolution of the racemic form by recrystallization techniques, by synthesis from optically-active starting materials, by chiral synthesis, or by chromatographic separation using a chiral stationary phase).

The compounds described herein, i.e. compounds of any of Formulas I-VI, may have one or more chiral (asymmetric) centers. The present disclosure encompasses all stereoisomeric forms of the compounds described herein. Centers of asymmetry that are present in the compounds described herein, can all independently of one another have (R) or (S) configuration. When bonds to a chiral atom, such as carbon or phosphorus, are depicted as straight lines in the structural formulas of the compounds described herein, or when a compound name is recited without an (R) or (S) chiral designation for a chiral atom, it is understood that both the (R) and (S) configurations of each such chiral atoms, and hence each enantiomer or diastereomer and mixtures thereof, are embraced within the structural formula or by the name. The production of specific stereoisomers or mixtures thereof may be identified in the Examples where such stereoisomers or mixtures were obtained, but this in no way limits the inclusion of all stereoisomers and mixtures thereof from being within the scope of the present disclosure.

Since the 1' and 4' carbons of a nucleoside are chiral, their non-hydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a non-naturally occurring β-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the non-naturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

a) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In some embodiments, provided is a composition that comprises a substantially pure designated enantiomer of a compound described herein. In certain embodiments, in the methods and compounds of this invention, the compounds are substantially free of other enantiomers. In some embodiments, a composition includes a compound that is at least 85%, 90%, 95%, 98%, 99% or 100% by weight, of the compound, the remainder comprising other chemical species or enantiomers.

In an embodiment, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound described herein, e.g., a compound of any of Formulas I-VI, or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopic analysis. The present invention includes all such isomers, as well as salts, solvates (which includes hydrates) and solvated salts of such racemates, enantiomers, diastereomers and tautomers and mixtures thereof.

Isotopically Enriched Compounds

Also provided herein are isotopically enriched compounds, including but not limited to isotopically enriched 5'-D-amino acid phosphoramidate compounds.

Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable ME that will affect the pharmacokinetic, pharmacologic, and/or toxicological profiles of a compound provided herein in comparison with a similar compound having a natural isotopic composition.

Preparation of Compounds

The compounds provided herein can be prepared, isolated or obtained by any method apparent to those of skill in the art. Compounds provided herein can be prepared according to the Exemplary Preparation Schemes provided below. Reaction conditions, steps and reactants not provided in the Exemplary Preparation Schemes would be apparent to, and known by, those skilled in the art.

SCHEME A

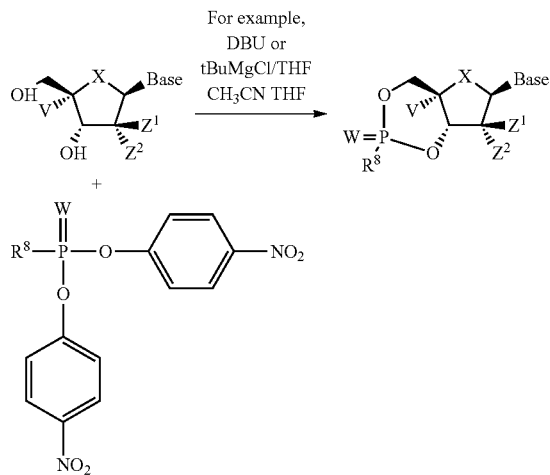

SCHEME B

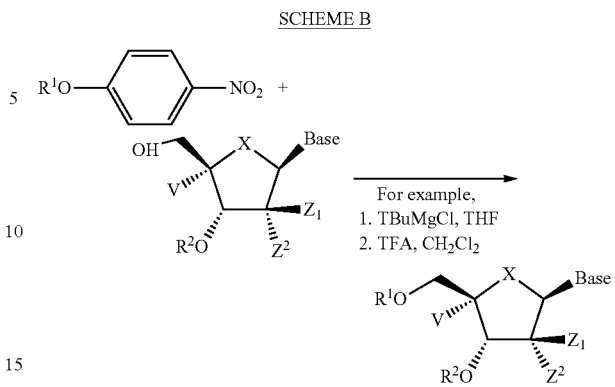

wherein one or both of $R^1$ and $R^2$ are hydrogen.

SCHEME C

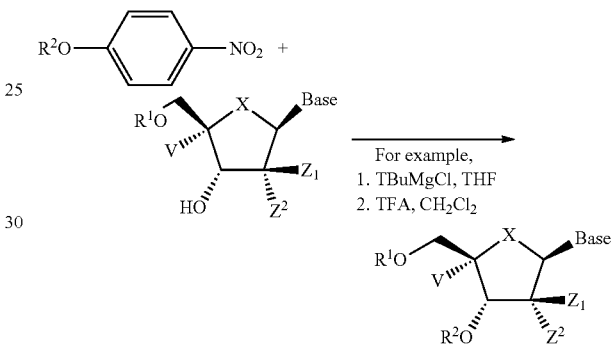

In the Exemplary Preparation Schemes, the variables are as described in the context of Formula I to VI. Nucleosides can be prepared or obtained according to the knowledge in the art. Additional steps and reagents not provided in the Exemplary Preparation Schemes would be known to those of skill in the art. Exemplary methods of preparation are described in detail in the Examples herein.

Pharmaceutical Compositions and Methods of Administration

Compounds described herein can be formulated into pharmaceutical compositions using methods available in the art and those disclosed herein. Any of the compounds disclosed herein can be provided in the appropriate pharmaceutical composition and be administered by a suitable route of administration.

The methods provided herein encompass administering pharmaceutical compositions containing at least one compound as described herein, including a compound of general Formulas I-VI, if appropriate in the salt form, either used alone or in the form of a combination with one or more compatible and pharmaceutically acceptable carriers, such as diluents or adjuvants, or with another anti-cancer agent.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately.

They can be packaged together, or packaged separately, for the convenience of the practitioner of skill in the art.

In clinical practice the active agents provided herein may be administered by any conventional route, in particular orally, parenterally, rectally or by inhalation (e.g. in the form of aerosols). In certain embodiments, the compound provided herein is administered orally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semisynthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, for example, an animal subject, such as a mammalian subject, for example, a human subject.

A pharmaceutical composition is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of liver cancer may contain larger amounts of one or more of the active ingredients it comprises than a dosage form used in the maintenance treatment of the same cancer. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington's Pharmaceutical Sciences, 20th ed., Mack Publishing, Easton Pa. (2000).

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound. Alternatively other doses can be used as described in British Journal of Cancer, 2002, 86, 1297-1302.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000).

In certain embodiments, the oral dosage forms are solid and prepared under anhydrous conditions with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gelcaps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In certain embodiments, a pump may be used (see, Sefton, *CRC Crit. Ref. Biomed. Eng.* 14:201 (1987); Buchwald et al., *Surgery* 88:507 (1980); Saudek et al., *N Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol.

2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, $16^{th}$, 18th and $20^{th}$ eds., Mack Publishing, Easton Pa. (1980, 1990 & 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, $16^{th}$, 18th and $20^{th}$ eds., Mack Publishing, Easton Pa. (1980, 1990 & 2000).

Depending on the specific tissue to be treated, additional components may be used prior to, in conjunction with, or subsequent to treatment with active ingredients provided. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the cancer and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating or preventing a liver cancer in a subject by administering, to a subject in need thereof, an effective amount of a compound provided herein, or a pharmaceutically acceptable salt thereof. The amount of the compound or composition which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the conditions described herein lie within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiment, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail herein. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

The dosages of the second agents are to be used in the combination therapies provided herein. In certain embodiments, dosages lower than those which have been or are currently being used to prevent or treat liver cancer are used in the combination therapies provided herein. The recommended dosages of second agents can be obtained from the knowledge of those of skill. For those second agents that are approved for clinical use, recommended dosages are described in, for example, Hardman et al., eds., 1996, Goodman & Gilman's The Pharmacological Basis Of Basis Of Therapeutics 9$^{th}$ Ed, Mc-Graw-Hill, New York; Physician's Desk Reference (PDR) 57$^{th}$ Ed., 2003, Medical Economics Co., Inc., Montvale, N.J., which are incorporated herein by reference in its entirety.

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, for example, a mammal, such as a human, in a sequence and within a time interval such that the compound provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In certain embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agents) for a period of time, followed by the administration of a second agent and/or third agent (e.g., a second and/or third prophylactic or therapeutic agents) for a period of time and repeating this sequential administration. Cycling therapy can reduce the development of resistance to one or more of the therapies, avoid or reduce the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In certain embodiments, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of a cancer, for example liver cancer, breast cancer, ovarian cancer, lung cancer, pancreatic cancer or leukemic cancer such as hepatocellular carcinoma, cholangiocarcinoma, or biliary tract cancer. In certain embodiments, the cancer is breast cancer, ovarian cancer, lung cancer, pancreatic cancer or leukemic cancer. The kits can include a compound or composition provided herein, a second agent or composition, and instructions providing information to a health care provider regarding usage for treating the disorder. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

In one embodiment is a compound or a pharmaceutically acceptable salt, solvate, stereoisomeric form, tautomeric form or polymorphic form thereof for use in therapy.

Provided herein is a method for treating cancer in a subject, which comprises contacting the subject with a therapeutically effective amount of a nucleotide analog disclosed herein, e.g., a compound of Formulas I-VI, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof. In certain embodiments, the cancer is selected from liver cancer, breast cancer, ovarian cancer, lung cancer, pancreatic cancer or leukemic cancer. In an embodiment the cancer is liver cancer. Liver cancers which can be treated include primary and secondary liver cancers. In particular embodiments, the liver cancer is hepatocellular carcinoma, cholangiocarcinoma, or biliary tract cancer. In particular embodiments, the liver cancer is a metastasis in the liver originated from other cancers (such as colon cancer, pancreatic cancer, etc.).

Provided herein is a method for inhibiting the growth of a cancer cell, which comprises contacting the cell with a therapeutically effective amount of a compound disclosed herein, e.g., a compound of Formulas I-VI, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof. In certain embodiments, the cancer is selected from liver cancer, breast cancer, ovarian cancer, lung cancer, pancreatic cancer or leukemic cancer. In an embodiment the cancer is liver cancer. In certain embodiments, the liver cancer is hepatocellular carcinoma, cholangiocarcinoma, or biliary tract cancer. In particular embodiments, the cancer is hepatocellular carcinoma.

Provided herein is a method for inhibiting replication of a cancer cell, which comprises contacting the cell with a therapeutically effective amount of a compound disclosed herein, e.g., a compound of Formulas I-VI, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof. In certain embodiments, the cancer is selected from liver cancer, breast cancer, ovarian cancer, lung cancer, pancreatic cancer or leukemic cancer. In an embodiment the cancer is liver cancer. In certain embodiments, the liver cancer is hepatocellular carcinoma, cholangiocarcinoma, or biliary tract cancer. In particular embodiments, the cancer is hepatocellular carcinoma.

Provided herein is a method for inhibiting the growth of a tumor, which comprises contacting the tumor with a compound disclosed herein, e.g., a compound of Formulas I-VI, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof. In certain embodiments, the tumor is selected from a liver tumor, breast tumor, ovarian tumor, lung tumor, pancreatic tumor or leukemic tumor. In an embodiment the tumor is liver tumor. In certain embodiments, the liver tumor is hepatocellular carcinoma, cholangiocarcinoma, or biliary tract cancer. In particular embodiments, the tumor is hepatocellular carcinoma.

In certain embodiments, provided herein are methods for the treatment and/or prophylaxis of a subject with cancer that includes the administration of an effective amount of a nucleoside compound disclosed herein, e.g., a nucleoside compound of Formulas I-VI, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof. In certain embodiments, the cancer is selected from liver cancer, breast cancer, ovarian cancer, lung cancer, pancreatic cancer or leukemic cancer. In an embodiment the cancer is liver cancer. In certain embodiments, the liver cancer is hepatocellular carcinoma, cholangiocarcinoma, or biliary tract cancer. In particular embodiments, the cancer is hepatocellular carcinoma.

In certain embodiments, provided herein are methods for treating a cancer in a subject. In certain embodiments, the methods encompass the step of administering to the subject in need thereof an amount of a compound effective for the treatment or prevention of a cancer in combination with a second agent effective for the treatment or prevention of the cancer. The compound can be any compound as described herein, and the second agent can be any second agent described in the art or herein. In certain embodiments, the compound is in the form of a pharmaceutical composition or dosage form, as described elsewhere herein. In certain embodiments, the cancer is selected from liver cancer, breast cancer, ovarian cancer, lung cancer, pancreatic cancer or leukemic cancer. In an embodiment the cancer is liver cancer. In certain embodiments, the liver cancer is hepatocellular carcinoma, cholangiocarcinoma, or biliary tract cancer. In particular embodiments, the cancer is hepatocellular carcinoma.

In certain embodiments, provided herein are methods for the treatment and/or prophylaxis of a subject with cancer that includes the administration of an effective amount of a compounds provided herein, or a pharmaceutically acceptable salt thereof. In certain embodiments, provided herein are methods for treating a cancer in a subject. In certain embodiments, the methods encompass the step of administering to the subject in need thereof an amount of a compound effective for the treatment or prevention of a cancer in combination with a second agent effective for the treatment or prevention of the cancer. The compound can be any compound as described herein, and the second agent can be any second agent described in the art or herein. In certain embodiments, the compound is in the form of a pharmaceutical composition or dosage form, as described elsewhere herein. In certain embodiments, the cancer is selected from liver cancer, breast cancer, ovarian cancer, lung cancer, pancreatic cancer or leukemic cancer. In an embodiment the cancer is liver cancer. In certain embodiments, the liver cancer is hepatocellular carcinoma, cholangiocarcinoma, or biliary tract cancer. In particular embodiments, the cancer is hepatocellular carcinoma.

In an embodiment, the cancers which can be treated by the compounds described herein include, but are not limited to, Acute Lymphoblastic Leukemia; Acute Myeloid Leukemia; Adrenocortical Carcinoma; AIDS-Related Lymphoma; AIDS-Related Malignancies; Anal Cancer; Astrocytoma; Bile Duct Cancer; Bladder Cancer; Bone Cancer, Osteosarcoma/Malignant Fibrous Histiocytoma; Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer; Bronchial Adenomas/Carcinoids; Carcinoid Tumor; Carcinoid Tumor, Gastrointestinal; Carcinoma, Adrenocortical; Carcinoma, Islet Cell; Central Nervous System Lymphoma, Primary; Cerebral Astrocytoma/Malignant Glioma; Cervical Cancer; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer; Cutaneous T-Cell Lymphoma; Endometrial Cancer; Ependymoma; Epithelial Cancer, Ovarian; Esophageal Cancer; Esophageal Cancer; Ewing's Family of Tumors; Extracranial Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer; Hodgkin's Lymphoma; Hypopharyngeal Cancer; Hypothalamic and Visual Pathway Glioma; Intraocular Melanoma; Islet Cell Carcinoma (Endocrine Pancreas); Kaposi's Sarcoma; Kidney Cancer; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoblastic Leukemia; Lymphoma, AIDS-Related; Lymphoma, Central Nervous System (Primary); Lymphoma, Cutaneous T-Cell; Lymphoma, Hodgkin's; Lymphoma, Hodgkin's During Pregnancy; Lymphoma, Non-Hodgkin's; Lymphoma, Primary Central Nervous System; Macroglobulinemia, Waldenstrom's; Male Breast Cancer; Malignant Mesothelioma; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Small Cell Lung Cancer; Oral Cancer; Oral Cavity and Lip Cancer; Oropharyngeal Cancer; steosarcoma/Malignant Fibrous Histiocytoma of Bone; Ovarian Epithelial Cancer; Ovarian Germ Cell Tumor; Ovarian Low Malignant Potential Tumor; Pancreatic Cancer; Paranasal Sinus and Nasal Cavity Cancer; Parathyroid Cancer; Penile Cancer; Pheochromocytoma; Pineal and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer; Prostate Cancer; Rectal Cancer; Renal Cell (Kidney) Cancer; Renal Pelvis and Ureter, Transitional Cell Cancer; Retinoblastoma; Rhabdomyosarcoma; Salivary Gland Cancer; Sarcoma, Ewing's Family of Tumors; Sarcoma, Kaposi's; Sarcoma (Osteosarcoma)/Malignant Fibrous Histiocytoma of Bone; Sarcoma, Soft Tissue; Sezary Syndrome; Skin Cancer; Skin Cancer (Melanoma); Skin Carcinoma, Merkel Cell; Small Cell Lung Cancer; Small Intestine Cancer; Soft Tissue Sarcoma; Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Thymoma, Malignant; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Sarcoma; Vaginal Cancer; Visual Pathway and Hypothalamic Glioma; Vulvar Cancer; Waldenstrom's Macro globulinemia; and Wilms' Tumor.

In one embodiment, a cancer potentially associated with mutant IDH enzyme activity is brain cancer, such as an astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, meatypical meningioma, anaplastic meningioma; and pituitary adenoma. In another embodiment, the brain cancer is glioma, glioblastoma multiforme, paraganglioma, or suprantentorial primordial neuroectodermal tumors (sPNET).

In another embodiment, a cancer potentially associated with mutant IDH enzyme activity is leukemia, such as acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma and acute lymphoblastic leukemia.

In one embodiment, a cancer potentially associated with mutant IDH enzyme activity is skin cancer, including melanoma. In another embodiment, a cancer potentially associated with mutant IDH enzyme activity is prostate cancer, breast cancer, thyroid cancer, colon cancer, or lung cancer. In another embodiment, a cancer potentially associated with mutant IDH enzyme activity is sarcoma, including central chondrosarcoma, central and periosteal chondroma, and fibrosarcoma. In another embodiment, a cancer potentially associated with mutant IDH enzyme activity is cholangiocarcinoma.

In certain embodiments, the compounds described herein can be used to treat a proliferative disease, for example a carcinoma, including, but not limited to, Kit-mediated carcinomas, adenocarcinoma, squamous cell carcinoma, adenosquamous carcinoma, teratocarcinoma, head and neck cancer, brain cancer, intracranial carcinoma, glioblastoma (including PDGFR-mediated glioblastoma), glioblastoma multiforme (including PDGFR-mediated glioblastoma multiforme), neuroblastoma, cancer of the larynx, multiple endocrine neoplasias 2A and 2B (MENS 2A and MENS 2B) (including RET-mediated MENS), thyroid cancer (including sporadic and familial medullary thyroid carcinoma), papillary thyroid carcinoma, parathyroid carcinoma (including any RET-mediated thyroid carcinoma), follicular thyroid cancer, anaplastic thyroid cancer, bronchial carcinoid, oat cell carcinoma, lung cancer, small-cell lung cancer (including FLT3 and/or Kit-mediated small cell lung cancer), non-small-cell lung cancer, stomach/gastric cancer, gastrointestinal cancer, gastrointestinal stromal tumors (GIST) (including Kit-mediated GIST and PDGFR α-mediated GIST), colon cancer, colorectal cancer, pancreatic cancer, islet cell carcinoma, hepatic/liver cancer, metastases to the liver, bladder cancer, renal cell cancer (including PDGFR-mediated renal cell cancer), cancers of the genitourinary tract, ovarian cancer (including Kit-mediated and/or PDGFR-mediated ovarian cancer), endometrial cancer (including CSF-1R-mediated endometrial cancer), cervical cancer, breast cancer (including FLT3-mediated and/or PDGFR-mediated breast cancer), prostate cancer (including Kit-mediated prostate cancer), germ cell tumors (including Kit-mediated germ cell tumors), seminomas (including Kit-mediated seminomas), dysgerminomas (including Kit-mediated dysgerminomas), melanoma (including PDGFR-mediated melanoma), metastases to the bone (including CSF-1R-mediated bone metastases), metastatic tumors (including VEGFR-mediated tumors), stromal tumors, neuroendocrine tumors, tumor angiogenesis (including VEGFR-mediated tumor angiogenesis), and mixed mesodermal tumors.

In certain embodiments, the proliferative disease is sarcomas, including, but not limited to, PDGFR-mediated sarcomas, osteosarcoma, osteogenic sarcoma, bone cancer, glioma (including PDGFR-mediated and/or CSF-1R-mediated glioma), astrocytoma, vascular tumors (including VEGFR-mediated vascular tumors), Kaposi's sarcoma, carcinosarcoma, hemangiosarcomas (including VEGFR3-mediated hemangiosarcomas), and lymphangiosarcoma (including VEGFR3-mediated lymphangiosarcoma).

In certain embodiments, the proliferative disease is a hematologic malignancy. In certain embodiments, the proliferative disease is a relapsed hematologic malignancy. In certain embodiments, the proliferative disease is a refractory hematologic malignancy. In certain embodiments, the proliferative disease is a drug-resistant hematologic malignancy. In certain embodiments, the proliferative disease is a multidrug-resistant hematologic malignancy. In certain embodiments, the proliferative disease is a Bcr-Abl kinase inhibitor-resistant hematologic malignancy. In certain embodiments, the proliferative disease is an imatinib-resistant hematologic malignancy. In certain embodiments, the proliferative disease is a dasatinib-resistant hematologic malignancy. In certain embodiments, the proliferative disease is a nilatinib-resistant hematologic malignancy. In certain embodiments, the proliferative disease is a bosutinib-resistant hematologic malignancy. In certain embodiments, the proliferative disease is a cytarabine-resistant hematologic malignancy.

In certain embodiments, the hematologic malignancy is myeloma, leukemia, myeloproliferative diseases, acute myeloid leukemia (AML) (including FLT3 mediated and/or KIT-mediated and/or CSF1R-mediated acute myeloid leukemia), chronic myeloid leukemias (CML) (including FLT3-mediated and/or PDGFR-mediated chronic myeloid leukemia), myelodysplastic leukemias (including FLT3-mediated myelodysplastic leukemia), myelodysplastic syndrome (including FLT3 mediated and/or Kit-mediated myelodysplastic syndrome), idiopathic hypereosinophilic syndrome (HES) (including PDGFR-mediated HES), chronic eosinophilic leukemia (CEL) (including PDGFR-mediated CEL), chronic myelomonocytic leukemia (CMML), mast cell leukemia (including Kit-mediated mast cell leukemia), or systemic mastocytosis (including Kit-mediated systemic mastocytosis).

In certain embodiments, the hematologic malignancy is lymphoma, lymphoproliferative diseases, acute lymphoblastic leukemia (ALL), B-cell acute lymphoblastic leukemias, T-cell acute lymphoblastic leukemias, chronic lymphocytic leukemia (CLL), natural killer (NK) cell leukemia, B-cell lymphoma, T-cell lymphoma, or natural killer (NK) cell lymphoma.

In an embodiment, the hematologic malignancy is myelodysplastic syndrome (MDS).

In certain embodiments, the hematologic malignancy is Langerhans cell histiocytosis (including CSF-1R-mediated and/or FLT3-mediated Langerhans cell histiocytosis), mast cell tumors, or mastocytosis.

In certain embodiments, the hematologic malignancy is leukemia. In certain embodiments, the hematologic malignancy is relapsed leukemia. In certain embodiments, the hematologic malignancy is refractory leukemia. In certain embodiments, the hematologic malignancy is drug-resistant leukemia. In certain embodiments, the hematologic malignancy is multidrug-resistant leukemia. In certain embodiments, the hematologic malignancy is a Bcr-Abl kinase inhibitor-resistant leukemia. In certain embodiments, the hematologic malignancy is imatinib-resistant leukemia. In certain embodiments, the hematologic malignancy is dasatinib-resistant leukemia. In certain embodiments, the hematologic malignancy is nilatinib-resistant leukemia. In certain embodiments, the hematologic malignancy is bosutinib-resistant leukemia.

In certain embodiments, the hematologic malignancy is cytarabine-resistant leukemia.

In certain embodiments, the leukemia is acute leukemia. In certain embodiments, the leukemia is relapsed acute leukemia. In certain embodiments, the leukemia is refractory acute leukemia. In certain embodiments, the leukemia is drug-resistant acute leukemia. In certain embodiments, the leukemia is multidrug-resistant acute leukemia. In certain embodiments, the leukemia is a Bcr-Abl kinase inhibitor-resistant acute leukemia. In certain embodiments, the leukemia is imatinib-resistant acute leukemia. In certain embodiments, the leukemia is dasatinib-resistant acute leukemia. In certain embodiments, the leukemia is nilatinib-resistant acute leukemia. In certain embodiments, the leukemia is bosutinib-resistant acute leukemia. In certain embodiments, the leukemia is cytarabine-resistant acute leukemia. In certain embodiments, the leukemia is a hereditary leukemia. In certain embodiments, the hereditary leukemia is severe congenital neutropenia (SCN). In certain embodiments, the hereditary leukemia is familial platelet disorder with acute myelogenous leukemia (FDP/AML). In certain embodiments, the leukemia is caused by LEF1. In certain embodiments, the leukemia is mediated by LEF1. In certain embodiments, the leukemia is caused by GSK3.

In certain embodiments, the leukemia is ALL. In certain embodiments, the leukemia is relapsed ALL. In certain embodiments, the leukemia is refractory ALL. In certain embodiments, the leukemia is drug-resistant ALL. In certain embodiments, the leukemia is multidrug-resistant ALL. In certain embodiments, the leukemia is a Bcr-Abl kinase inhibitor-resistant ALL. In certain embodiments, the leukemia is imatinib-resistant ALL. In certain embodiments, the leukemia is dasatinib-resistant ALL. In certain embodiments, the leukemia is nilatinib-resistant ALL. In certain embodiments, the leukemia is bosutinib-resistant ALL. In certain embodiments, the leukemia is cytarabine-resistant ALL.

In one embodiment, ALL is leukemia that originates in the blast cells of the bone marrow (B-cells), thymus (T-cells), or lymph nodes. ALL is categorized according to the French-American-British (FAB) Morphological Classification Scheme as L1-mature-appearing lymphoblasts (T-cells or pre-B-cells), L2-immature and pleomorphic (variously shaped) lymphoblasts (T-cells or pre-B-cells), and L3-lymphoblasts (B-cells; Burkitt's cells). In another embodiment, ALL originates in the blast cells of the bone marrow (B-cells). In yet another embodiment, ALL originates in the thymus (T-cells). In yet another embodiment, ALL originates in the lymph nodes. In yet another embodiment, ALL is L1 type characterized by mature-appearing lymphoblasts (T-cells or pre-B-cells). In yet another embodiment, ALL is L2 type characterized by immature and pleomorphic (variously shaped) lymphoblasts (T-cells or pre-B-cells). In still another embodiment, ALL is L3 type characterized by lymphoblasts (B-cells; Burkitt's cells).

In certain embodiments, the leukemia is AML. In certain embodiments, the leukemia is relapsed AML. In certain embodiments, the leukemia is refractory AML. In certain embodiments, the leukemia is drug-resistant AML. In certain embodiments, the leukemia is multidrug-resistant AML. In certain embodiments, the leukemia is a Bcr-Abl kinase inhibitor-resistant AML. In certain embodiments, the leukemia is imatinib-resistant AML. In certain embodiments, the leukemia is dasatinib-resistant AML. In certain embodiments, the leukemia is nilatinib-resistant AML. In certain embodiments, the leukemia is bosutinib-resistant AML. In certain embodiments, the leukemia is cytarabine-resistant AML. In certain embodiments, AML has a RAS mutation. In certain embodiments, the RAS mutation is NRAS, KRAS, or HRAS. In certain embodiments, the RAS mutation is NRAS. In certain embodiments, the RAS mutation is KRAS. In certain embodiments, the RAS mutation is HRAS.

In certain embodiments, AML is undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In one embodiment, AML is undifferentiated AML (M0). In another embodiment, AML is myeloblastic leukemia (M1). In yet another embodiment, AML is myeloblastic leukemia (M2). In yet another embodiment, AML is promyelocytic leukemia (M3 or M3 variant [M3V]). In yet another embodiment, AML is myelomonocytic leukemia (M4 or M4 variant with eosinophilia [M4E]). In yet another embodiment, AML is monocytic leukemia (M5). In yet another embodiment, AML is erythroleukemia (M6). In still another embodiment, AML is megakaryoblastic leukemia (M7). In certain embodiments, the leukemia is chronic leukemia. In certain embodiments, the leukemia is relapsed chronic leukemia. In certain embodiments, the leukemia is refractory chronic leukemia. In certain embodiments, the leukemia is drug-resistant chronic leukemia. In certain embodiments, the leukemia is multidrug-resistant chronic leukemia. In certain embodiments, the leukemia is a Bcr-Abl kinase inhibitor-resistant chronic leukemia. In certain embodiments, the leukemia is imatinib-resistant chronic leukemia. In certain embodiments, the leukemia is dasatinib-resistant chronic leukemia. In certain embodiments, the leukemia is nilatinib-resistant chronic leukemia. In certain embodiments, the leukemia is bosutinib-resistant chronic leukemia. In certain embodiments, the leukemia is cytarabine-resistant chronic leukemia.

In certain embodiments, the leukemia is CLL. In certain embodiments, the leukemia is relapsed CLL. In certain embodiments, the leukemia is refractory CLL. In certain embodiments, the leukemia is drug-resistant CLL. In certain embodiments, the leukemia is multidrug-resistant CLL. In certain embodiments, the leukemia is a Bcr-Abl kinase inhibitor-resistant CLL. In certain embodiments, the leukemia is imatinib-resistant CLL. In certain embodiments, the leukemia is dasatinib-resistant CLL. In certain embodiments, the leukemia is nilatinib-resistant CLL. In certain embodiments, the leukemia is bosutinib-resistant CLL. In certain embodiments, the leukemia is cytarabine-resistant CLL.

In certain embodiments, the leukemia is CML. In certain embodiments, the leukemia is relapsed CML. In certain embodiments, the leukemia is refractory CML. In certain embodiments, the leukemia is drug-resistant CML. In certain embodiments, the leukemia is multidrug-resistant CML. In certain embodiments, the leukemia is a Bcr-Abl kinase inhibitor-resistant CML. In certain embodiments, the leukemia is imatinib-resistant CML. In certain embodiments, the leukemia is dasatinib-resistant CML. In certain embodiments, the leukemia is nilatinib-resistant CML. In certain embodiments, the leukemia is bosutinib-resistant CML. In certain embodiments, the leukemia is cytarabine-resistant CML. In certain embodiments, the leukemia is juvenile CML. In certain embodiments, the leukemia is juvenile CML with one or more NF-1 mutations.

In certain embodiments, the leukemia is T-cell leukemia. In one embodiment, the T-cell leukemia is peripheral T-cell leukemia, T-cell lymphoblastic leukemia, cutaneous T-cell leukemia, and adult T-cell leukemia. In another embodiment, the T-cell leukemia is peripheral T-cell leukemia. In yet another embodiment, the T-cell leukemia is T-cell lymphoblastic leukemia. In yet another embodiment, the T-cell leukemia is cutaneous T-cell leukemia. In still another embodiment, the T-cell leukemia is adult T-cell leukemia.

In certain embodiments, the leukemia is Philadelphia positive. In one embodiment, the Philadelphia positive leukemia is Philadelphia positive AML, including, but not limited to, undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the Philadelphia positive leukemia is Philadelphia positive ALL.

In certain embodiments, the proliferative disease is cancer, including, but not limited to, head and neck cancer (originating lip, oral cavity, oropharynx, hypopharynx, larynx, nasopharynx, nasal cavity, paranasal sinuses, or salivary glands), lung cancer (including small cell lung cancer and non-small cell lung cancer), gastrointestinal tract cancers (including esophageal cancer), gastric cancer, colorectal cancer, anal cancer, pancreatic cancer, liver cancer, gallbladder cancer, extrahepatic bile duct cancer, cancer of the ampulla of vater, breast cancer, gynecologic cancers (including cancer of uterine cervix), cancer of the uterine body, vaginal cancer, vulvar cancer, ovarian cancer, gestational trophoblastic cancer neoplasia, testicular cancer, urinary tract cancers (including renal cancer), urinary bladder cancer, prostate cancer, penile cancer, urethral cancer, neurologic tumors, endocrine neoplasms (including carcinoid and islet cell tumors), pheochromocytoma, adrenal cortical carcinoma, parathyroid carcinoma, and metastases to endocrine glands.

Further examples of cancers are basal cell carcinoma, squamous cell carcinoma, chondrosarcoma (a cancer arising in cartilage cells), mesenchymal-chondrosarcoma, soft tissue sarcomas (including malignant tumors that may arise in any of the mesodermal tissues (muscles, tendons, vessels that carry blood or lymph, joints and fat)), soft tissue sarcomas (include alveolar soft-part sarcoma), angiosarcoma, fibrosarcoma, leiomyosarcoma, liposarcoma, malignant fibrous histiocytoma, hemangiopericytoma, mesenchymoma, schwannoma, peripheral neuroectodermal tumours, rhabdomyosarcoma, synovial sarcoma, gestational trophoblastic tumor (malignancy in which the tissues formed in the uterus following conception become cancerous), Hodgkin's lymphoma, and laryngeal cancer.

In certain embodiments, the proliferative disease is a nonmalignant proliferation disease, including, but not limited to, atherosclerosis (including PDGFR-mediated atherosclerosis), restenosis following vascular angioplasty (including PDGFR-mediated restenosis), and fibroproliferative disorders (including obliterative bronchiolitis and idiopathic myelofibrosis).

In certain embodiments, the proliferative disease is an inflammatory disease or disorder related to immune dysfunction, immunodeficiency, or immunomodulation, including, but not limited to, autoimmune diseases, tissue transplant rejection, graft-versus-host disease, wound healing, kidney disease, multiple sclerosis, thyroiditis, type 1 diabetes, sarcoidosis, allergic rhinitis, inflammatory bowel diseases (including Crohn's disease and ulcerative colitis (UC)), systemic lupus erythematosis (SLE), arthritis, osteoarthritis, rheumatoid arthritis, osteoporosis, asthma, and chronic obstructive pulmonary disease (COPD).

In certain embodiments, the proliferative disease is an infectious disease. In certain embodiments, the infectious disease is fungal infection. In certain embodiments, the infectious disease is a superficial mycose (e.g., Tinea *versicolor*). In certain embodiments, the infectious disease is a cutaneous mycose (e.g., epidermis). In certain embodiments, the infectious disease is a subcutaneous mycose. In certain embodiments, the infectious disease is a systemic mycose.

In certain embodiments, the proliferative disease is leukemia, adult T-cell leukemia, promyelocytic leukemia, pre-B cell leukemia, lymphoma, Mantle cell lymphoma, breast cancer, pancreatic cancer, prostate cancer, head and neck cancer, ovarian cancer, melanoma, giloma, liver cancer, renal cancer, colorectal cancer, rhabdomyosarcoma, tongue cancer, stomach cancer, multiple myeloma, bladder cancer, thyroid cancer, epidermoid carcinoma, lung cancer, NSC lung cancer, or large cell lung cancer.

In certain embodiments, the proliferative disease is adult T-cell leukemia, promyelocytic leukemia, pre-B cell leukemia, lymphoma, mantle cell lymphoma, pancreatic cancer, prostate cancer, head and neck cancer, ovarian cancer, melanoma, giloma, liver cancer, renal cancer, colorectal cancer, rhabdomyosarcoma, tongue cancer, stomach cancer, multiple myeloma, bladder cancer, thyroid cancer, epidermoid carcinoma, NSC lung cancer, or large cell lung cancer.

In certain embodiments, the proliferative disease is leukemia, adult T-cell leukemia, promyelocytic leukemia, pre-B cell leukemia, lymphoma, mantle cell lymphoma, breast cancer, head and neck cancer, ovarian cancer, colorectal cancer, tongue cancer, multiple myeloma, or large cell lung cancer.

Also provided are compounds described herein for use in the treatments described herein. Also provided are uses of compounds described herein for the manufacture of medicaments for the treatments described herein.

Assay Methods

Compounds can be assayed for liver cancer activity according to any assay known to those of skill in the art.

Further, compounds can be assayed for accumulation in liver cells of a subject according to any assay known to those of skill in the art. In certain embodiments, a compound can be administered to the subject, and a liver cell of the subject can be assayed for the compound or a derivative thereof, e.g. a nucleoside, nucleoside phosphate or nucleoside triphosphate derivative thereof.

In certain embodiments, a nucleoside compound is administered to cells, such as liver cells, in vivo or in vitro, and the nucleoside triphosphate levels delivered intracellularly are measured, to indicate delivery of the compound and triphosphorylation in the cell. The levels of intracellular nucleoside triphosphate can be measured using analytical techniques known in the art. Methods of detecting ddATP are described herein below by way of example, but other nucleoside triphosphates can be readily detected using the appropriate controls, calibration samples and assay techniques.

In certain embodiments, ddATP concentrations are measured in a sample by comparison to calibration standards made from control samples. The ddATP concentrations in a sample can be measured using an analytical method such as HPLC LC MS. In certain embodiments, a test sample is compared to a calibration curve created with known concentrations of ddATP to thereby obtain the concentration of that sample.

In certain embodiments, the samples are manipulated to remove impurities such as salts ($Na^+$, $K^+$, etc.) before analysis. In certain embodiments, the lower limit of quantitation is about 0.2 pmol/mL for hepatocyte cellular extracts particularly where reduced salt is present.

In certain embodiments, the method allows successfully measuring triphosphate nucleotides formed at levels of 1-10,000 pmol per million cells in e.g. cultured hepatocytes and HepG2 cells Combination with Other Therapeutic Agents In one embodiment is a combination comprising a compounds as described herein, e.g., of Formulas I-VI, or pharmaceutically acceptable salt thereof, and one, two, three or more other therapeutic agents, e.g. anti-cancer agents.

In certain embodiments, the compounds and compositions provided herein are useful in methods of treatment of a liver cancer, that comprise further administration of a second agent effective for the treatment of the liver cancer in a subject in need thereof. The second agent can be any agent known to those of skill in the art to be effective for the treatment of the liver cancer, including those currently approved by the FDA.

In certain embodiments, a compound provided herein is administered in combination with one second agent. In further embodiments, a compound provided herein is administered in combination with two second agents. In still further embodiments, a compound provided herein is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an anti-cancer agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In certain embodiments, the second agent is selected from the group consisting of sorafenib tosylate (Nexavar), radiation therapy, selective internal radiation therapy (e.g., SIR-Spheres and TheraSphere), ethiodized oil (Lipidol), pexastimogene devacirepvec (Pexa-Vec, JX-594, Jennarex), Quinacrine (Clevelane BioLabs), CC-223 (Celgene), CF102 (Can-Fite), SGI-110 (Astex), and G-202 (Genspera).

In one embodiment, the other anticancer agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3, PD-1 antagonists and BET bromodomain inhibitors.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-y!)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, and sold under the tradename Thioplex®.

Examples of anti-tumor antibiotics include, but are not limited to, doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), and mitomycin C (sold under the tradename Mutamycin®).

Examples of anti-metabolites include, but are not limited to, claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodium (MTX), sold under the tradenames Rheumatrex® and Trexall™), and pentostatin (sold under the tradename Nipent®).

Examples of retinoids include, but are not limited to, alitretinoin (sold under the tradename Panretin®), tretinoin (all-trans retinoic acid, also known as ATRA, sold under the tradename Vesanoid®), Isotretinoin (13-c/s-retinoic acid, sold under the tradenames Accutane®, Amnesteem®, Claravis®, Clarus®, Decutan®, Isotane®, Izotech®, Oratane®, Isotret®, and Sotret®), and bexarotene (sold under the tradename Targretin®).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename Trisenox®), asparaginase (also known as L-asparaginase, and *Erwinia* L-asparaginase, sold under the tradenames Elspar® and Kidrolase®).

In an embodiment, the other anticancer agent is a BET bromodomain inhibitor. Examples of BET bromodomain inhibitor include the compounds described in U.S. Pat. No. 5,712,274, WO1994006802, U.S. Pat. No. 8,476,260 and WO2009/084693.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); CDCl$_3$ (deuterated chloroform); AcOH (acetic acid); DCM (dichloromethane); DMSO (dimethylsulfoxide); DMSO-d$_6$ (deuterated dimethylsulfoxide); EtOAc (ethyl acetate); MeOH (methanol); BOC (t-butyloxycarbonyl); and dMTr (4,4'-dimethoxytrityl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Scheme 1
Preparation of Compounds 101 to 104
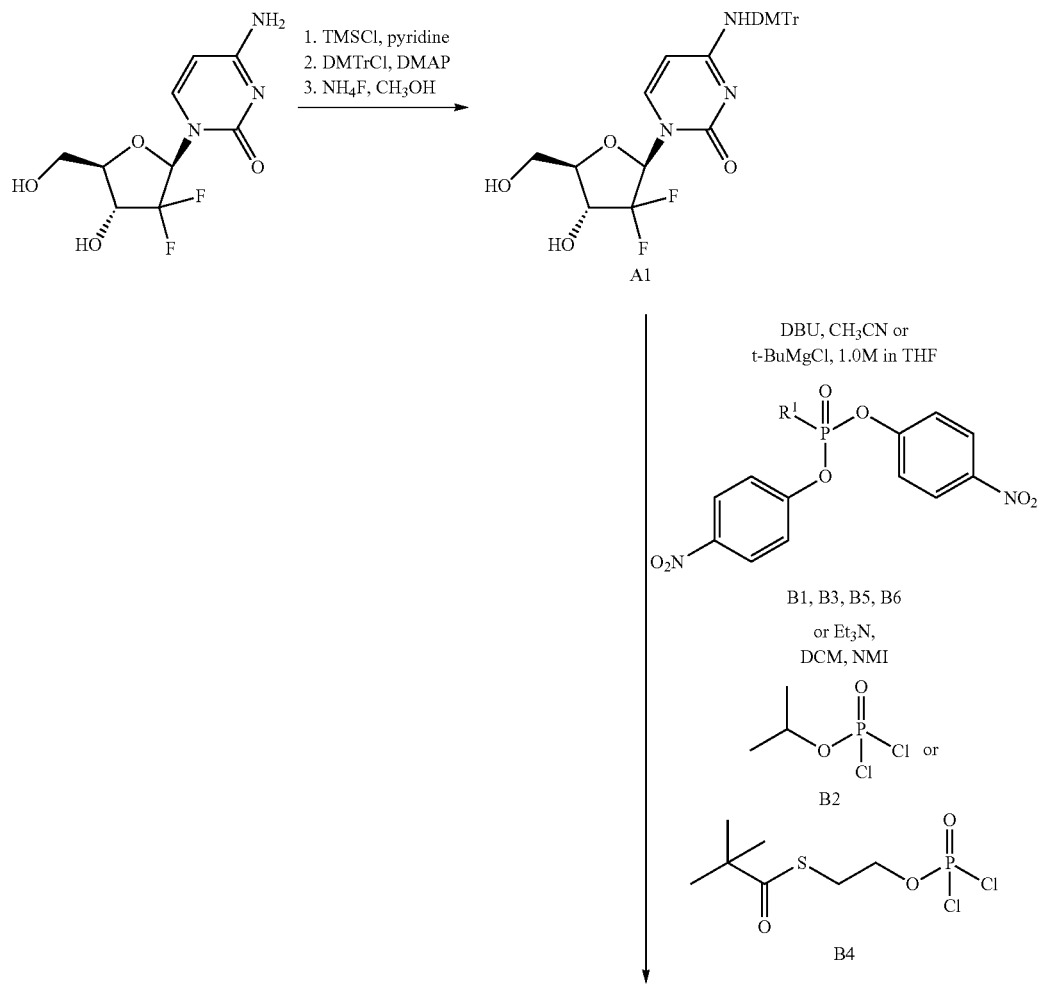
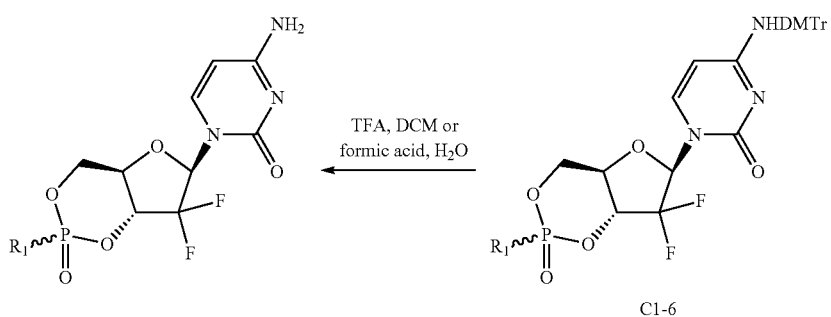

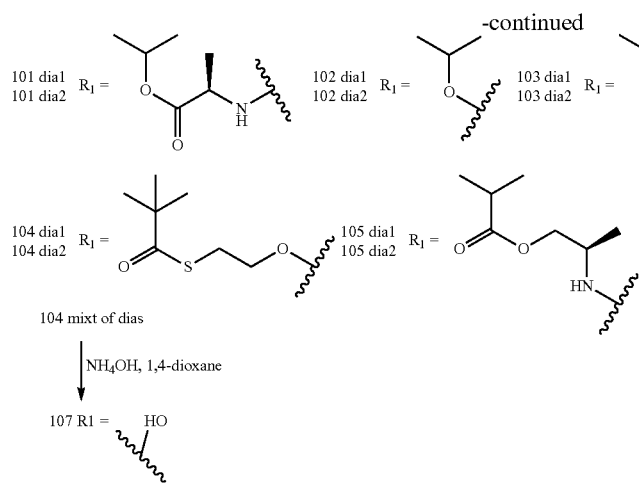

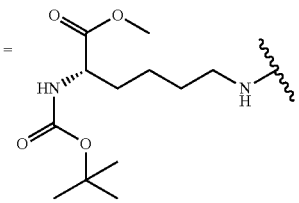

Compound A1 was synthesized from gemcitabine according to procedure described in literature. Compound 101 were synthesized according to scheme 1 and to the following general procedure A or B.

General procedure A:

Step 1: To a solution of compound A1 (1.94 mmol) in THF (25 mL/mmol) at 0° C. was added a solution of tert-butylmagnesium chloride, 1M in THF (5.83 mmol) followed by the appropriate reagent B1 (2.33 mmol) in DCM. The reaction mixture was stirred at room temperature overnight. The reaction mixture was diluted with ethyl acetate and quenched with brine. The aqueous layer was extracted with ethyl acetate. The combined organic layers were dried, filtered and concentrated under reduced pressure. The crude residue was purified by flash chromatography on silica gel (DCM/methanol: 0 to 20%) to afford the expected intermediate C1; Step 2: To a solution of C1 (0.20 mmol) in DCM (30 mL/mmol) was added trifluoroacetic acid (2.4 mmol) under nitrogen. The reaction mixture was stirred at room temperature between 2 hours and overnight, and then concentrated under reduced pressure. The crude residue was purified by flash chromatography on silica gel (DCM/methanol: 0 to 20%) to afford the expected compound as mixture of diastereoisomers. This mixture was purified by MS-preparative HPLC or by chiral HPLC to afford the 2 expected diastereoisomers as pure solid compounds.

General Procedure B:

Step 1: To a solution of reagent B1 (4.7 mmol) in DCM (25 mL/mmol) at room temperature was added a stirring suspension of compound A1 (3.9 mmol) in a mixture of THF (12 mL/mmol) and acetonitrile (25 mL/mmol), followed by 1,8-diazabicyclo[5.4.0]undec-7-ene (9.3 mmol). The reaction mixture was stirred at room temperature overnight. The reaction was monitored by LC/MS. The reaction mixture was concentrated under reduced pressure and purified by flash chromatography on silica gel (DCM/methanol: 0 to 20%) followed by preparative HPLC ($H_2O/CH_3CN$) to afford the expected compound C1 as mixture of diastereoisomers.

Step 2: according to step 2 of general procedure A.

Example 1

Compound 101

Two Diastereomers

Isopropyl (2R)-2-[[(4aR,6R,7aR)-6-(4-amino-2-oxo-pyrimidin-1-yl)-7,7-difluoro-2-oxo-4,4a,6,7a-tetrahydrofuro[3,2-d][1,3,2]dioxaphosphinin-2-yl]amino]propanoate

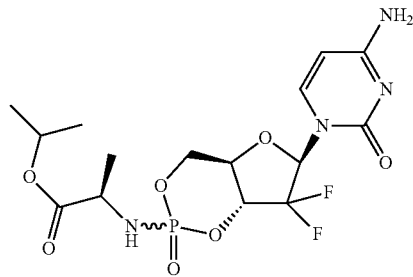

Compound 101 (Diastereoisomer 1): $^{1}$H NMR (DMSO-$d_6$, 400 MHz) δ (ppm) 7.56-7.48 (m, 3H), 6.36 (brs, 1H), 6.12-6.07 (m, 1H), 5.84 (d, J=7.05 Hz, 1H), 4.89 (heptuplet, J=6.26 Hz, 1H), 4.84 (brs, 1H), 4.66-4.58 (m, 1H), 4.55-4.48 (m, 1H), 4.27 (brs, 1H), 3.83-3.73 (m, 1H), 1.30 (d, J=7.24 Hz, 3H), 1.18 (d, J=6.22 Hz, 3H), 1.18 (d, J=6.22 Hz, 3H); $^{31}$P NMR (DMSO-$d_6$, 162 MHz) δ (ppm) 2.43 (s, 1P); $^{19}$F NMR (DMSO-$d_6$, 376 MHz) δ (ppm) −116.70 (brs, 2F); MS (ESI) m/z=439.0 (MH$^+$).

Compound 101 (Diastereoisomer 2): $^{1}$H NMR (DMSO-$d_6$, 400 MHz) δ (ppm) 7.83-7.82 (m, 1H), 7.45 (s, 2H), 6.37 (brs, 1H), 6.29 (dd, J=14.00 Hz, 9.98 Hz, 1H), 5.76 (d, J=7.34 Hz, 1H), 5.05 (brs, 1H), 4.88 (heptuplet, J=6.28 Hz, 1H), 4.62-4.49 (m, 2H), 4.14-4.09 (m, 1H), 3.79-3.69 (m, 1H), 1.25 (d, J=7.34 Hz, 3H), 1.20-1.17 (m, 6H); $^{31}$P NMR (DMSO-$d_6$, 162 MHz) δ (ppm) 5.11 (s, 1P); $^{19}$F NMR (DMSO-$d_6$, 376 MHz) δ (ppm) −116.64 (d, J=230 Hz, 1F), −117.40 (d, J=230 Hz, 1F); MS (ESI) m/z=439.0 (MO.

Compounds 102 were synthesized according to scheme 1 and to the following general procedure C.

General Procedure C:

Step 1: To a solution of compound A1 (43.79 mmol) in DCM (5.5 mL/mmol) was added triethylamine (174.7 mmol). The reaction mixture was cooled to −20° C. and then, isopropyl phosphorodichloridate B2 (87.6 mmol) was added dropwise at −20° C. The reaction mixture was stirred for 15 minutes at −20° C. and then 1-Methylimidazole (174.7 mmol) was added dropwise. The temperature was then slowly raised to room temperature and the reaction mixture was stirred for 15 hours. The reaction mixture was then concentrated under reduced pressure. The crude residue was purified by flash chromatography on silica gel (DCM/ethyl acetate: 50 to 100%) to afford the expected compound C2 as a solid.

Step 2: according to step 2 of general procedure A.

Example 2

Compound 102

Two Diastereomers

1-[(4aR,6R,7aR)-7,7-difluoro-2-isopropoxy-2-oxo-4,4a,6,7a-tetrahydrofuro[3,2-d][1,3,2]dioxaphosphinin-6-yl]-4-amino-pyrimidin-2-one

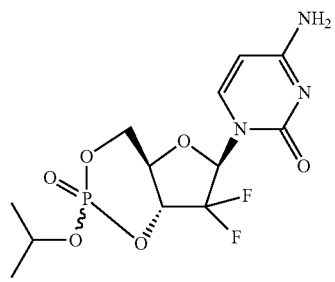

Compounds 102 were synthesized according to scheme 1 and to the following general procedure C.

Compound 102 (Diastereoisomer 1): $^1$H NMR (DMSO-d$_6$, 400 MHz) δ (ppm) 7.82 (brs, 1H), 7.60 (s, 1H), 7.57 (s, 1H), 6.43 (brs, 1H), 5.82 (d, J=7.15 Hz, 1H), 4.89 (brs, 1H), 4.73-4.64 (m, 2H), 4.51 (brs, 1H), 4.25 (brs, 1H), 1.39-1.36 (m, 6H); $^{31}$P NMR (DMSO-d$_6$, 162 MHz) δ (ppm) −8.64 (s, 1P); $^{19}$F NMR (DMSO-d$_6$, 376 MHz) δ (ppm) −115.65 (d, J=232 Hz, 1F), −116.61 (d, J=232 Hz, 1F); MS (ESI) m/z=368.0 (MH$^+$).

Compound 102 (Diastereoisomer 2): $^1$H NMR (DMSO-d$_6$, 400 MHz) δ (ppm) 7.77 (d, J=7.48 Hz, 1H), 7.50 (s, 1H), 7.47 (s, 1H), 6.43 (brs, 1H), 5.78 (d, J=7.48 Hz, 1H), 5.25 (brs, 1H), 4.73-4.58 (m, 3H), 4.36 (brs, 1H), 1.30 (d, J=6.15 Hz, 6H); $^{31}$P NMR (DMSO-d$_6$, 162 MHz) δ (ppm) −6.27 (s, 1P); $^{19}$F NMR (DMSO-d$_6$, 376 MHz) δ (ppm) −116.72 (s, 2F); MS (ESI) m/z=368.0 (MH$^+$).

Example 3

Compound 103

Two Diastereomers

Isopropyl (2S)-2-[[(4aR,6R,7aR)-6-(4-amino-2-oxo-pyrimidin-1-yl)-7,7-difluoro-2-oxo-4,4a,6,7a-tetrahydrofuro[3,2-d][1,3,2]dioxaphosphinin-2-yl]amino]propanoate

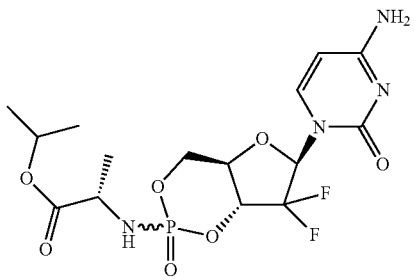

Compounds 103 were synthesized from B3 according to scheme 1 and to the general procedure A or B.

Compound 103 (Diastereoisomer 1): $^1$H NMR (DMSO-d$_6$, 400 MHz) δ (ppm) 7.61 (d, J=7.54 Hz, 1H), 7.50 (brs, 2H), 6.39 (brs, 1H), 6.15-6.08 (m, 1H), 5.84 (d, J=7.47 Hz, 1H), 4.91 (heptuplet, J=6.23 Hz, 1H), 4.91-4.81 (m, 1H), 4.65-4.57 (m, 1H), 4.54-4.47 (m, 1H), 4.29 (brs, 1H), 3.83-3.73 (m, 1H), 1.29 (d, J=7.18 Hz, 3H), 1.20 (d, J=6.19 Hz, 3H), 1.19 (d, J=6.19 Hz, 3H); $^{31}$P NMR (DMSO-d$_6$, 162 MHz) δ (ppm) 2.68 (s, 1P); $^{19}$F NMR (DMSO-d$_6$, 376 MHz) δ (ppm) −116.12-(−117.18) (m, 2F); MS (ESI) m/z=439.0 (MH$^+$).

Compound 103 (Diastereoisomer 2): $^1$H NMR (DMSO-d$_6$, 400 MHz) δ (ppm) 7.83-7.82 (m, 1H), 7.46 (brs, 2H), 6.43-6.39 (m, 1H), 6.28 (dd, J=13.12 Hz and 9.95 Hz, 1H), 5.76 (d, J=7.51 Hz, 1H), 5.09-5.04 (m, 1H), 4.89 (heptuplet, J=6.34 Hz, 1H), 4.61-4.46 (m, 2H), 4.12 (brs, 1H), 3.80-3.69 (m, 1H), 1.25 (d, J=7.05 Hz, 3H), 1.195 (d, J=6.28 Hz, 3H), 1.19 (d, J=6.28 Hz, 3H); $^{31}$P NMR (DMSO-d$_6$, 162 MHz) δ (ppm) 5.32 (s, 1P); $^{19}$F NMR (DMSO-d$_6$, 376 MHz) δ (ppm) −116.19-(−117.58) (m, 2F); MS (ESI) m/z=439.0 (MH$^+$).

Example 4

Compound 104

Two Diastereomers

S-[2-[[(4aR,6R,7aR)-6-(4-amino-2-oxo-pyrimidin-1-yl)-7,7-difluoro-2-oxo-4,4a,6,7a-tetrahydrofuro[3,2-d][1,3,2]dioxaphosphinin-2-yl]oxy]ethyl] 2,2-dimethylpropanethioate

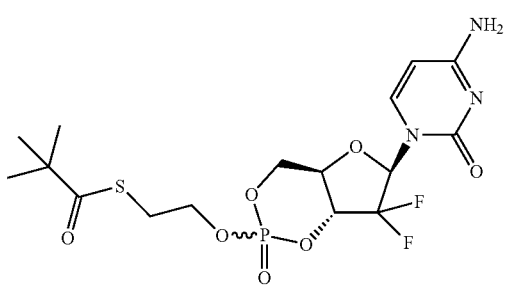

Compounds 104 were synthesized from reagent B4 according to scheme 1 and to the following general procedure D.

General Procedure D:

Step 1: To a stirred solution of compound A1 (3.54 mmol) in DCM (10 mL/mmol) at 0° C. were added triethylamine (14.14 mmol) and reagent B4 (5.30 mmol). The reaction mixture was stirred at 0° C. for 15 minutes and then was added N-methylimidazole (7.07 mmol). The reaction mixture was stirred at room temperature overnight, then diluted with DCM, washed with water, brine and NH$_4$Cl solution. The organic layer was dried and concentrated under reduced pressure. The crude residue was purified by flash chromatography on silica gel (DCM/methanol: 0 to 10%) to afford the expected intermediate.

Step 2: according to step 2 of general procedure A.

Compound 104 (Diastereoisomer 1): $^1$H NMR (MeOD, 400 MHz) δ (ppm) 7.70 (d, J=7.51 Hz, 1H), 5.96 (d, J=7.63 Hz, 1H), 4.80-4.71 (m, 1H), 4.62 (t, J=9.99, 1H), 4.33-4.22 (m, 3H), 3.27 (t, J=6.16 Hz, 2H), 1.26 (s, 9H); $^{31}$P NMR (MeOD, 162 MHz) δ (ppm) −7.23 (s, 1P); MS (ESI) m/z=470.0 (MH$^+$).

Compound 104 (Diastereoisomer 2): $^1$H NMR (MeOD, 400 MHz) δ (ppm) 7.66 (d, J=7.68 Hz, 1H), 5.96 (d, J=7.68 Hz, 1H), 4.83-4.77 (m, 1H), 4.71-4.64 (m, 1H), 4.51-4.44 (m, 1H), 4.25 (t, J=6.29 Hz, 1H), 4.23 (t, J=6.29 Hz, 1H), 3.22 (t, J=6.41 Hz, 2H), 1.26 (s, 9H); $^{31}$P NMR (MeOD, 162 MHz) δ (ppm) −5.60 (s, 1P); MS (ESI) m/z=470.2 (MH$^+$).

Example 5

Compound 105

Two Diastereomers

[(2R)-2-[[(4aR,6R,7aR)-6-(4-amino-2-oxo-pyrimidin-1-yl)-7,7-difluoro-2-oxo-4,4a,6,7a-tetrahydrofuro[3,2-d][1,3,2]dioxaphosphinin-2-yl]amino]propyl] 2-methylpropanoate

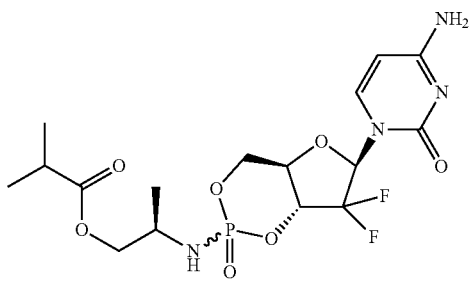

Compounds 105 were synthesized from reagent B5 according to scheme 1 and to the following general procedure B.

Compound 105 (Diastereoisomer 1): $^1$H NMR (DMSO-d$_6$, 400 MHz) δ (ppm) 8.21 (brs, 1H), 8.03 (brs, 1H), 7.96-7.94 (m, 1H), 6.36 (brs, 1H), 5.89 (d, J=7.63 Hz, 1H), 5.89-5.83 (m, 1H), 5.08 (brs, 1H), 4.58-4.52 (m, 2H), 4.17-4.12 (m, 2H), 3.87-3.85 (m, 2H), 3.42-3.32 (m, 1H), 2.56-2.51 (m, 1H), 1.09 (d, J=6.94 Hz, 6H), 1.08-1.06 (m, 2H); $^{31}$P NMR (DMSO-d$_6$, 162 MHz) δ (ppm) 6.24 (s, 1P); $^{19}$F NMR (DMSO-d$_6$, 376 MHz) δ (ppm) −116.18-(−117.64) (m, 2F); MS (ESI) m/z=453.2 (MH$^+$).

Compound 105 (Diastereoisomer 2): $^1$H NMR (MeOD, 400 MHz) δ (ppm) 7.87-7.85 (m, 1H), 6.33 (brs, 1H), 6.12-6.09 (m, 1H), 5.03-4.96 (m, 1H), 4.75-4.68 (m, 1H), 4.57-4.50 (m, 1H), 4.45-4.39 (m, 1H), 4.07 (d, J=11.19 Hz and 5.22 Hz, 1H), 3.99 (d, J=11.11 Hz and 6.24 Hz, 1H), 3.64-3.48 (m, 1H), 2.62 (heptuplet, J=7.02 Hz, 1H), 1.25 (d, J=6.74 Hz, 3H), 1.18-1.17 (m, 6H); $^{31}$P NMR (MeOD, 162 MHz) δ (ppm) 5.09 (s, 1P); $^{19}$F NMR (MeOD, 376 MHz) δ (ppm) −118.64 (m, 2F); MS (ESI) m/z=453.0 (MO.

Example 6

Compound 106

Two Diastereomers

Methyl (2S)-6-[[(4aR,6R,7aR)-6-(4-amino-2-oxo-pyrimidin-1-yl)-7,7-difluoro-2-oxo-4,4a,6,7a-tetrahydrofuro[3,2-d][1,3,2]dioxaphosphinin-2-yl]amino]-2-(tert-butoxycarbonylamino)hexanoate

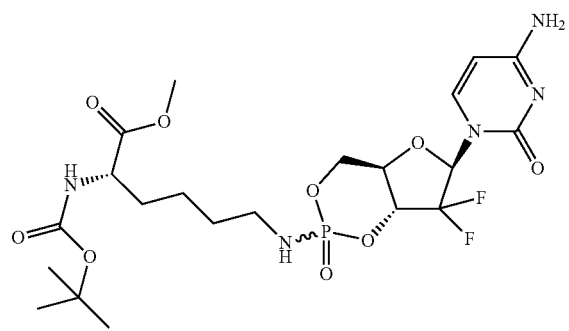

Compounds 106 were synthesized from reagent B6 according to scheme 1 and to the general procedure B. In this case, the diastereoisomers were isolated on step 1, and step 2 was done according to the following procedure: To a solution of pure diastereisomer of compound C6 (0.66 mmol) in water (3.5 mL/mmol) was added formic acid (14 mL/mmol). The reaction mixture was stirred at room temperature for 1 hour, and concentrated under reduced pressure. The crude residue was purified successively by flash chromatography on silica gel (DCM/methanol: 0 to 10%), RP-18 chromatography (H$_2$O/CH$_3$CN), and MS-preparative HPLC (H$_2$O/CH$_3$CN) to afford the expected compound as pure diastereoisomer.

Compound 106 (Diastereoisomer 1): $^1$H NMR (DMSO-d$_6$, 400 MHz) δ (ppm) 7.87-7.85 (m, 1H), 7.50-7.48 (m, 2H), 7.23 (d, J=7.66 Hz, 1H), 6.42-6.40 (m, 1H), 5.77 (d, J=7.56 Hz, 1H), 5.76-5.70 (m, 1H), 5.07-5.00 (m, 1H), 4.62-4.48 (m, 2H), 4.15-4.10 (m, 1H), 3.93-3.88 (m, 1H), 3.62 (s, 3H), 2.82-2.75 (m, 2H), 1.64-1.53 (m, 2H), 1.38 (s, 9H), 1.36-1.27 (m, 4H); $^{31}$P NMR (DMSO-d$_6$, 162 MHz) δ (ppm) 7.00 (s, 1P); $^{19}$F NMR (DMSO-d$_6$, 376 MHz) δ (ppm) −116.16-(−117.63) (m, 2F); MS (ESI) m/z=568.2 (MO.

Compound 106 (Diastereoisomer 2): $^1$H NMR (DMSO-d$_6$, 400 MHz) δ (ppm) 7.68 (d, J=7.59 Hz, 1H), 7.53-7.50 (m, 2H), 7.24 (d, J=7.63 Hz, 1H), 6.41 (brs, 1H), 5.83 (d, J=7.27 Hz, 1H), 5.56-5.53 (m, 1H), 4.81 (brs, 1H), 4.63-4.56 (m, 1H), 4.41 (brs, 1H), 4.30 (brs, 1H), 3.94-3.89 (m, 1H), 3.62 (s, 3H), 2.85-2.77 (m, 2H), 1.66-1.52 (m, 2H), 1.46-1.33 (m, 4H), 1.38 (s, 9H); $^{31}$P NMR (DMSO-d$_6$, 162 MHz) δ (ppm) 4.85 (s, 1P); $^{19}$F NMR (DMSO-d$_6$, 376 MHz) δ (ppm) −116.24 (s, 2F); MS (ESI) m/z=568.2 (MO.

Example 7

Compound 107

1-[(4aR,6R,7aR)-7,7-difluoro-2-hydroxy-2-oxo-4,4a,6,7a-tetrahydrofuro[3,2-d][1,3,2]dioxaphosphinin-6-yl]-4-amino-pyrimidin-2-one

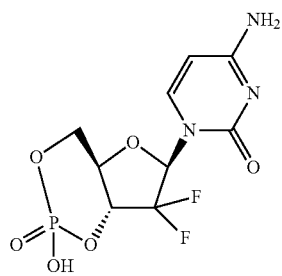

Compound 107 was synthesized from compound 104 (mixture of dias) according to scheme 1 and to the following procedure:

To a stirred solution of mixture of diastereoisomers of compound 104 (0.19 mmol) in 1,4-dioxane (40 mL/mmol) was added ammonium hydroxide solution (6 mL/mmol). The reaction mixture was stirred at room temperature for 4 hours, diluted with water and purified by 2 successives RP-18 chromatographies ($H_2O/CH_3CN$ and $H_2O$+TEAB/$CH_3CN$) to afford the expected compound.

Compound 107: $^1$H NMR (DMSO-$d_6$, 400 MHz) δ (ppm) 7.65 (d, J=7.53 Hz, 1H), 7.45-7.43 (m, 2H), 6.24 (brs, 1H), 5.79 (d, J=7.53 Hz, 1H), 4.41 (brs, 1H), 4.18-4.06 (m, 2H), 3.85-3.78 (m, 1H); $^{31}$P NMR (DMSO-$d_6$, 162 MHz) δ (ppm) −4.65 (s, 1P); $^{19}$F NMR (DMSO-$d_6$, 376 MHz) δ (ppm) −116.99 (s, 2F); MS (ESI) m/z=323.8 (MH$^-$).

Scheme 2: Preparation of Reagents D1 to D6

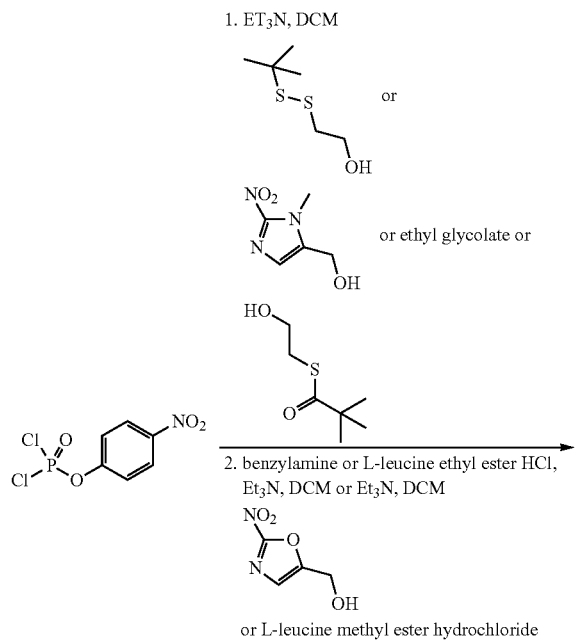

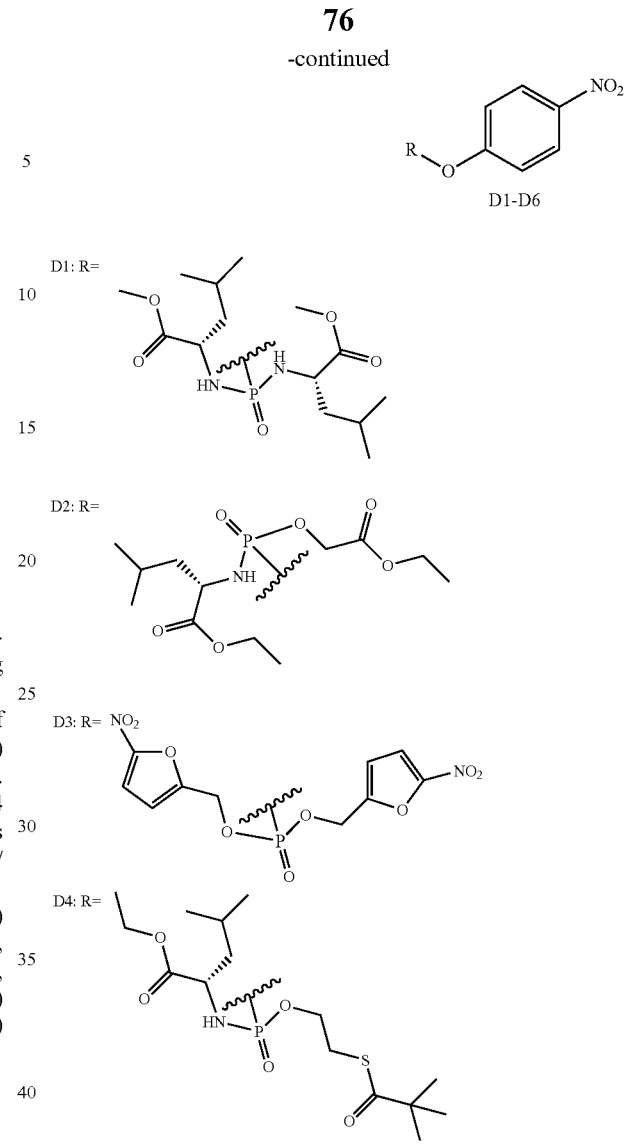

Reagents D1-6 were synthesized according to scheme 2:

Reagent D1: Methyl (2S)-2-[[[[(1S)-1-methoxycarbonyl-3-methyl-butyl]amino]-(4-nitrophenoxy) phosphoryl]amino]-4-methyl-pentanoate: MS (ESI) m/z=474.2 (MH$^+$).

Reagent D2: Ethyl (2S)-2-[[(2-ethoxy-2-oxo-ethoxy)-(4-nitrophenoxy)phosphoryl]amino]-4-methyl-pentanoate: MS (ESI) m/z=447.1 (MH+).

Reagent D3: Bis[(5-nitro-2-furyl)methyl](4-nitrophenyl) phosphate: MS (ESI) m/z=492.3 (MNa+).

Reagent D4 Ethyl (2S)-2-[[2-(2,2-dimethylpropanoylsulfanyl)ethoxy-(4-nitrophenoxy)-phosphorxl]amino]-4-methyl-pentanoate: MS (ESI) m/z=503.2 (MH−).

Reagent D5: N-[2-(tert-butyldisulfanyl)ethoxy-(4-nitrophenoxy)phosphoryl]-1-phenyl-methanamine: MS (ESI) m/z=457.2 (MH+).

Reagent D6: N-[(3-methyl-2-nitro-imidazol-4-yl)methoxy-(4-nitrophenoxy)phosphoryl]-1-phenyl-methanamine: MS (ESI) m/z=448.0 (MH+).

Scheme 3
Preparation of Compounds 108, 109, 110, 111, 112, and 113

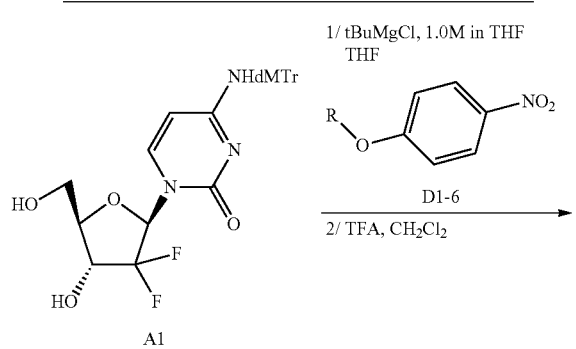

A1

108 dia1
R3 = H; R2 = R =
108 dia2

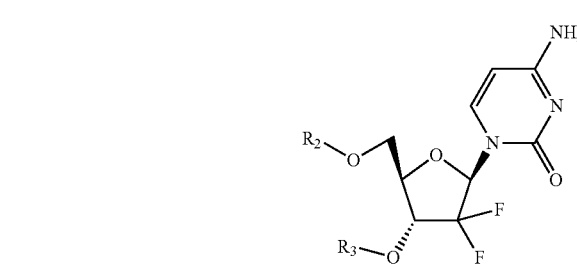

109 R3 = H; R2 = R =

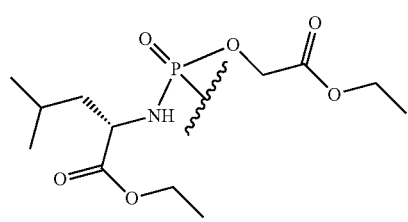

110 Mixt of dias
R3 = H; R2 = R =

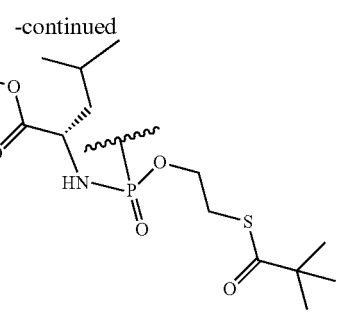

NH4OH
1,4-Dioxane

115 R3 = H; R2 = R =

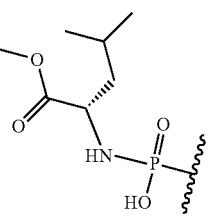

111 dia1
R3 = H; R2 = R =
111 dia2

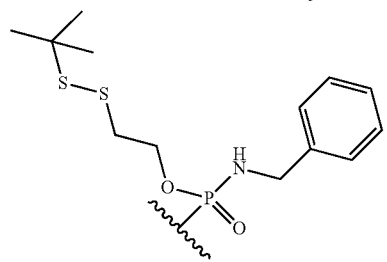

112 dia1
R3 = H; R2 = R =
112 dia2

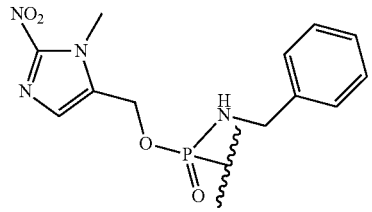

113 R2 = H; 
R3 = R =

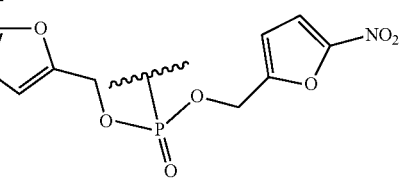

Compounds 108, 109, 110, 111, 112 and 113 were synthesized from compound A1 according to scheme 3 and to the general procedure E.

General procedure E:

Step 1: To a solution of compound A1 (2.00 mmol) in THF (10 mL/mmol) at 0° C. was added a solution of tert-butylmagnesium chloride, 1M in THF (4.20 mmol). The reaction mixture was stirred for 1 hour at room temperature, then cooled to 0° C. To this reaction mixture was added a solution of the appropriate reagent D1-6 (2.20 mmol) in THF (10 mL/mmol). The reaction mixture was stirred for 1 hour at 0° C. and at room temperature overnight. The reaction mixture was diluted with ethyl acetate and washed with a saturated NH4Cl solution (or a saturated NaHCO3 solution), water and brine. The organic layer was dried, filtered and concentrated under reduced pressure. The crude residue was purified by flash chromatography on silica gel (DCM/ethanol: 0 to 20%) to afford the expected intermediate as a mixture of diastereoisomers;

Step 2: according to step 2 of general procedure A.

Example 8

Compound 108

Two Diastereomers

Ethyl (2S)-2-[[[(2R,3R,5R)-5-(4-amino-2-oxo-pyrimidin-1-yl)-4,4-difluoro-3-hydroxy-tetrahydrofuran-2-yl]methoxy-(2-ethoxy-2-oxo-ethoxy)phosphoryl]amino]-4-methyl-pentanoate

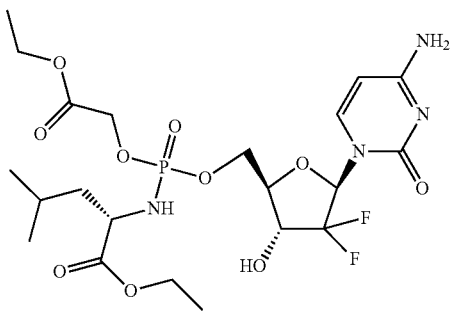 [SMILES: CCOC(=O)COP(=O)(N[C@@H](CC(C)C)C(=O)OCC)OC[C@H]1O[C@@H](n2ccc(N)nc2=O)C(F)(F)[C@@H]1O]

Compound 108 was synthesized from compound A1 and reagent D2 according to scheme 3 and to the general procedure E.

Compound 108 (Diastereoisomer 1): $^1$H NMR (MeOD, 400 MHz) δ (ppm) 7.71 (d, J=7.52 Hz, 1H), 6.31-6.27 (m, 1H), 5.99 (d, J=7.52 Hz, 1H), 4.63-4.51 (m, 2H), 4.48-4.34 (m, 2H), 4.30-4.13 (m, 5H), 4.10-4.08 (m, 1H), 3.89-3.84 (m, 1H), 3.32-3.31 (m, 3H), 1.87-1.74 (m, 1H), 1.58-1.55 (m, 2H), 1.31-1.25 (m, 6H), 0.96-0.94 (m, 6H); $^{31}$P NMR (MeOD, 162 MHz) δ (ppm) 8.93 (s, 1P); $^{19}$F NMR (MeOD, 376 MHz) δ (ppm) −118.05-(−120.51) (m, 2F); MS (ESI) m/z=571.3 (MH$^+$).

Compound 108 (Diastereoisomer 2): $^1$H NMR (MeOD, 400 MHz) δ (ppm) 7.57-7.55 (m, 1H), 6.19-6.14 (m, 1H), 5.88-5.85 (m, 1H), 4.52-4.49 (m, 2H), 4.36-4.32 (m, 1H), 4.24-4.05 (m, 6H), 3.97-3.95 (m, 1H), 3.81-3.76 (m, 1H), 3.21-3.20 (m, 2H), 1.73-1.64 (m, 1H), 1.47-1.44 (m, 2H), 1.21-1.15 (m, 6H), 0.85-0.82 (m, 6H); $^{31}$P NMR (MeOD, 162 MHz) δ (ppm) 9.11 (s, 1P); $^{19}$F NMR (MeOD, 376 MHz) δ (ppm) −117.89-(−120.32) (m, 2F); MS (ESI) m/z=571.4 (MO.

Example 9

Compound 109

Methyl (2S)-2-[[[(2R,3R,5R)-5-(4-amino-2-oxo-pyrimidin-1-yl)-4,4-difluoro-3-hydroxy-tetrahydrofuran-2-yl]methoxy-[[(1S)-1-methoxycarbonyl-3-methyl-butyl]amino]phosphoryl]amino]-4-methyl-pentanoate

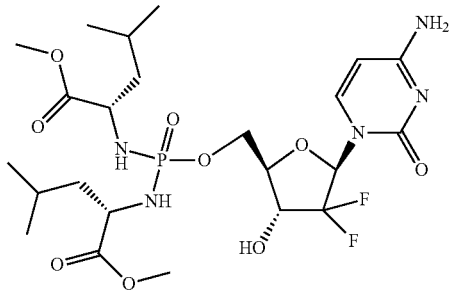 [SMILES: COC(=O)[C@H](CC(C)C)NP(=O)(N[C@@H](CC(C)C)C(=O)OC)OC[C@H]1O[C@@H](n2ccc(N)nc2=O)C(F)(F)[C@@H]1O]

Compound 109 was synthesized from compound A1 and reagent D1 according to scheme 3 and to the general procedure E.

Compound 109: $^1$H NMR (DMSO-d$_6$, 400 MHz) δ (ppm) 7.52 (d, J=7.59 Hz, 1H), 7.41 (brs, 1H), 7.35 (brs, 1H), 6.33 (s, 1H), 6.15 (t, J=8.38 Hz, 1H), 5.78 (d, J=7.59 Hz, 1H), 4.86 (t, J=11.06 Hz, 1H), 4.80 (t, J=10.84 Hz, 1H), 4.21-4.07 (m, 2H), 4.04-3.98 (m, 1H), 3.95-3.91 (m, 1H), 3.72-3.64 (m, 2H), 3.60-3.59 (m, 6H), 1.71-1.64 (m, 2H), 1.49-1.36 (m, 4H), 0.85-0.83 (m, 12H); 3'P NMR (DMSO-d$_6$, 162 MHz) δ (ppm) 13.17 (s, 1P); MS (ESI) m/z=598.4 (MH$^+$).

Example 10

Compound 110

Mixture of Diastereomers

Ethyl (2S)-2-[[[(2R,3R,5R)-5-(4-amino-2-oxo-pyrimidin-1-yl)-4,4-difluoro-3-hydroxy-tetrahydrofuran-2-yl]methoxy-[2-(2,2-dimethylpropanoylsulfanyl)ethoxy]phosphoryl]amino]-4-methyl-pentanoate

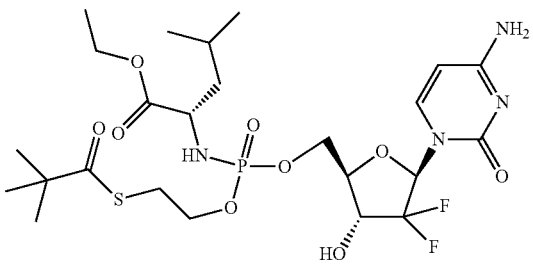 [SMILES: CCOC(=O)[C@H](CC(C)C)NP(=O)(OCCSC(=O)C(C)(C)C)OC[C@H]1O[C@@H](n2ccc(N)nc2=O)C(F)(F)[C@@H]1O]

Compound 110 was synthesized from compound A1 and reagent D4 according to scheme 3 and to the general procedure E.

Compound 110: MS (ESI) m/z=629.4 (MH$^+$).

Example 11

Compound 111

Two Diastereomers 4-amino-1-[(2R,4R,5R)-5-[[[(benzylamino)-[2-(tert-butyldisulfanyl)ethoxy]phosphoryl]oxymethyl]-3,3-difluoro-4-hydroxytetrahydrofuran-2-yl]pyrimidin-2-one

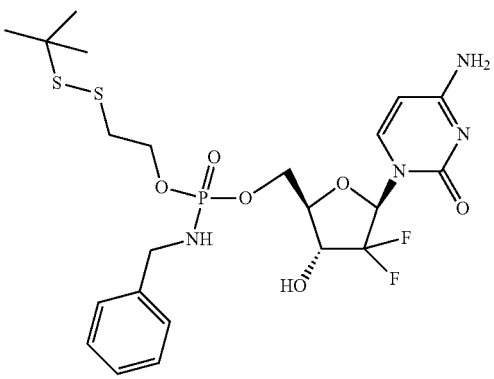 [SMILES: CC(C)(C)SSCCOP(=O)(NCc1ccccc1)OC[C@H]1O[C@@H](n2ccc(N)nc2=O)C(F)(F)[C@@H]1O]

Compound 111 was synthesized from compound A1 and reagent D5 according to scheme 3 and to the general procedure E.

Compound 111 (Diastereoisomer 1): $^1$H NMR (DMSO-$d_6$, 400 MHz) δ (ppm) 7.49 (d, J=7.51 Hz, 1H), 7.40 (brs, 1H), 7.37 (brs, 1H), 7.33-7.28 (m, 3H), 7.24-7.20 (m, 1H), 6.43 (brs, 1H), 6.18-6.14 (m, 1H), 5.75-5.68 (m, 2H), 4.21-3.96 (m, 7H), 2.90 (t, J=6.56 Hz, 2H), 1.27 (s, 9H); $^{31}$P NMR (DMSO-$d_6$, 162 MHz) δ (ppm) 10.07 (s, 1P); $^{19}$F NMR (DMSO-$d_6$, 376 MHz) δ (ppm) −115.30-(−116.57) (m, 2F); MS (ESI) m/z=581.0 (MH$^+$).

Compound 111 (Diastereoisomer 2): $^1$H NMR (DMSO-$d_6$, 400 MHz) δ (ppm) 7.51 (d, J=7.50 Hz, 1H), 7.40 (brs, 1H), 7.37 (brs, 1H), 7.32-7.28 (m, 4H), 7.25-7.20 (m, 1H), 6.43 (brs, 1H), 6.16 (t, J=8.64 Hz, 1H), 5.77-5.70 (m, 2H), 4.19-3.95 (m, 8H), 2.90 (t, J=6.52 Hz, 2H), 1.27 (s, 9H); $^{31}$P NMR (DMSO-$d_6$, 162 MHz) δ (ppm) 9.90 (s, 1P); $^{19}$F NMR (DMSO-$d_6$, 376 MHz) δ (ppm) −115.47-(−116.65) (m, 2F); MS (ESI) m/z=581.0 (MH$^+$).

Example 12

Compound 112

Two Diastereomers 4-amino-1-[(2R,4R,5R)-5-[[(benzylamino)-[(3-methyl-2-nitro-imidazol-4-yl)methoxy]phosphoryl]oxymethyl]-3,3-difluoro-4-hydroxy-tetrahydrofuran-2-yl]pyrimidin-2-one

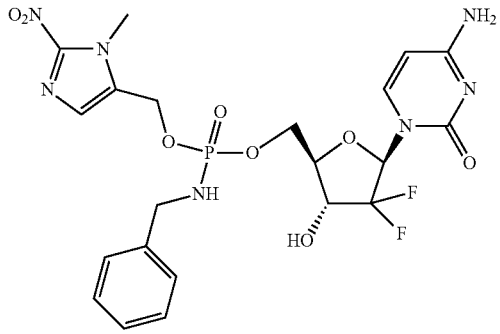 [SMILES: Cn1c(COP(=O)(NCc2ccccc2)OC[C@H]2O[C@@H](n3ccc(N)nc3=O)C(F)(F)[C@@H]2O)cnc1[N+](=O)[O-]]

Compound 112 was synthesized with 2 methods:
Method 1: from compound A1 and reagent D6 according to scheme 3 and to the general procedure E.

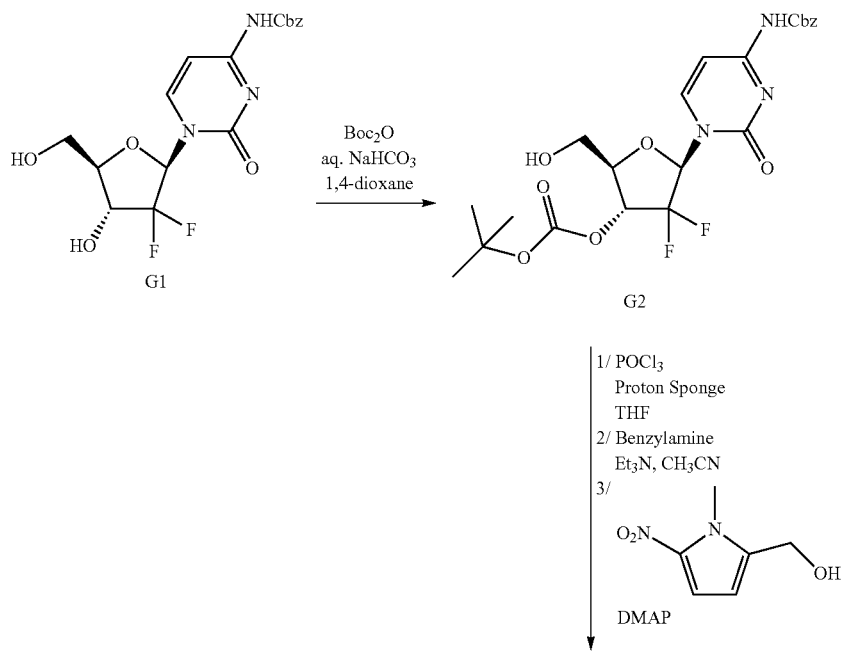

83

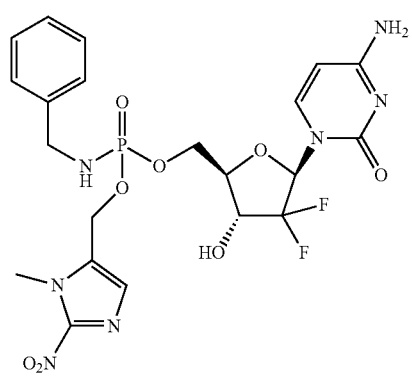

112

←
NH₃/CH₃OH

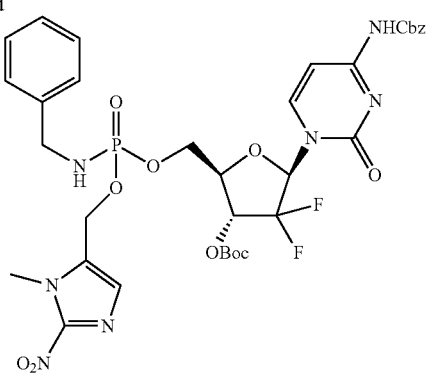

G3

84

Method 2: according to scheme 3bis and to the following procedure:

Step 1: To a stirred solution of compound G1 (5.76 mmol) and di-tert-butyldicarbonate (6.34 mmol) in 1,4-dioxane (120 mL) was added a solution of sodium carbonate (28.80 mmol) in water (30 mL). 1,4-dioxane (150 mL) was added to the reaction mixture. The reaction mixture was stirred at room temperature overnight and at 40° C. for 8 hours and at room temperature for a further 2 days. The reaction was monitored by LC/MS. Di-tert-butyldicarbonate (5.76 mmol) was added and the reaction mixture was stirred at 80° C. for 2 hours. Di-tert-butyldicarbonate (12.90 mmol) was added again and the reaction mixture was stirred at 80° C. for 2 hours and at 50° C. over weekend. More di-tert-butyldicarbonate (22.11 mmol) was added and the reaction mixture was stirred at 80° C. for 2.5 hours. The reaction mixture was concentrated under reduced pressure and the crude residue was partitioned between ethyl acetate and water. The aqueous layer was further extracted with ethyl acetate. The combined organic layers were washed with water and brine, dried over sodium sulfate, filtered and concentrated under reduced pressure. The crude residue was purified by flash chromatography on silica gel (DCM/ethyl acetate: 1/1) to afford the expected intermediate G2.

Step 2: To a solution of compound G2 (3.41 mmol) in THF cooled to −12° C. was added dropwise phosphorus oxychloride (5.12 mmol). The reaction mixture was stirred at −12° C. for 40 minutes and then, proton sponge (13.64 mmol) was added. The reaction mixture was stirred at −12° C. overnight. To this stirred reaction mixture was added a solution of benzylamine (3.75 mmol) and triethylamine (17.05 mmol) in acetonitrile (7 mL). The reaction mixture was then allowed to warm to −5° C. The reaction mixture was stirred for 5 hours. The reaction was monitored by LC/MS. To the reaction mixture was then added a solution of (3-methyl-2-nitro-3H-imidazol-4-yl)-methanol (10.23 mmol) and 4-(dimethylamino)pyridine (10.23 mmol) in acetonitrile (10 mL). The reaction mixture was stirred at room temperature overnight, and then concentrated under reduced pressure. The crude residue was partitioned between a 5% solution of citric acid and ethyl acetate. The organic layer was washed with water and brine, dried over over sodium sulfate, filtered and concentrated under reduced pressure. The crude residue was purified by flash chromatography on silica gel (DCM/methanol: 0 to 3%) to afford the expected compound G3. Step 3: A solution of compound G3 was dissolved in an ammonia solution (7M in methanol, 15 mL) and was stirred in pressure tube for 3 days at room temperature. The reaction mixture was concentrated under reduced pressure. The crude residue was purified by flash chromatography on silica gel (DCM/methanol: 0 to 10%) to afford the expected compound 112.

Compound 112 (Diastereoisomer 1): ¹H NMR (DMSO-d₆, 400 MHz) δ (ppm) 7.50 (d, J=7.45 Hz, 1H), 7.42-7.40 (m, 2H), 7.30-7.29 (m, 4H), 7.26-7.21 (m, 2H), 6.44 (brs, 1H), 6.20-6.14 (m, 1H), 5.92-5.85 (m, 1H), 5.73 (d, J=7.45 Hz, 1H), 5.10-4.99 (m, 2H), 4.24-4.12 (m, 3H), 4.01-3.96 (m, 3H), 3.86 (s, 3H); ³¹P NMR (DMSO-d₆, 162 MHz) δ (ppm) 10.26 (s, 1P); MS (ESI) m/z=571.7 (MO.

Compound 112 (Diastereoisomer 2): ¹H NMR (DMSO-d₆, 400 MHz) δ (ppm) 7.51 (d, J=7.48 Hz, 1H), 7.43-7.41 (m, 2H), 7.31-7.30 (m, 4H), 7.25-7.22 (m, 1H), 7.20 (s, 1H), 6.44-6.42 (m, 1H), 6.19-6.15 (m, 1H), 5.93-5.87 (m, 1H), 5.74 (d, J=7.48 Hz, 1H), 5.10-4.99 (m, 2H), 4.23-4.13 (m, 3H), 4.01-3.96 (m, 3H), 3.86 (s, 3H); ³¹P NMR (DMSO-d₆, 162 MHz) δ (ppm) 10.09 (s, 1P); MS (ESI) m/z=571.7 (MO.

Example 13

Compound 113

[(2R,3R,5R)-5-(4-amino-2-oxo-pyrimidin-1-yl)-4,4-difluoro-2-(hydroxymethyl)tetrahydrofuran-3-yl] bis[(5-nitro-2-furyl)methyl] phosphate

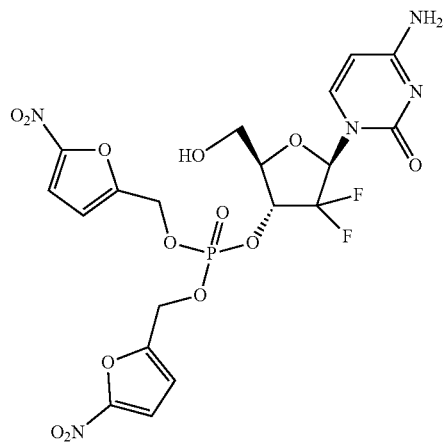 [SMILES: Nc1ccn([C@@H]2O[C@H](CO)[C@@H](OP(=O)(OCc3ccc([N+](=O)[O-])o3)OCc3ccc([N+](=O)[O-])o3)C2(F)F)c(=O)n1]

Compound 113 was synthesized from compound A1 and reagent D3 according to scheme 3 and to the general procedure E.

Compound 113: ¹H NMR (DMSO-d₆, 400 MHz) δ (ppm) 7.68-7.64 (m, 3H), 7.49-7.47 (m, 2H), 7.00-6.98 (m, 2H), 6.23-6.20 (m, 1H), 5.81 (d, J=7.52 Hz, 1H), 5.30-5.21 (m, 5H), 5.05-5.01 (m, 1H), 4.15-4.11 (m, 1H), 3.80-3.75 (m, 1H), 3.69-3.64 (m, 1H); $^{31}$P NMR (DMSO-d$_6$, 162 MHz) δ (ppm) −2.52 (s, 1P); MS (ESI) m/z=594.2 (MO.

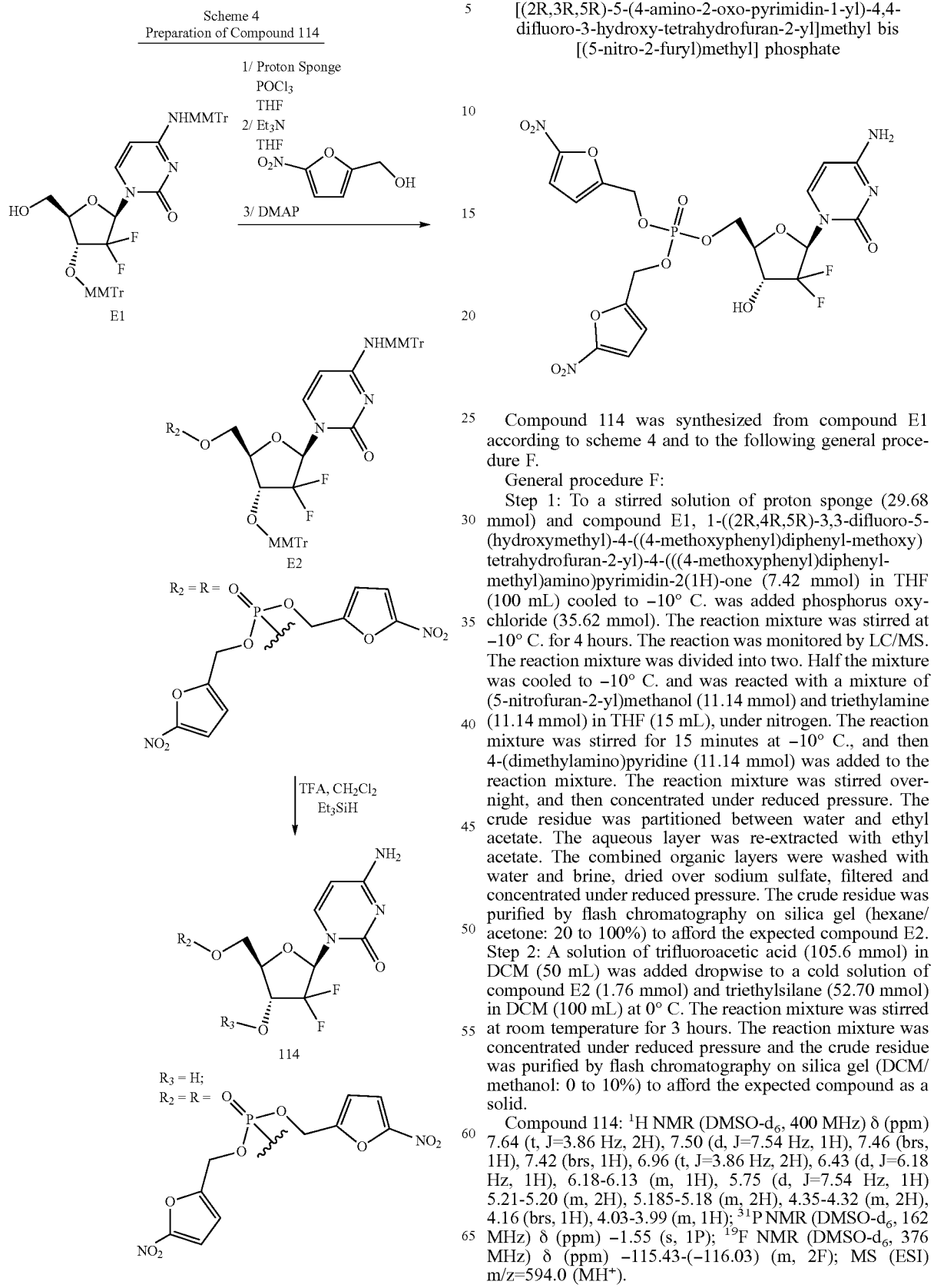

Example 14

Compound 114

[(2R,3R,5R)-5-(4-amino-2-oxo-pyrimidin-1-yl)-4,4-difluoro-3-hydroxy-tetrahydrofuran-2-yl]methyl bis [(5-nitro-2-furyl)methyl] phosphate Compound 114 was synthesized from compound E1 according to scheme 4 and to the following general procedure F.

General procedure F:

Step 1: To a stirred solution of proton sponge (29.68 mmol) and compound E1, 1-((2R,4R,5R)-3,3-difluoro-5-(hydroxymethyl)-4-((4-methoxyphenyl)diphenyl-methoxy)tetrahydrofuran-2-yl)-4-(((4-methoxyphenyl)diphenyl-methyl)amino)pyrimidin-2(1H)-one (7.42 mmol) in THF (100 mL) cooled to −10° C. was added phosphorus oxychloride (35.62 mmol). The reaction mixture was stirred at −10° C. for 4 hours. The reaction was monitored by LC/MS. The reaction mixture was divided into two. Half the mixture was cooled to −10° C. and was reacted with a mixture of (5-nitrofuran-2-yl)methanol (11.14 mmol) and triethylamine (11.14 mmol) in THF (15 mL), under nitrogen. The reaction mixture was stirred for 15 minutes at −10° C., and then 4-(dimethylamino)pyridine (11.14 mmol) was added to the reaction mixture. The reaction mixture was stirred overnight, and then concentrated under reduced pressure. The crude residue was partitioned between water and ethyl acetate. The aqueous layer was re-extracted with ethyl acetate. The combined organic layers were washed with water and brine, dried over sodium sulfate, filtered and concentrated under reduced pressure. The crude residue was purified by flash chromatography on silica gel (hexane/acetone: 20 to 100%) to afford the expected compound E2.

Step 2: A solution of trifluoroacetic acid (105.6 mmol) in DCM (50 mL) was added dropwise to a cold solution of compound E2 (1.76 mmol) and triethylsilane (52.70 mmol) in DCM (100 mL) at 0° C. The reaction mixture was stirred at room temperature for 3 hours. The reaction mixture was concentrated under reduced pressure and the crude residue was purified by flash chromatography on silica gel (DCM/methanol: 0 to 10%) to afford the expected compound as a solid.

Compound 114: $^1$H NMR (DMSO-d$_6$, 400 MHz) δ (ppm) 7.64 (t, J=3.86 Hz, 2H), 7.50 (d, J=7.54 Hz, 1H), 7.46 (brs, 1H), 7.42 (brs, 1H), 6.96 (t, J=3.86 Hz, 2H), 6.43 (d, J=6.18 Hz, 1H), 6.18-6.13 (m, 1H), 5.75 (d, J=7.54 Hz, 1H) 5.21-5.20 (m, 2H), 5.185-5.18 (m, 2H), 4.35-4.32 (m, 2H), 4.16 (brs, 1H), 4.03-3.99 (m, 1H); $^{31}$P NMR (DMSO-d$_6$, 162 MHz) δ (ppm) −1.55 (s, 1P); $^{19}$F NMR (DMSO-d$_6$, 376 MHz) δ (ppm) −115.43-(−116.03) (m, 2F); MS (ESI) m/z=594.0 (MH$^+$).

Example 15

Compound 115

[(2R,3R,5R)-5-(4-amino-2-oxo-pyrimidin-1-yl)-4,4-difluoro-3-hydroxy-tetrahydrofuran-2-yl]methoxy-N-[(1S)-1-ethoxycarbonyl-3-methyl-butyl]phosphonamidic acid

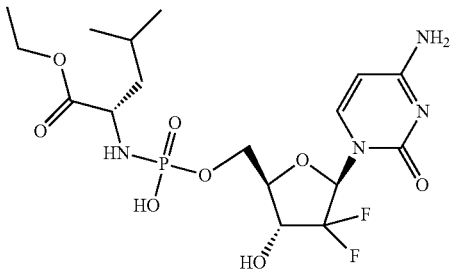 [SMILES: CCOC(=O)[C@H](CC(C)C)NP(=O)(O)OC[C@H]1O[C@@H](n2ccc(N)nc2=O)C(F)(F)[C@@H]1O]

Compound 115 was synthesized from compound 110 according to scheme 3 and to the following procedure:

To a stirred solution of mixture of diastereoisomers of compound 110 (0.32 mmol) in 1,4-dioxane (40 mL/mmol) was added ammonium hydroxide solution (2×3 mL/mmol). The reaction mixture was stirred at room temperature overnight and for 2 additional hours. The reaction mixture was concentrated under reduced pressure. The crude residue was purified by RP-18 chromatography (H$_2$O/CH$_3$CN) to afford the expected compound.

Compound 115: $^1$H NMR (DMSO-d$_6$, 400 MHz) δ (ppm) 7.60 (d, J=7.54 Hz, 1H), 7.40 (brs, 1H), 7.28 (brs, 1H), 7.13 (brs, 1H), 6.08 (t, J=7.82 Hz, 1H), 5.79 (d, J=7.54 Hz, 1H), 4.18-4.09 (m, 1H), 4.06-3.99 (m, 2H), 3.85-3.76 (m, 3H), 3.64-3.56 (m, 1H), 1.73-1.63 (m, 1H), 1.39-1.25 (m, 2H), 1.16 (t, J=7.18 Hz, 3H), 0.83 (d, J=6.65 Hz, 3H), 0.825 (d, J=6.65 Hz, 3H); $^{31}$P NMR (DMSO-d$_6$, 162 MHz) δ (ppm) 4.93 (s, 1P); MS (ESI) m/z=485.2 (MH$^+$).

Scheme 5
Preparation of Compound 116

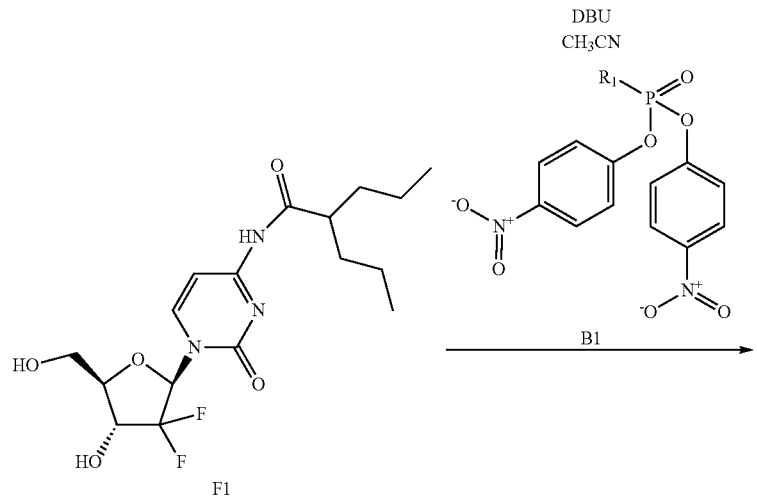

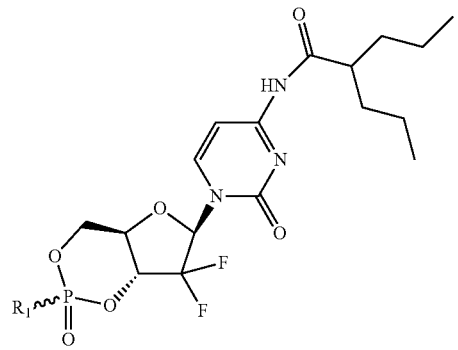

116 dia 1
116 dia 2

Example 16

Compound 116

Two Diastereomers

Isopropyl (2R)-2-[[(4aR,6R,7aR)-7,7-difluoro-2-oxo-6-[2-oxo-4-(2-propylpentanoylamino)pyrimidin-1-yl]-4,4a,6,7a-tetrahydrofuro[3,2-d][1,3,2]dioxaphosphinin-2-yl]amino]propanoate

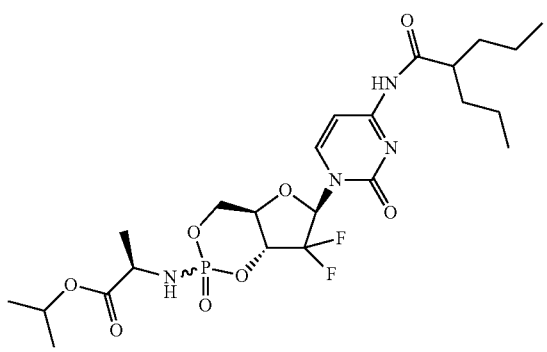

Compound 116 was synthesized from compound F1 according to scheme 5 and to the general procedure B step 1 to afford the 2 expected diastereoisomers as pure solids.

Compound 116 (Diastereoisomer 1): $^1$H NMR (DMSO-$d_6$, 400 MHz) δ (ppm) 11.15 (s, 1H), 8.33 (d, J=7.64 Hz, 1H), 7.33 (d, J=7.64 Hz, 1H), 6.42-6.34 (m, 2H), 5.13 (brs, 1H), 4.90 (heptuplet, J=6.20 Hz, 1H), 4.68 (brs, 1H), 4.64-4.55 (m, 1H), 4.25-4.20 (m, 1H), 3.82-3.71 (m, 1H), 2.68-2.60 (m, 1H), 1.58-1.48 (m, 2H), 1.39-1.31 (m, 2H), 1.28-1.19 (m, 13H), 0.88-0.84 (m, 6H); 3'P NMR (DMSO-$d_6$, 162 MHz) δ (ppm) 5.22 (s, 1P); MS (ESI) m/z=565.2 (MO.

Compound 116 (Diastereoisomer 2): $^1$H NMR (DMSO-$d_6$, 400 MHz) δ (ppm)): $^1$H NMR (DMSO-$d_6$, 400 MHz) δ (ppm) 11.18 (s, 1H), 8.13 (d, J=7.65 Hz, 1H), 7.40 (d, J=7.65 Hz, 1H), 6.40-6.34 (m, 1H), 6.20-6.14 (1H), 4.94-4.85 (m, 1H), 4.89 (heptuplet, J=6.20 Hz, 1H), 4.72-4.58 (m, 2H), 4.38 (brs, 1H), 3.84-3.74 (m, 1H), 2.68-2.61 (m, 1H), 1.58-1.49 (m, 2H), 1.39-1.31 (m, 5H), 1.28-1.18 (m, 10H), 0.88-0.84 (m, 6H); $^{31}$P NMR (DMSO-$d_6$, 162 MHz) δ (ppm) 2.53 (s, 1P); MS (ESI) m/z=565.2 (MH$^+$).

Examples 17-19

Compounds 117-119

The following compounds were prepared according to the procedures described above.

| Example | Compound structure | Compound number | Characterization info |
|---|---|---|---|
| 17 | Chiral 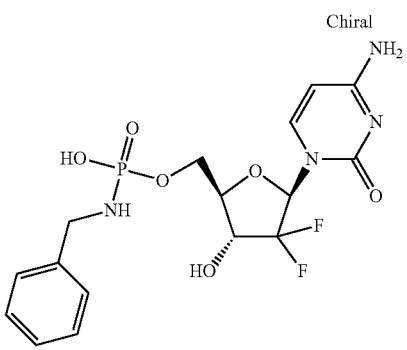 [SMILES: Nc1ccn([C@@H]2O[C@H](COP(=O)(O)NCc3ccccc3)[C@@H](O)C2(F)F)c(=O)n1] | 117 | MS (ESI) m/z = 433 (MH$^+$). |
| 18 | Chiral 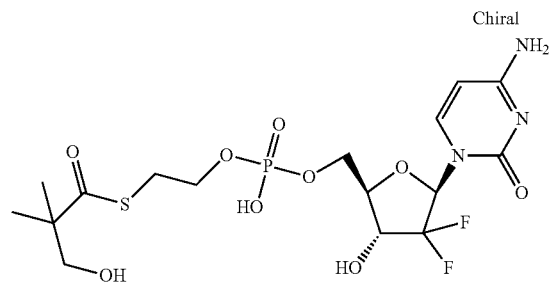 [SMILES: CC(C)(CO)C(=O)SCCOP(=O)(O)OC[C@H]1O[C@@H](n2ccc(N)nc2=O)C(F)(F)[C@@H]1O] | 118 | MS (ESI) m/z = 504.2 (MH$^+$). |

| Example | Compound structure | Compound number | Characterization info |
|---|---|---|---|
| 19 | 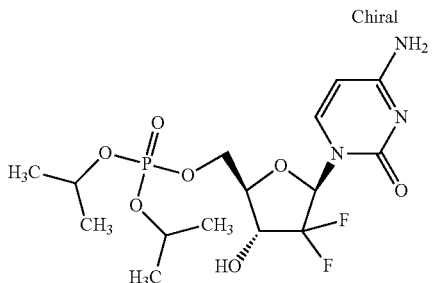 | 119 | MS (ESI) m/z = 428 (MH$^+$). |

Scheme 6
Preparation of Intermediate H1

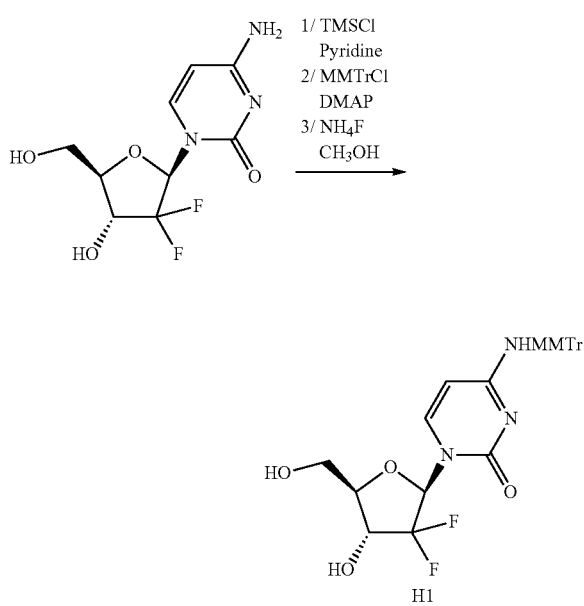

1-((2R,4R,5R)-3,3-difluoro-4-hydroxy-5-(hydroxymethyl)tetrahydrofuran-2-yl)-4-(((4-methoxyphenyl)diphenylmethyl)amino)pyrimidin-2(1H)-one Diol (50.00 g, 0.19 mol) and pyridine (900 mL) were stirred for 1 h at RT, and then, cooled to −5° C. Trimethylsilyl chloride (145 mL, 1.14 mol) was added dropwise over a period of 20 min. The reaction mixture was stirred for 1 h at −5° C., and then, warmed to RT. The reaction mixture was stirred for 30 min at RT. 4-(Dimethylamino)pyridine (23.20 g, 0.19 mol) and monomethoxytrityl chloride (73.40 g, 0.24 mol) were added to the reaction mixture and the resulting reaction mixture was warmed to 57° C. overnight. Most of the solvent was removed in vacuo and the residue was azeotroped with toluene (500 mL). The residue was dissolved in DCM (700 mL) and a solution of saturated sodium bicarbonate (900 mL) was added dropwise to it while stirring. The reaction mixture was stirred for 30 min. The aqueous layer was further extracted with DCM (450 mL). The combined organic layers were dried over sodium sulfate, filtered and concentrated under reduced pressure. The residue was dissolved in methanol (700 mL) and ammonium fluoride was added. The reaction mixture was stirred at 60° C. for 4 h. Water (700 mL) was added to the reaction mixture. The mixture was heated at 50° C. for 10 min., then it was cooled to RT. Solvent was partially removed in vacuo. The residue was azeotroped with methanol and toluene. The crude product was purified via silica gel flash column chromatography (DCM/methanol 6%) to afford the expected compound.

Scheme 7
Preparation of Intermediate J and Compound 120

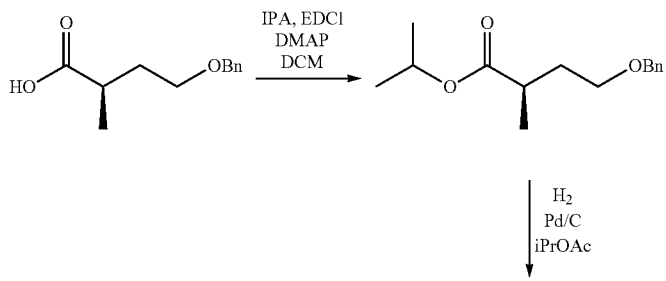

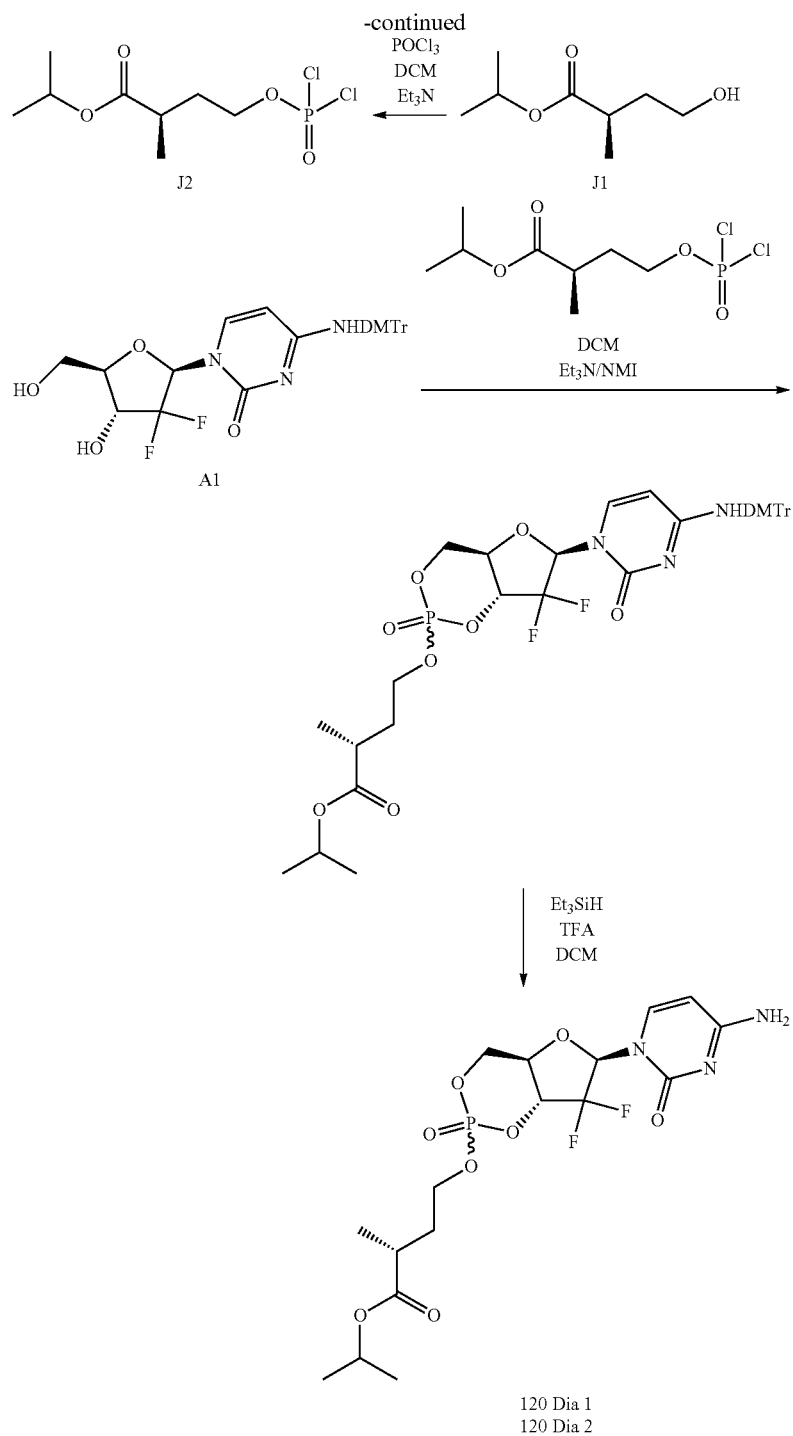

120 Dia 1
120 Dia 2

Example 20

Intermediate J1: Isopropyl (R)-4-hydroxy-2-methylbutanoate

Step 1: To a stirred solution of (R)-4-(benzyloxy)-2-methylbutanoic acid (15.00 g, 72.00 mmol) in DCM (220 mL), was added isopropanol (55.2 mL, 0.72 mol) followed by the addition of a solution of N-(3-dimethylaminopropyl)-N'-ethylcarbodiimide hydrochloride (16.60 g, 86.44 mmol) in DCM (100 mL). The reaction mixture was stirred, and then, 4-dimethylamino pyridine (0.88 g, 7.20 mmol) was added to the mixture. The reaction mixture was stirred under nitrogen at RT overnight. The resulting reaction mixture was washed with water (250 mL). The organic layer was washed with a 10% solution of citric acid (×2) and with brine, then it was dried over sodium sulfate, filtered and concentrated under reduced pressure to afford isopropyl (R)-4-(benzyloxy)-2-methylbutanoate. Step 2: To a suspension of palladium on carbon (3.30 g, 31.00 mmol) in isopropyl acetate (50 mL) was added a solution of isopropyl (R)-4-(benzyloxy)-2-methylbutanoate (16.50 g, 66.00 mmol) in isopropyl acetate (500 mL). The reaction mixture was degassed few times with nitrogen. Then the flask was filled with hydrogen and it was stirred under an atmosphere of hydrogen overnight. The reaction mixture was filtered through a pad of celite. The filtrates were concentrated under reduced pressure (water bath: 30° C.) and the resulting product was dried in vacuum oven for 4 h to afford the expected intermediate.

Intermediate J2: Isopropyl (R)-4-((dichlorophosphoryl)oxy)-2-methylbutanoate

A solution of phosphorus (V) oxychloride (1.54 mL, 16.50 mmol) in anhydrous DCM (25 mL) was cooled to −10° C. A solution of intermediate J1 (2.40 g, 15.00 mmol) and triethylamine (2.1 mL, 15.00 mmol) in anhydrous DCM (25 mL) was added to the previous solution dropwise over a period of 2 h at −10/−5° C. The reaction mixture was stirred at −10° C. overnight. The resulting reaction mixture was warmed to RT and solvent was removed in vacuo. The residue was dissolved in diethyl ether and filtered. Evaporation of diethyl ether gave the expected intermediate, which was used in the next step without further purification.

Compound 120

Isopropyl (R)-4-(((2R,4aR,6R,7aR)-6-(4-amino-2-oxopyrimidin-1(2H)-yl)-7,7-difluoro-2-oxidotetrahydro-4H-furo[3,2-d][1,3,2]dioxaphosphinin-2-yl)oxy)-2-methylbutanoate and Isopropyl (R)-4-(((2S,4aR,6R,7aR)-6-(4-amino-2-oxopyrimidin-1(2H)-yl)-7,7-difluoro-2-oxidotetrahydro-4H-furo[3,2-d][1,3,2]dioxaphosphinin-2-yfloxy)-2-methylbutanoate Step 1: To a solution of intermediate J2 in DCM (25 mL) was added dropwise over a period of 1.5 h a solution of 4-((bis(4-methoxyphenyl)(phenyl)methyl)amino)-1-((2R,4R,5R)-3,3-difluoro-4-hydroxy-5-(hydroxymethyl)tetrahydrofuran-2-yl)pyrimidin-2(1H)-one (6.00 g, 10.60 mmol) and triethylamine (5.1 mL, 36.50 mmol) in anhydrous DCM (25 mL). The reaction mixture was stirred for 15 min. and 1-methylimidazole (5.72 mL, 71.70 mmol) was added. After 4 h stirring at RT, solvent was removed under reduced pressure and the residue was dissolved in ethyl acetate. The resulting solution was washed with water and with brine. The organic layer was dried over sodium sulfate, filtered and concentrated under reduced pressure. The crude residue was purified via silica gel flash column chromatography (DCM/EtOAc: 20-40%) to afford the expected compound as a Sp/Rp mixture).

Step 2: A solution of isopropyl (2R)-4-(((4aR,6R,7aR)-6-(4-((bis(4-methoxyphenyl)(phenyl)methyl)amino)-2-oxopyrimidin-1(2H)-yl)-7,7-difluoro-2-oxidotetrahydro-4H-furo[3,2-d][1,3,2]dioxaphosphinin-2-yl) oxy)-2-methylbutanoate (1.75 g, 2.27 mmol) and triethylsilane (2.5 mL, 16.13 mmol) in anhydrous DCM (35 mL) was cooled to 0° C. Trifluoroacetic acid (1.3 mL, 16.98 mmol) was added dropwise to the reaction mixture over a period of 25 min. After the addition, the reaction mixture was warmed to RT, stirred for 2 h, and then concentrated under reduced pressure (water bath: 30° C.). The crude residue was azeotroped with toluene (×2), THF (×2), acetonitrile and chloroform, and then dried in the vacuum oven overnight. The crude compound was purified via silica gel flash column chromatography (DCM/methanol 1-5%) to afford the 2 expected isomers Sp and Rp.

Compound 120 Diastereoisomer 1

$^1$H NMR (DMSO-d$_6$, 400 MHz) δ (ppm) 7.82 (d, J=7.68 Hz, 1H), 7.77-7.71 (m, 2H), 6.44 (brs, 1H), 5.84 (d, J=7.68 Hz, 1H), 5.33 (brs, 1H), 4.89 (heptuplet, J=6.26 Hz, 1H), 4.77-4.70 (m, 1H), 4.65-4.63 (m, 1H), 4.40-4.38 (m, 1H), 4.17-4.09 (m, 2H), 2.00-1.92 (m, 1H), 1.77-1.69 (m, 1H), 1.19 (d, J=6.26 Hz, 3H), 1.185 (d, J=6.26 Hz, 3H), 1.10 (d, J=7.10 Hz, 3H); $^{31}$P NMR (DMSO-d$_6$, 162 MHz) δ (ppm) −5.74 (s, 1P); $^{19}$F NMR (DMSO-d$_6$, 376 MHz) δ (ppm) −116.75 (s, 2F); MS (ESI) m/z=468.4 (MO.

Compound 120 Diastereoisomer 2

$^1$H NMR (DMSO-d$_6$, 400 MHz) δ (ppm) 8.05 (brs, 1H), 7.90 (brs, 1H), 7.85 (d, J=7.37 Hz, 1H), 6.44 (brs, 1H), 5.91 (d, J=7.60 Hz, 1H), 4.98 (brs, 1H), 4.89 (heptuplet, J=6.27 Hz, 1H), 4.77-4.69 (m, 1H), 4.56-4.52 (m, 1H), 4.33-4.28 (m, 1H), 4.19-4.11 (m, 2H), 2.62-2.53 (m, 1H), 2.08-1.99 (m, 1H), 1.84-1.76 (m, 1H), 1.185 (d, J=6.27 Hz, 3H), 1.18 (d, J=6.27 Hz, 3H), 1.12 (d, J=7.07 Hz, 3H); $^{31}$P NMR (DMSO-d$_6$, 162 MHz) δ (ppm) −7.48 (s, 1P); $^{19}$F NMR (DMSO-d$_6$, 376 MHz) δ (ppm) −115.48-(−117.01) (m, 2F); MS (ESI) m/z=468.2 (MH$^+$).

Scheme 8
Preparation of Intermediates K and Compound 121

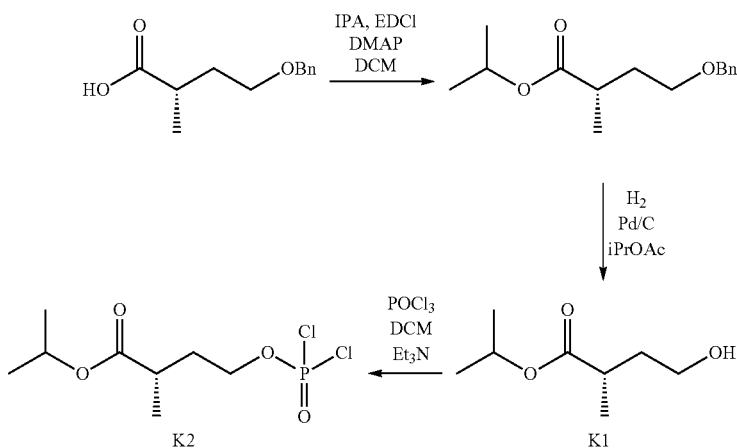

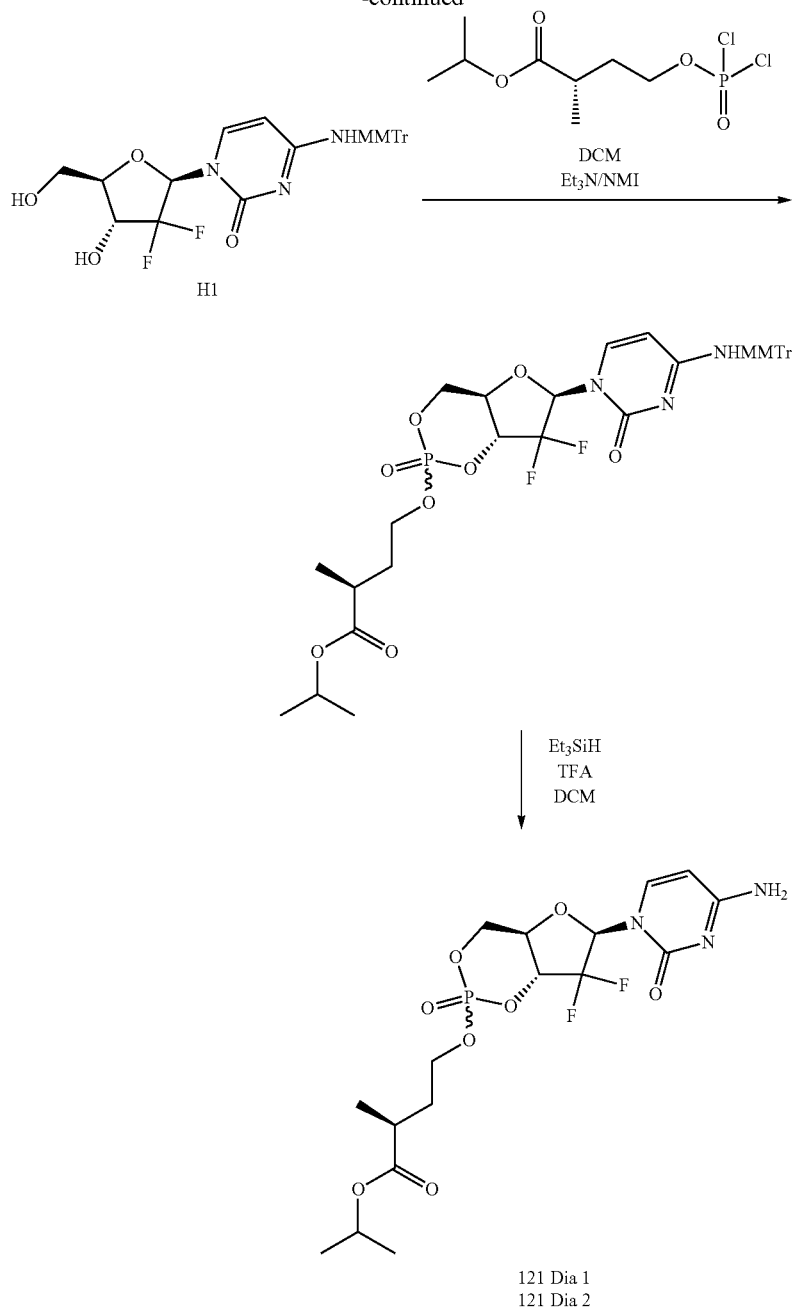

121 Dia 1
121 Dia 2

Example 21

Intermediate K1: Isopropyl (S)-4-hydroxy-2-methylbutanoate

Step 1: To a stirred solution of (S)-4-(benzyloxy)-2-methylbutanoic acid (30.00 g, 144.10 mmol) in DCM (400 mL), was added isopropanol (110.4 mL, 1.44 mol) followed by the addition of a solution of N-(3-dimethylaminopropyl)-N-ethylcarbodiimide hydrochloride (33.20 g, 172.90 mmol) in DCM (100 mL). The reaction mixture was stirred, and then, 4-dimethylamino pyridine (1.76 g, 14.40 mmol) was added to the mixture. The reaction mixture was stirred under nitrogen at RT overnight. The resulting reaction mixture was washed with water (700 mL). The organic layer was washed with a 10% solution of citric acid (×2) and with brine, then it was dried over sodium sulfate, filtered and concentrated under reduced pressure to afford isopropyl (S)-4-(benzyloxy)-2-methylbutanoate. Step 2: To a suspension of palladium on carbon (4.90 g, 46.04 mmol) in isopropyl acetate (700 mL) was added a solution of isopropyl (S)-4-(benzyloxy)-2-methylbutanoate (29.00 g, 115.84 mmol) in isopropyl acetate (200 mL). The reaction mixture was degassed few times with nitrogen. Then the flask was filled with hydrogen and it was stirred under an atmosphere of hydrogen for 2 h. The reaction mixture was filtered through a pad of celite. The filtrates were concentrated under reduced pressure (water bath: 30° C.) and the resulting product was dried in vacuum oven overnight to afford the expected intermediate.

Intermediate K2: Isopropyl (S)-4-((dichlorophosphoryl)oxy)-2-methylbutanoate

A solution of phosphorus (V) oxychloride (9.6 mL, 103.00 mmol) in anhydrous DCM (320 mL) was cooled to −10° C. A solution of intermediate K1 (15.00 g, 93.60 mmol) and triethylamine (13 mL, 93.60 mmol) in anhydrous DCM (160 mL) was added to the previous solution dropwise over a period of 4 h at −10/−5° C. The reaction mixture was stirred at −10° C. overnight. The resulting reaction mixture was warmed to RT and solvent was removed in vacuo. The residue was dissolved in diethyl ether and filtered. Evaporation of diethyl ether gave the expected intermediate, which was used in the next step without further purification.

Compound 121

Isopropyl (S)-4-(((2R,4aR,6R,7aR)-6-(4-amino-2-oxopyrimidin-1(2H)-yl)-7,7-difluoro-2-oxidotetrahydro-4H-furo[3,2-d][1,3,2]dioxaphosphinin-2-yl)oxy)-2-methylbutanoate and Isopropyl (S)-4-(((2S,4aR,6R,7aR)-6-(4-amino-2-oxopyrimidin-1(2H)-yl)-7,7-difluoro-2-oxidotetrahydro-4H-furo[3,2-d][1,3,2]dioxaphosphinin-2-yl)oxy)-2-methylbutanoate Step 1: A solution of intermediate K2 in anhydrous DCM (150 mL) was cooled to 0° C. A solution of 1-((2R,4R,5R)-3,3-difluoro-4-hydroxy-5-(hydroxymethyl)tetrahydrofuran-2-yl)-4-(((4-methoxyphenyl)diphenylmethyl)amino)pyrimidin-2(1H)-one (38.50 g, 71.70 mmol) and triethylamine (32 mL, 0.23 mol) in anhydrous DCM (200 mL) was added dropwise over a period of 2 h to this solution, followed by the addition of 1-methylimidazole (5.72 mL, 71.70 mmol). The reaction mixture was warmed to RT and was followed by LCMS. After 4 h stirring at RT, solvent was removed under reduced pressure and the residue was partitioned between ethyl acetate (1 L) and water (500 mL). The aqueous layer was further extracted with ethyl acetate (500 mL). The combined organic layers were washed with water and brine, dried over sodium sulfate, filtered and concentrated under reduced pressure. The crude compound was purified via silica gel flash column chromatography (DCM/methanol 0-1%) to afford the expected compound as a Sp/Rp mixture.

Step 2: A solution of isopropyl (2S)-4-(((4aR,6R,7aR)-7,7-difluoro-6-(4-(((4-methoxyphenyl)diphenylmethyl)amino)-2-oxopyrimidin-1(2H)-yl)-2-oxidotetrahydro-4H-furo[3,2-d][1,3,2]dioxaphosphinin-2-yl)oxy)-2-methylbutanoate (19.50 g, 26.40 mmol) and triethylsilane (27.9 mL, 0.18 mol) in anhydrous DCM (350 mL) was cooled to 0° C. Trifluoroacetic acid (24 mL, 313.40 mmol) was then added dropwise over a period of 1 h. The reaction mixture was warmed to RT, stirred for 3 h, and concentrated under reduced pressure (water bath: 30° C.). The residue was azeotroped with toluene (×3), acetonitrile, THF and DCM, and then, dried in the vacuum oven at 40° C. overnight. The crude compound was purified via silica gel flash column chromatography (DCM/methanol: 0-5%) to afford the 2 expected isomers Sp and Rp. A mixture of Sp/Rp isomers was further purified using 30% DCM in MeCN and then MeCN as a chromatography system to afford the Sp isomer and the Rp isomer.

Compound 121 Diastereoisomer 1

$^1$H NMR (DMSO-$d_6$, 400 MHz) δ (ppm) 7.79 (d, J=7.38 Hz, 1H), 7.57-7.55 (m, 2H), 6.45 (brs, 1H), 5.80 (d, J=7.63 Hz, 1H), 5.32-5.29 (m, 1H), 4.89 (heptuplet, J=6.27 Hz, 1H), 4.76-4.69 (m, 1H), 4.65-4.63 (m, 1H), 4.39-4.38 (m, 1H), 4.17-4.09 (m, 2H), 2.01-1.92 (m, 1H), 1.77-1.69 (m, 1H), 1.19 (d, J=6.27 Hz, 3H), 1.18 (d, J=6.27 Hz, 3H), 1.10 (d, J=7.10 Hz, 3H); $^{31}$P NMR (DMSO-$d_6$, 162 MHz) δ (ppm) −5.75 (s, 1P); $^{19}$F NMR (DMSO-$d_6$, 376 MHz) δ (ppm) −116.72 (s, 2F); MS (ESI) m/z=468.5 (MH$^+$).

Compound 121 Diastereoisomer 2

$^1$H NMR (DMSO-$d_6$, 400 MHz) δ (ppm) 8.10 (brs, 1H), 7.90 (brs, 1H), 7.86 (d, J=7.65 Hz, 1H), 6.43 (brs, 1H), 5.91 (d, J=7.53 Hz, 1H), 4.98 (brs, 1H), 4.89 (heptuplet, J=6.29 Hz, 1H), 4.77-4.69 (m, 1H), 4.58-4.53 (m, 1H), 4.32-4.29 (m, 1H), 4.15 (dd, J=14.37 Hz, 6.80 Hz, 2H), 2.63-2.54 (m, 1H), 2.08-1.99 (m, 1H), 1.84-1.75 (m, 1H), 1.185 (d, J=6.29 Hz, 6H), 1.12 (d, J=7.05 Hz, 3H); $^{31}$P NMR (DMSO-$d_6$, 162 MHz) δ (ppm) −7.47 (s, 1P); $^{19}$F NMR (DMSO-$d_6$, 376 MHz) δ (ppm) −115.46-(−117.01) (m, 2F); MS (ESI) m/z=468.3 (MH$^+$).

Scheme 9
Preparation of Intermediates L and Compound 122

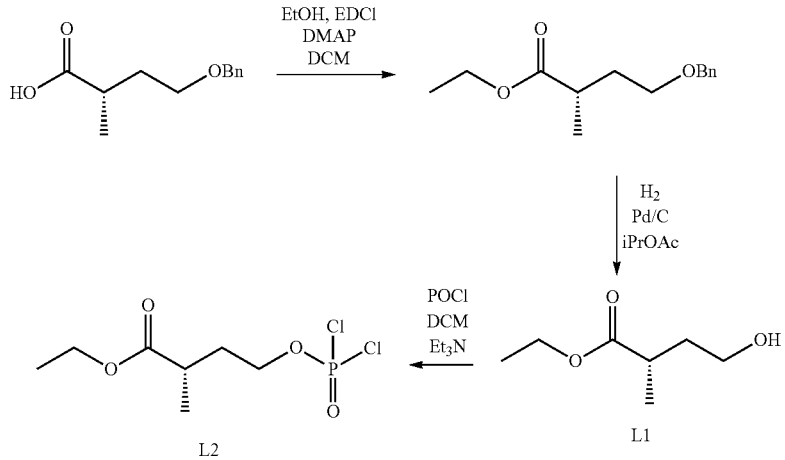

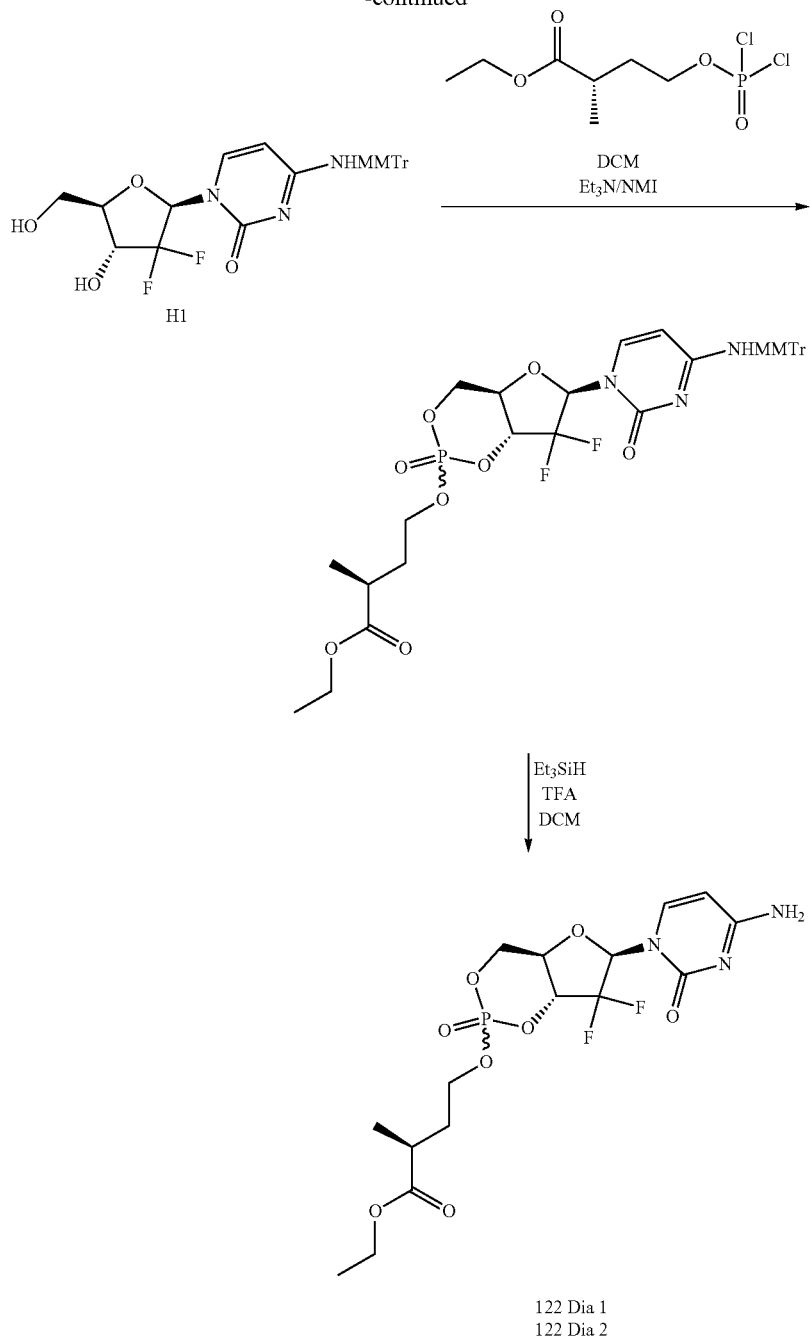

122 Dia 1
122 Dia 2

Example 22

Intermediate L1: Ethyl (S)-4-hydroxy-2-methylbutanoate

Step 1: To a solution of (S)-4-(benzyloxy)-2-methylbutanoic acid (14.00 g, 68.29 mmol) in DCM (200 mL) were added N-(3-Dimethylaminopropyl)-N-ethylcarbodiimide hydrochloride (15.60 g, 81.94 mmol), 4-dimethylamino pyridine (0.83 g, 6.82 mmol) and ethanol (39.7 mL, 0.68 mol). The reaction mixture was stirred under nitrogen at RT overnight. The resulting reaction mixture was washed with water (100 mL). The organic layer was washed with a 10% solution of citric acid (100 mL) and with a 1:1 mixture of brine and water (100 mL), then it was dried over sodium sulfate, filtered and concentrated under reduced pressure to afford ethyl (S)-4-(benzyloxy)-2-methylbutanoate. Step 2: To a suspension of palladium on carbon (1.40 g, 13.15 mmol) in isopropyl acetate (350 mL) was added a solution of ethyl (S)-4-(benzyloxy)-2-methylbutanoate (14.2 g, 60.94 mmol) in isopropyl acetate (50 mL). The reaction mixture was degassed few times with nitrogen. Then the flask was filled with hydrogen and it was stirred under an atmosphere of hydrogen for 7 h. The reaction mixture was filtered through a pad of celite. The filtrates were concentrated under reduced pressure to afford the expected intermediate.

Intermediate L2: Ethyl (S)-4-((dichlorophosphoryl)oxy)-2-methylbutanoate

A solution of phosphorus (V) oxychloride (9.90 g, 64.71 mmol) in anhydrous DCM (70 mL) was cooled to −10° C. A solution of intermediate L1 (8.59 g, 58.83 mmol) and triethylamine (8.2 mL, 58.83 mmol) in anhydrous DCM (70 mL) was added to the previous solution dropwise at −10/−5° C. The reaction mixture was stirred at −10° C. overnight. The reaction mixture was warmed to RT and solvent was removed in vacuo. Diethyl ether was added to the residue, filtered and concentrated under reduced pressure to afford the expected intermediate, which was used in the next step without further purification.

Compound 122

Ethyl (S)-4-(((2S,4aR,6R,7aR)-6-(4-amino-2-oxopyrimidin-1(2H)-yl)-7,7-difluoro-2-oxidotetrahydro-4H-furo[3,2-d][1,3,2]dioxaphosphinin-2-yl)oxy)-2-methylbutanoate and Ethyl (S)-4-(((2R,4aR,6R,7aR)-6-(4-amino-2-oxopyrimidin-1(2H)-yl)-7,7-difluoro-2-oxidotetrahydro-4H-furo[3,2-d][1,3,2]dioxaphosphinin-2-yl)oxy)-2-methylbutanoate Step 1: To a solution of intermediate L2 in DCM (70 mL) was added dropwise a solution of 1-((2R,4R,5R)-3,3-difluoro-4-hydroxy-5-(hydroxymethyl)tetrahydrofuran-2-yl)-4-(((4-methoxyphenyl)diphenylmethyl)amino)pyrimidin-2(1H)-one (22.06 g, 41.18 mmol) and triethylamine (19.6 mL, 141.13 mmol) in anhydrous DCM (64 mL). The reaction mixture was stirred for 30 min, and then, 1-methylimidazole (3.3 mL, 41.18 mmol) was added. The reaction mixture was stirred at RT for 4 hours and concentrated under reduced pressure. The crude residue was partitioned in ethyl acetate and water (350 mL). The aqueous layer was further extracted with ethyl acetate (×2). The combined organic layers were washed with brine, dried over sodium sulfate, filtered and concentrated under reduced pressure. The crude compound was purified via silica gel flash column chromatography (DCM/ethanol 2-3%) to afford the expected compound as a Sp/Rp mixture.

Step 2: To a solution of ethyl (2S)-4-(((4aR,6R,7aR)-7,7-difluoro-6-(4-(((4-methoxyphenyl)diphenyl-methyl)amino)-2-oxopyrimidin-1(2H)-yl)-2-oxidotetrahydro-4H-furo[3,2-d][1,3,2]dioxaphosphinin-2-yl)oxy)-2-methylbutanoate (8.60 g, 11.86 mmol) in anhydrous DCM (250 mL) at 0° C. was added triethylsilane (9.5 mL, 61.03 mmol). A solution of trifluoroacetic acid (5.1 mL, 66.60 mmol) in DCM (20 mL) was added dropwise to the reaction mixture over a period of 1 h. The resulting reaction mixture was stirred at 0° C. for 10 min and at RT for 2.5 h. Solvent was removed under reduced pressure and the residue was azeotroped with toluene (×2). The crude residue was purified via silica gel flash column chromatography (DCM/ethanol 4-12%) to afford the 2 expected isomers Sp and Rp.

Compound 122 Diastereoisomer 1

$^1$H NMR (DMSO-$d_6$, 400 MHz) δ (ppm) 7.98 (brs, 1H), 7.85-7.83 (m, 2H), 6.44 (brs, 1H), 5.89 (d, J=7.32 Hz, 1H), 4.98 (brs, 1H), 4.77-4.68 (m, 1H), 4.57-4.52 (m, 1H), 4.33-4.27 (m, 1H), 4.16 (dd, J=14.71 Hz, 6.74 Hz, 2H), 4.08 (q, J=7.05 Hz, 2H), 2.66-2.60 (m, 1H), 2.09-2.00 (m, 1H), 1.85-1.76 (m, 1H), 1.19 (t, J=7.05 Hz, 3H), 1.14 (d, J=7.05 Hz, 3H); $^{31}$P NMR (DMSO-$d_6$, 162 MHz) δ (ppm) −7.48 (s, 1P); $^{19}$F NMR (DMSO-$d_6$, 376 MHz) δ (ppm) −115.46-(−116.99) (m, 2F); MS (ESI) m/z=454.0 (MH$^+$).

Compound 122 Diastereoisomer 2

$^1$H NMR (DMSO-$d_6$, 400 MHz) δ (ppm) 7.78 (d, J=7.57 Hz, 1H), 7.54 (brs, 1H), 7.51 (brs, 1H), 6.46 (brs, 1H), 5.80 (d, J=7.59 Hz, 1H), 5.32-5.30 (m, 1H), 4.77-4.70 (m, 1H), 4.66-4.64 (m, 1H), 4.40-4.39 (m, 1H), 4.17-4.11 (m, 2H), 4.08 (q, J=7.07 Hz, 2H), 2.61-2.53 (m, 1H), 2.03-1.94 (m, 1H), 1.79-1.71 (m, 1H), 1.20 (t, J=7.07 Hz, 3H), 1.12 (d, J=7.07 Hz, 3H); $^{31}$P NMR (DMSO-$d_6$, 162 MHz) δ (ppm) −5.79 (s, 1P); $^{19}$F NMR (DMSO-$d_6$, 376 MHz) δ (ppm) −116.73 (s, 2F); MS (ESI) m/z=454.0 (MH$^+$).

Scheme 10
Preparation of Intermediates M and Compound 123

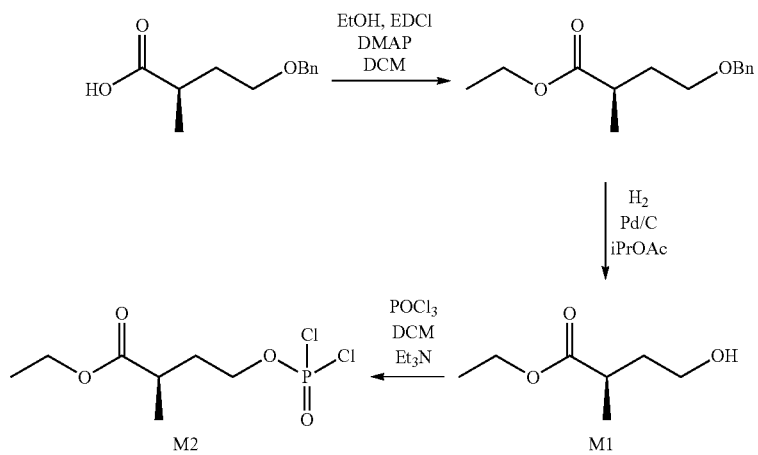

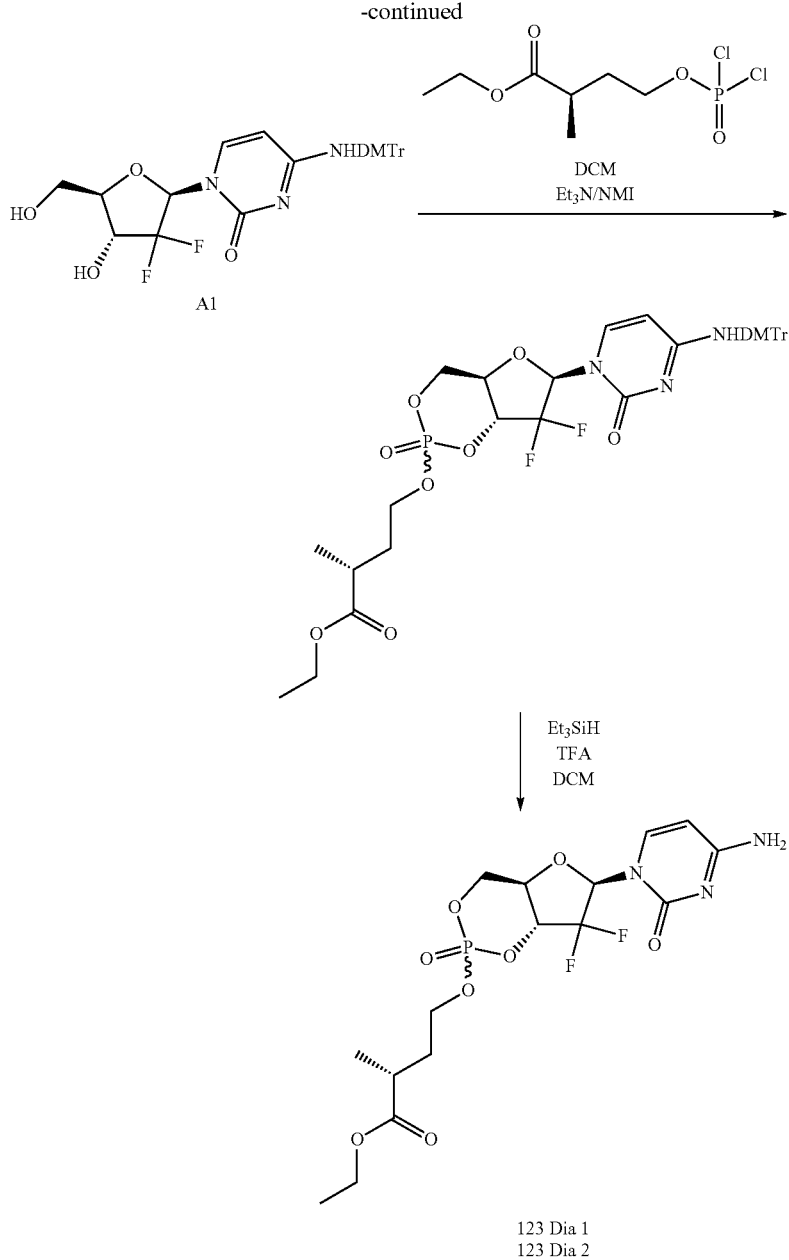

123 Dia 1
123 Dia 2

Example 23

Intermediate M1: Ethyl (R)-4-hydroxy-2-methylbutanoate

Step 1: To a solution of (R)-4-(benzyloxy)-2-methylbutanoic acid (11.43 g, 54.95 mmol) in DCM (170 mL) were added N-(3-Dimethylaminopropyl)-N-ethylcarbodiimide hydrochloride (13.40 g, 70.16 mmol), 4-dimethylamino pyridine (0.69 g, 5.65 mmol) and ethanol (34 mL, 0.58 mol). The reaction mixture was stirred under nitrogen at RT overnight. The resulting reaction mixture was washed with water (100 mL). The organic layer was washed with a 10% solution of citric acid (100 mL) and with a 1:1 mixture of brine and water (100 mL), dried over sodium sulfate, filtered and concentrated under reduced pressure to afford ethyl (R)-4-(benzyloxy)-2-methylbutanoate. Step 2: To a suspension of palladium on carbon (1.64 g, 15.41 mmol) in isopropyl acetate (400 mL) was added a solution of ethyl (R)-4-(benzyloxy)-2-methylbutanoate (15.34 g, 65.00 mmol) in isopropyl acetate (50 mL). The reaction mixture was degassed few times with nitrogen. Then the flask was filled with hydrogen and it was stirred under an atmosphere of hydrogen for 7 h. The resulting reaction mixture was filtered through a pad of celite and washed with ethyl acetate (180 mL). The filtrates were concentrated under reduced pressure to afford the expected intermediate.

Intermediate M2: Ethyl (R)-4-(((dichlorophosphoryl)oxy)-2-methylbutanoate

A solution of phosphorus (V) oxychloride (7.56 g, 64.04 mmol) in anhydrous DCM (68 mL) was cooled to −10° C. A solution of intermediate M1 (8.50 g, 58.22 mmol) and triethylamine (5.88 g, 58.22 mmol) in anhydrous DCM (34 mL) was added to the previous solution dropwise at −10/−5° C. The reaction mixture was stirred at −10° C. overnight. The resulting reaction mixture was warmed to RT and solvent was removed in vacuo. Diethyl ether was added to the residue, filtered and concentrated under reduced pressure to afford the expected intermediate, which was used in the next step without further purification.

Compound 123

Ethyl (R)-4-(((2S,4aR,6R,7aR)-6-(4-amino-2-oxopyrimidin-1(2H)-yl)-7,7-difluoro-2-oxidotetrahydro-4H-furo[3,2-d][1,3,2]dioxaphosphinin-2-yloxy)-2-methylbutanoate and Ethyl (R)-4-(((2R,4aR,6R,7aR)-6-(4-amino-2-oxopyrimidin-1(2H)-yl)-7,7-difluoro-2-oxidotetrahydro-4H-furo[3,2-d][1,3,2]dioxaphosphinin-2-yl)oxy)-2-methylbutanoate Step 1: To a solution of 4-((bis(4-methoxyphenyl)(phenyl)methyl)amino)-1-((2R,4R,5R)-3,3-difluoro-4-hydroxy-5-(hydroxymethyl)tetrahydrofuran-2-yl)pyrimidin-2(1H)-one (20.00 g, 35.40 mmol) and triethylamine (14.11 g, 139.73 mmol) in anhydrous DCM (65 mL) was added a solution of intermediate L2 in DCM (80 mL). The reaction mixture was stirred for 30 min at RT, and then, 1-methylimidazole (2.82 mL, 35.40 mmol) was added. After 4 h stirring at RT, the reaction mixture was concentrated under reduced pressure. The crude residue was partitioned in ethyl acetate (200 mL) and water (200 mL). The aqueous layer was further extracted with ethyl acetate. The combined organic layers were dried over sodium sulfate, filtered and concentrated under reduced. The crude compound was purified via silica gel flash column chromatography (DCM/EtOAc 40-50%) to afford the expected compound as a Sp/Rp mixture.

Step 2: To a solution of ethyl (2R)-4-((((4aR,6R,7aR)-6-(4-((bis(4-methoxyphenyl)(phenyl)methyl)amino)-2-oxopyrimidin-1(2H)-yl)-7,7-difluoro-2-oxidotetra-hydro-4H-furo[3,2-d][1,3,2]dioxaphosphinin-2-yl)oxy)-2-methylbutanoate (7.50 g, 9.92 mmol) in anhydrous dichloromethane (200 mL) at 0° C. was added triethylsilane (8.25 mL, 53.23 mmol). Trifluoroacetic acid (4.5 mL, 58.76 mmol) was added dropwise to the reaction mixture over a period of 1 h. The reaction mixture was stirred at 0° C. for 10 min and at RT for 1.5 h. Solvent was removed under reduced pressure and the residue was azeotroped with toluene (×2). The crude residue was purified via silica gel flash column chromatography (DCM/EtOH 4-10%) to afford the 2 expected isomers Sp and Rp.

Compound 123 Diastereoisomer 1

$^1$H NMR (DMSO-$d_6$, 400 MHz) δ (ppm) 8.04 (brs, 1H), 7.86-7.84 (m, 2H), 6.44 (brs, 1H), 5.90 (d, J=7.70 Hz, 1H), 5.02-4.92 (m, 1H), 4.78-4.69 (m, 1H), 4.56-4.52 (m, 1H), 4.34-4.27 (m, 1H), 4.20-4.13 (m, 2H), 4.07 (q, J=7.15 Hz, 2H), 2.65-2.60 (m, 1H), 2.09-2.00 (m, 1H), 1.85-1.77 (m, 1H), 1.18 (t, J=7.15 Hz, 3H), 1.14 (d, J=6.97 Hz, 3H); $^{31}$P NMR (DMSO-$d_6$, 162 MHz) δ (ppm) −7.50 (s, 1P); $^{19}$F NMR (DMSO-$d_6$, 376 MHz) δ (ppm) −115.49-(−117.02) (m, 2F); MS (ESI) m/z=454.0 (MH$^+$).

Compound 123 Diastereoisomer 2

$^1$H NMR (DMSO-$d_6$, 400 MHz) δ (ppm) 8.12 (brs, 1H), 7.94 (brs, 1H), 7.88 (d, J=7.81 Hz, 1H), 6.43 (brs, 1H), 5.89 (d, J=7.81 Hz, 1H), 5.36-5.33 (m, 1H), 4.78-4.71 (m, 1H), 4.66-4.61 (m, 1H), 4.44-4.37 (m, 1H), 4.18-4.11 (m, 2H), 4.07 (q, J=7.02 Hz, 2H), 2.59-2.53 (m, 1H), 2.02-1.93 (m, 1H), 1.79-1.70 (m, 1H), 1.19 (t, J=7.02 Hz, 3H), 1.12 (d, J=7.14 Hz, 3H); $^{31}$P NMR (DMSO-$d_6$, 162 MHz) δ (ppm) −5.70 (s, 1P); $^{19}$F NMR (DMSO-$d_6$, 376 MHz) δ (ppm) −116.13-(−117.35) (m, 2F); MS (ESI) m/z=454.0 (MH$^+$).

Example 24

Compound 124

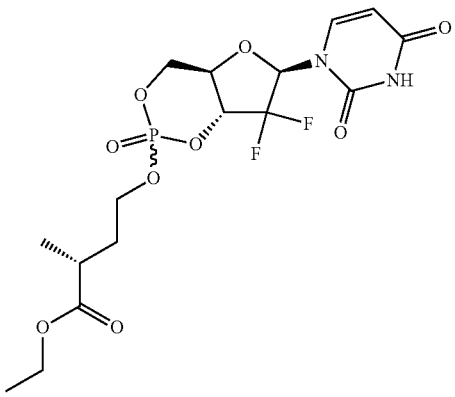

Compound 124 Dia 1 was synthesized from 1-((2R,4R,5R)-3,3-difluoro-4-hydroxy-5-(hydroxymethyl)tetrahydrofuran-2-yl)pyrimidine-2,4(1H,3H)-dione and intermediate M2 according to a similar method described in scheme 10 and to the procedure described for compound 123.

Compound 124 Diastereoisomer 1

$^1$H NMR (DMSO-$d_6$, 400 MHz) δ (ppm) 11.73 (s, 1H), 7.87 (d, J=8.05 Hz, 1H), 6.39 (brs, 1H), 5.80 (d, J=8.05 Hz, 1H), 5.12-5.05 (m, 1H), 4.78-4.69 (m, 1H), 4.57-4.52 (m, 1H), 4.34-4.28 (m, 1H), 4.20-4.12 (m, 2H), 4.07 (q, J=7.10 Hz, 2H), 2.65-2.58 (m, 1H), 2.09-2.01 (m, 1H), 1.85-1.77 (m, 1H), 1.18 (t, J=7.10 Hz, 3H), 1.14 (d, J=7.10 Hz, 3H); $^{31}$P NMR (DMSO-$d_6$, 162 MHz) δ (ppm) −7.54 (s, 1P); MS (ESI) m/z=453.2 (MH$^−$).

In Vitro Inhibition

Materials

Cells were grown in RPMI-1640 supplemented with L-Glutamine and 10% FBS of the following cell lines:

CCRF-CEM; HL-60; KG-1; CFPAC-1; MiaPACA-2; BxPC-3; HepG2; MDA-MB-231; HCT-116; A498; and NCI-H69

Method 18, 96 well plates of each cell line were seeded with the optimized number of cells per well in a total volume of 50 μper well. The plates were left overnight. Plate wells were seeded with 100 pt media for media control. The following day, cells were exposed to test compounds as described below. At the same time as drug exposure, a CTG assay was conducted on the 18$^{th}$ plate for the 0 hr count.

The compounds were added to cells and medium already on the plate to give desired final concentrations. 50 μL media were added to cell control wells, and 50 μL of mix added to vehicle control wells. 10 μM Doxorubicin was added to appropriate wells as control. Cells exposed to test compound were incubated at 37° C. for 72 hr followed by a CTG assay.

CellTiter-Glo (CTG)

At the end of the 72 hr exposure period, plates were removed for a CellTiter-Glo (CTG) assay from a 37° C., 5% $CO_2$ incubator and placed on the bench at room temperature for 30 mins. 100 μL of CellTiter-Glo reagent was added and mixed for 2 mins, followed by a further 10 min incubation at room temperature. Luminescence was recorded using Synergy 4.0.

The exemplified compounds were tested in accordance with this method and were found to have $IC_{50}$ values of less than 10004 at each cell line. The results for compounds are provided in Tables 1 and 2.

TABLE 1

In vitro inhibition of CCRF-CEM; HL-60; KG-1; CFPAC-1; MiaPACA-2; BxPC-3; HepG2;

| Compound | CCRF-CEM | HL-60 | KG-1 | CFPAC-1 | MiaPACA-2 | BxPC-3 | HepG2 |
|---|---|---|---|---|---|---|---|
| | | | | $IC_{50}$ (μM) | | | |
| 101 (diastereomer 1) | | | | A | A | C | A |
| 101 (diastereomer 2) | | | | B | B | C | B |
| 102 (diastereomer 1) | | | | B | B | C | B |
| 102 (diastereomer 2) | | A | | B | B | B | A |
| 103 (diastereomer 1) | A | A | A | A | B | C | A |
| 103 (diastereomer 2) | A | A | A | B | B | B | A |
| 104 (diastereomer 1) | | | | A | A | A | A |
| 104 (diastereomer 2) | | | | A | A | A | A |
| 105 (diastereomer 1) | | | | A | A | A | A |
| 105 (diastereomer 2) | | | | B | B | B | A |
| 106 (diastereomer 1) | | | | B | B | C | A |
| 106 (diastereomer 2) | | | | B | B | B | A |
| 107 | | | | A | A | A | A |
| 108 (diastereomer 1) | A | A | A | A | A | B | A |
| 108 (diastereomer 2) | A | A | A | A | A | A | A |
| 109 | | | | B | C | C | B |
| 111 | | | | C | C | C | C |
| 111 (diastereomer 1) | | | | | | | |
| 111 (diastereomer 2) | | | | A | A | B | A |
| 112 (diastereomer 1) | C | B | C | C | C | C | C |
| 112 (diastereomer 2) | A | A | B | B | C | C | B |
| 114 | | | | A | A | A | A |
| 115 | | | | A | A | B | A |
| 116 (diastereomer 1) | | | | C | C | C | C |
| 116 (diastereomer 2) | | | | C | C | C | C |
| 117 | A | A | A | A | A | A | A |
| 118 | | | | A | A | A | A |
| 119 | | | | C | C | C | C |

TABLE 2

In vitro inhibition of MDA-MB-231; HCT-116; A498; and NCI-H69

| Compound | MDA-MB-231 | HCT-116 | A498 | NCI-H69 |
|---|---|---|---|---|
| | | $IC_{50}$(μM) | | |
| 101 (diastereomer 1) | C | B | B | C |
| 101 (diastereomer 2) | C | C | C | C |
| 102 (diastereomer 1) | C | C | C | C |
| 102 (diastereomer 2) | C | B | C | C |
| 103 (diastereomer 1) | C | B | C | C |
| 103 (diastereomer 2) | C | B | C | C |
| 104 (diastereomer 1) | B | B | C | B |
| 104 (diastereomer 2) | B | B | A | B |
| 105 (diastereomer 1) | C | A | C | B |
| 105 (diastereomer 2) | C | C | B | C |
| 106 (diastereomer 1) | C | C | C | C |
| 106 (diastereomer 2) | C | B | C | C |
| 107 | C | B | C | B |
| 108 (diastereomer 1) | B | B | A | B |

TABLE 2-continued

In vitro inhibition of MDA-MB-231; HCT-116; A498; and NCI-H69

| Compound | MDA-MB-231 | HCT-116 | A498 | NCI-H69 |
|---|---|---|---|---|
| | | IC$_{50}$(µM) | | |
| 108 (diastereomer 2) | B | B | C | C |
| 109 | C | C | C | C |
| 111 (diastereomer 1) | C | C | C | C |
| 111 (diastereomer 2) | C | A | C | C |
| 112 (diastereomer 1) | C | C | C | C |
| 112 (diastereomer 2) | C | C | C | C |
| 114 | C | B | A | C |
| 115 | C | A | C | B |
| 116 (diastereomer 1) | C | C | C | C |
| 116 (diastereomer 2) | C | C | C | C |
| 117 | B | A | A | A |
| 118 | B | A | A | A |
| 119 | C | C | C | C |

The IC$_{50}$ values in Tables 1 and 2 are as follows:
A=<1 µM
B=≥1 and 10≤µM
C=>10 and ≤100 µM The following compounds were further tested in HuH-1: HuH-1 cells were purchased from JCRB and tested with the following method:

Day 1:

Cells are suspended at a specific density in a specific culture medium (see table in 2.Cell lines).

Then, 100 µl of cell suspension are plated per well in 96-well plates.

Day 2:

Compounds or negative controls (DMSO) are added to the cells (100 µl of a compound solution in its specific medium with a final concentration of 0.15% DMSO).

Each compound concentration is tested in duplicate (6 concentrations per compound).

Cells are incubated at 37° C. for 72 h without treating again.

Day 4:

SDS is added to control wells (final concentration of 1%) and kept for 15 min at 37° C. SDS 1% represents the positive control of proliferation inhibition.

Cell supernatant is removed and 100 µl of a MTT (3-[4.5-dimethylthiazol-2-yl]-2.5-diphenyltetrazolium bromide) solution in fresh medium are added per well (MTT final concentration of 0.5 mg/ml) and incubated for 4 h at 37° C.

MTT reaction is stopped and homogenized by adding 100 µl/well of SDS 10%, 0.01M HCl and incubated for 2 h at 37° C.

Absorbance is measured at 570 nm.

TABLE 3

In vitro inhibition of HuH-1

| Compound | HuH-1: relative IC50 (µM) |
|---|---|
| 122 Diastereoisomer 1 | A |
| 122 Diastereoisomer 2 | A |
| 123 Diastereoisomer 1 | A |
| 123 Diastereoisomer 2 | A |
| 120 Diastereoisomer 1 | A |
| 120 Diastereoisomer 2 | A |
| 121 Diastereoisomer 1 | A |
| 121 Diastereoisomer 2 | A |
| 102 Diastereoisomer 1 | B |
| Gemcitabine | A |

The IC$_{50}$ values in Table 3 are as follows:
A=<0.3 µM
B=≥0.3 µM

In Vivo Mouse PK

The in vivo mouse PK of compound 101 (diastereomers 1 and 2) (prodrugs of gemcitabine) was compared to Gemcitabine after IP injection.

Animals: male C57BL/6 mice

Dosing route: intraperitoneal

Dosing vehicle: 60% PEG 200:40% D5W, Dose Volume=5 mL/kg

Each animal provided liver specimen, and there were 3 animals per sample time (1, 2, 4, 24 h post-dose for liver). Gemcitabine triphosphate (GemCTP) and its uracil triphosphate metabolite (GemUTP) were monitored.

| Compound | Dose route | Dose mg/kg | Analyte | Liver Tmax (hr) | Liver Cmax (pmol/g) | Liver AUClast (hr * pmol/g) | Liver Tlast (hr) | Liver Clast (pmol/g) |
|---|---|---|---|---|---|---|---|---|
| Compound 101 (diastereomer 1) | IP | 150 | GemCTP | 1 | 46000 | 150000 | 24 | 24.6 |
| | | | GemUTP | 2 | 1370 | 3710 | 4 | 843 |
| Compound 101 (diastereomer 2) | IP | 150 | GemCTP | 1 | 11500 | 26000 | 4 | 2900 |
| | | | GemUTP | 2 | 537 | 1370 | 4 | 259 |
| Gemcitabine | IP | 90 | GemCTP | 1 | 1750 | 6720 | 24 | 48.7 |
| | | | GemUTP | 2 | 1220 | 5530 | 24 | 137 |

The experiments demonstrated the superiority of the gemcitabine prodrug to deliver gemcitabine triphosphate in the liver as compared to the parent nucleoside by >22 folds AUC. Finally stereochemistry on the phosphorus atom was found to impact the rate of prodrug metabolism as demonstrated by the 5.7 fold higher GemCTP AUC of compound 101 diastereomer 1 compared to compound 101 diastereomer 2.

Compound 102 Diastereoisomer 1 was also tested in Mouse CD-1:
IV (treatment)
Dose: 126 mg/kg (Compound 102 dia 1); 90 mg/kg (Gemcitabine);
Dose Volume: 5 ml/kg
Formulation: 25.2 mg/ml of the tested drug in 60% PEG200/40% D5W
(SOLUTION)
Fasted, mouse CD-1, female

| | MOUSE CD-1 | |
|---|---|---|
| | Compound 102 (diastereomer 1) | Gemcitabine |
| Liver AUC(0-24 h) GemC-TP μM*hour | 28075 | 43 |
| AUC(0-24 h) GemU-TP μM*hour | 1445 | 38 |

The invention claimed is:

1. A compound according to Formula I:

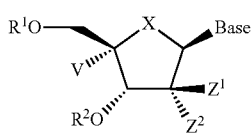
(I)

or a pharmaceutically acceptable salt thereof, wherein:

Base is a nucleobase:

X is O or S;

V is hydrogen, halogen or amino;

$Z^1$ is halogen;

$Z^2$ is halogen;

$R^1$ and $R^2$ together with the two oxygen atoms to which they are attached form the ring:

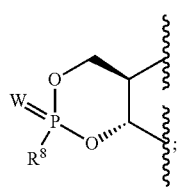

$R^8$ is $C_{1-10}$alkylcarbonylthio$C_{1-10}$alkoxy,

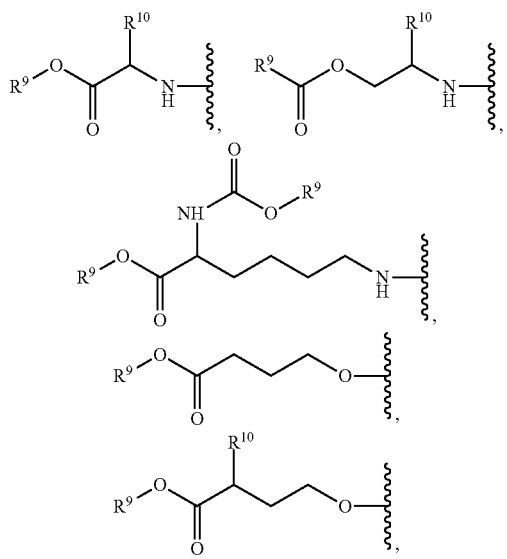

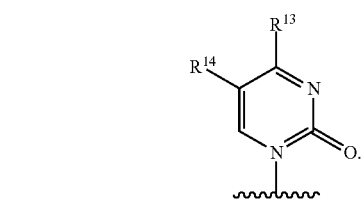;

$R^9$ is $C_{1-10}$alkyl, $C_{3-10}$cycloalkyl, aryl or aryl$C_{1-6}$alkyl;

$R^{10}$ is $C_{1-10}$alkyl or $COOR^9$;

$R^{11}$ is $C_{1-10}$alkylcarbonyloxy$C_{1-10}$alkyl, $C_{3-10}$cycloalkylcarbonyoxy, aryl, aryloxy, $C_{1-10}$alkylaryl, aryl$C_{1-10}$alkyl, heteroaryl, heteroaryl$C_{1-10}$alkyl or $C_{1-10}$alkylheteroaryl;

$R^z$ is $C_{2-11}$alkenyl, $C_{2-11}$alkynyl, $C_{1-10}$alkoxycarbonyl$C_{1-10}$alkyl, $C_{1-10}$alkylcarbonylthio$C_{1-10}$alkyl, $C_{1-10}$alkyldisulfide$C_{1-6}$alkyl, aryl or heteroaryl$C_{1-10}$alkyl, wherein alkyl is optionally substituted by one, two or three substituents independently selected from halogen and hydroxy, and heteroaryl is substituted by one or two substituents selected from $C_{1-10}$ alkyl and nitro; and W is O or S.

2. A compound of claim 1, wherein W is O.

3. A compound of claim 2 wherein Base is

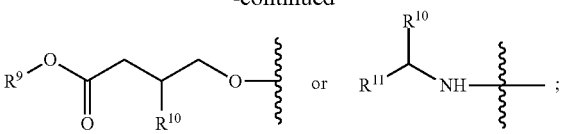

wherein $R^{12}$ is independently hydrogen, hydroxy, $OR^a$, chloro, bromo, fluoro, iodo, sulfanyl, $NR^bR^c$ or —$C_{1-10}$alkyl-$NR^bR^c$;

$R^{13}$ is hydrogen, hydroxy, —$NR^bR^c$, azido, oxo, or —$OR^a$;

$R^{14}$ is hydrogen, methyl, hydroxy, chloro, bromo, fluoro, iodo or —$NR^bR^c$;

$R^a$ is independently $C_{1-10}$alkyl or $C_{3-10}$Cycloalkyl; and each of $R^b$ and $R^c$ is independently hydrogen, $C_{1-10}$alkyl, $C_{1-10}$alkylcarbonyl, $C_{2-10}$alkenyl, $C_{2-10}$alkynyl, $C_{3-10}$cycloalkyl, aryl, heterocycle or heteroaryl.

4. A compound of claim 3 wherein Base is

5. A compound of claim 4 wherein $R^8$ is
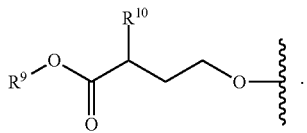
6. A compound of claim 1, wherein said compound is selected from:
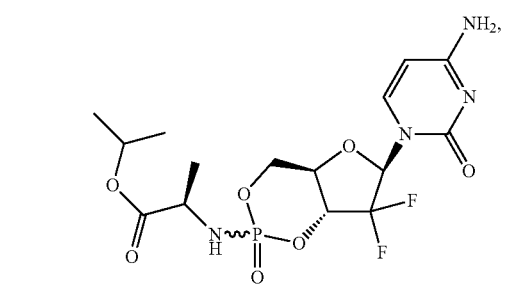
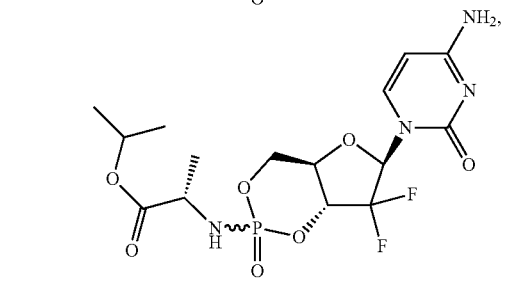
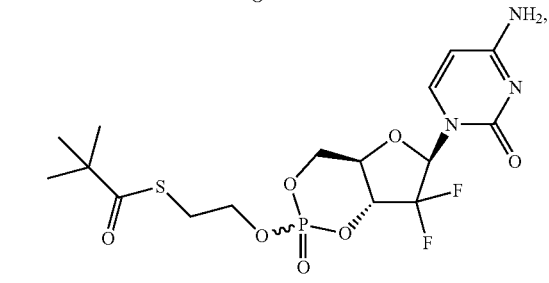
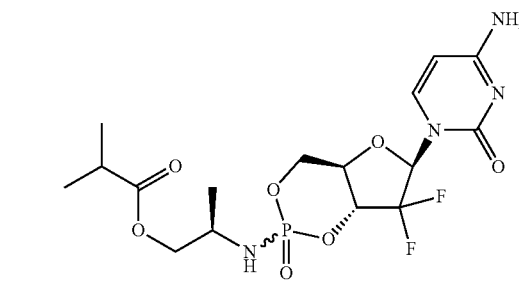
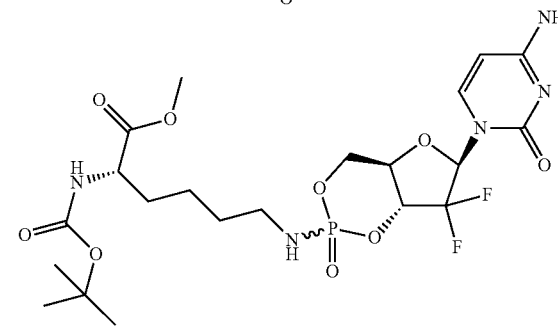
-continued
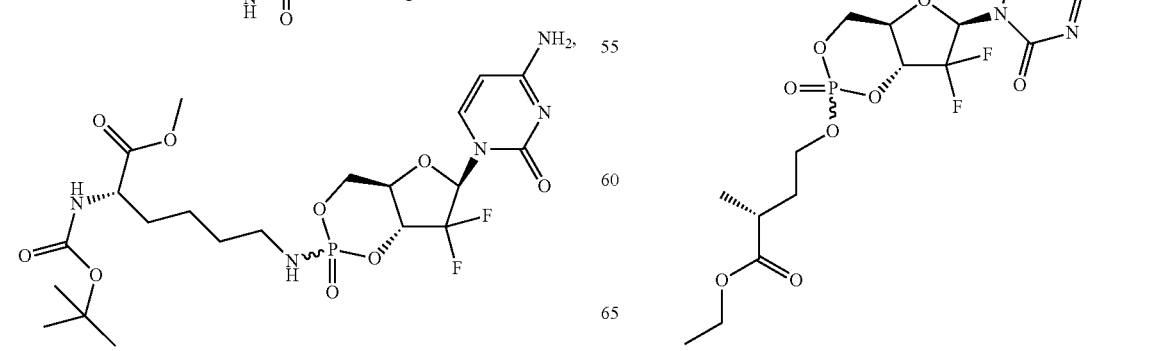

117
-continued
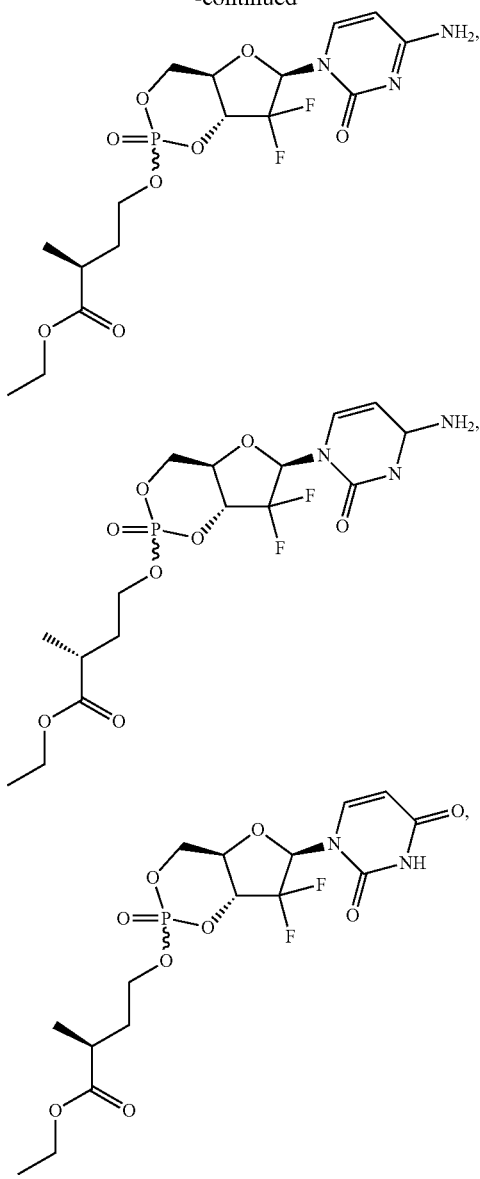
118
-continued
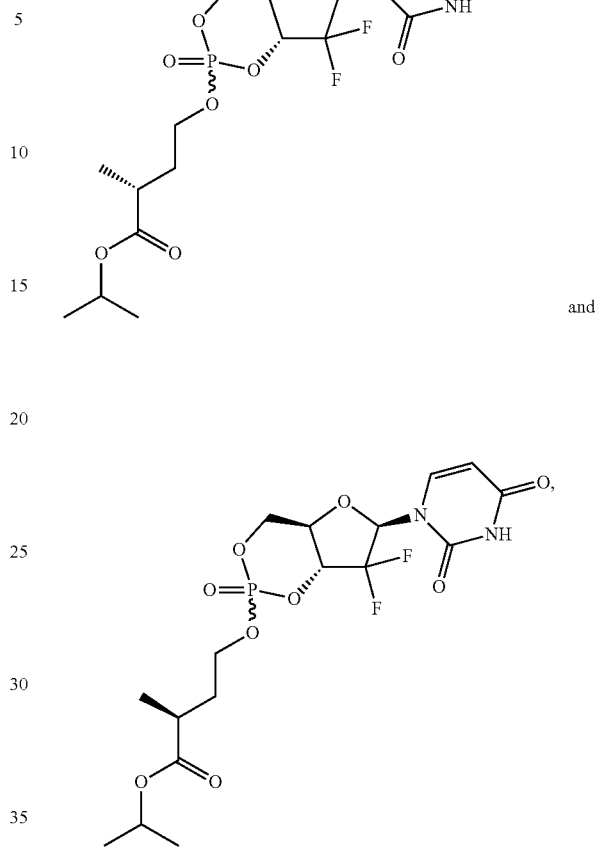
and pharmaceutically acceptable salts thereof.
7. A pharmaceutical composition comprising a compound of claim 1, or a pharmaceutically acceptable salt thereof, together with a pharmaceutically acceptable carrier or diluent.
* * * * *